(12) United States Patent
Lin et al.

(10) Patent No.: US 10,647,733 B2
(45) Date of Patent: May 12, 2020

(54) METAL-ORGANIC FRAMEWORKS CONTAINING NITROGEN-DONOR LIGANDS FOR EFFICIENT CATALYTIC ORGANIC TRANSFORMATIONS

(71) Applicant: The University of Chicago, Chicago, IL (US)

(72) Inventors: Wenbin Lin, Chicago, IL (US); Kuntal Manna, Chicago, IL (US); Teng Zhang, Chicago, IL (US)

(73) Assignee: The University of Chicago, Chicago, IL (US)

(*) Notice: Subject to any disclaimer, the term of this patent is extended or adjusted under 35 U.S.C. 154(b) by 354 days.

(21) Appl. No.: 15/129,853

(22) PCT Filed: Mar. 30, 2015

(86) PCT No.: PCT/US2015/023387
§ 371 (c)(1),
(2) Date: Sep. 28, 2016

(87) PCT Pub. No.: WO2015/149072
PCT Pub. Date: Oct. 1, 2015

(65) Prior Publication Data
US 2017/0182486 A1 Jun. 29, 2017

Related U.S. Application Data

(60) Provisional application No. 61/982,722, filed on Apr. 22, 2014, provisional application No. 61/971,890, filed on Mar. 28, 2014.

(51) Int. Cl.
*C07F 7/00* (2006.01)
*B01J 31/18* (2006.01)
*B01J 31/16* (2006.01)
*C07C 5/03* (2006.01)
*C07C 37/07* (2006.01)
*C07C 41/20* (2006.01)
*C07C 209/02* (2006.01)
*C07D 207/04* (2006.01)
*C07D 207/06* (2006.01)
*C07F 5/02* (2006.01)
*C07F 7/18* (2006.01)

(52) U.S. Cl.
CPC .......... *C07F 7/003* (2013.01); *B01J 31/1691* (2013.01); *B01J 31/18* (2013.01); *B01J 31/1815* (2013.01); *C07C 5/03* (2013.01); *C07C 37/07* (2013.01); *C07C 41/20* (2013.01); *C07C 209/02* (2013.01); *C07D 207/04* (2013.01); *C07D 207/06* (2013.01); *C07F 5/025* (2013.01); *C07F 7/1876* (2013.01); *B01J 2531/16* (2013.01); *B01J 2531/48* (2013.01); *B01J 2531/824* (2013.01); *B01J 2531/827* (2013.01); *B01J 2531/842* (2013.01); *B01J 2531/845* (2013.01); *B01J 2531/847* (2013.01); *Y02P 20/544* (2015.11)

(58) Field of Classification Search
CPC ...................................................... C07F 7/003
See application file for complete search history.

(56) References Cited

U.S. PATENT DOCUMENTS

| | | | |
|---|---|---|---|
| 6,878,838 | B2 | 4/2005 | Lin et al. |
| 8,653,292 | B2 | 2/2014 | Hafizovic et al. |
| 10,118,169 | B2 | 11/2018 | Lin et al. |
| 2008/0306315 | A1 | 12/2008 | Lillerud et al. |
| 2012/0115961 | A1 | 5/2012 | Hafizovic et al. |
| 2013/0210157 | A1 | 8/2013 | Chen et al. |
| 2014/0234210 | A1 | 8/2014 | Lin et al. |
| 2016/0346204 | A1 | 12/2016 | Lin et al. |
| 2017/0173572 | A1 | 6/2017 | Lin et al. |

FOREIGN PATENT DOCUMENTS

| | | |
|---|---|---|
| WO | WO 2004/084834 A2 | 10/2004 |
| WO | WO 2013/009701 | 1/2013 |
| WO | WO 2015/069926 | 5/2015 |
| WO | WO 2015/149068 A1 | 10/2015 |

OTHER PUBLICATIONS

Øien "Synthesis and characterization of modified UiO-67 metal-organic frameworks" University of Oslo, Aug. 2012.*
Almqvist et al., New Ligands for the Titanium(rv)-Induced Asymmetric Reduction of Ketones with Catecholborane**Angew. Chem.., Int. Ed., vol. 36, No. 4, pp. 376-377 (1997).
Arrowsmith et al., "Magnesium-catalysed hydroboration of aldehydes and ketones," Chem. Commun., vol. 48, pp. 4567-4569 (2012).
Beck et al., "Synthesis of Rhazinicine by a Metal-Catalyzed C—H Bond Functionalization Strategy ," Angew. Chem. Int. Ed., vol. 47, pp. 3004-3007 (2008).
Blake et al., "Enantioselective Reduction of Prochiral Ketones by Catecholborane Catalysed by Chiral Group 13 Complexes," Chem. Eur. J., vol. 6, No. 19, pp. 3586-3594 (2000).
Bruce et al., "Synthesis of a linear bis-porphyrin with a Ru(phen)22+-complexed 2,2'-bipyridine spacer ," J. Chem. Soc. Perkin Trans., vol. 1, pp. 1226-1231 (2002).
Campbell et al., "Overcoming the "Oxidant Problem": Strategies to Use O2 as the Oxidant in Organometallic C—H Oxidation Reactions Catalyzed by Pd (and Cu) ," Acc. Chem. Res., vol. 45, No. 6, pp. 851-863 (2012).

(Continued)

*Primary Examiner* — Joseph R Kosack
(74) *Attorney, Agent, or Firm* — Jenkins, Wilson, Taylor & Hunt, P.A.

(57) ABSTRACT

Metal-organic framework (MOFs) compositions based on nitrogen donor-based organic bridging ligands, including ligands based on 1,3-diketimine (NacNac), bipyridines and salicylaldimine, were synthesized and then post-synthetically metalated with metal precursors, such as complexes of first row transition metals. Metal complexes of the organic bridging ligands could also be directly incorporated into the MOFs. The MOFs provide a versatile family of recyclable and reusable single-site solid catalysts for catalyzing a variety of asymmetric organic transformations. The solid catalysts can also be integrated into a flow reactor or a supercritical fluid reactor.

15 Claims, 15 Drawing Sheets

(56) References Cited

OTHER PUBLICATIONS

Chelussi et al., "Chiral 2,2'-Bipyridines, 1,10-Phenanthrolines, and 2,2':6',2" Terpyridines:Syntheses and Applications in Asymmetric Homogeneous Catalysis," Chem. Rev., vol. 102, No. 9, pp. 3129-3170 (2002).
Cohen, Postsynthetic Methods for the Functionalization of Metal!Organic Frameworks Chem. Rev., vol. 112, pp. 970-1000 (2011).
Constable et al., "N,N'-Chelating Biheteroaromat Ligands; A Survey," Coord. Chem. Rev., vol. 93, pp. 205-223 (1989).
Das et al., "Functional mixed metal-organic frameworks with metalloligands," Angew Chem Int Ed Engl., vol. 50, pp. 10510-10520 (2011).
Dau et al., "Site-selective cyclometalation of a metal-organic framework," Chem. Sci., vol. 4, pp. 601-605 (2013).
Denmark et al., "Design and Implementation of New, Silicon-Based, Cross-Coupling Reactions: Importance of Silicon-Oxygen Bonds Scott E. Denmark," Acc. Chem. Res., vol. 35, pp. 835-846 (2002).
Dong et al., "Chiral porous organic frameworks forasymmetric heterogeneous catalysis and gas chromatographic separation," Chemical Communications, vol. 50, pp. 14949-14952 (2014).
Evans et al., "Chiral Porous Solids Based on Lamellar Lanthanide Phosphonates," J. Am. Chem. Soc., vol. 123, pp. 10395-10396 (2001).
Evans et al., "Crystal Engineering of NLO Materials Based on Metal-Organic Coordination Networks," Acc. Chem. Res., vol. 35, pp. 511-522 (2002).
Falkowski et al., "Actuation of Asymmetric Cyclopropanation Catalysts: Reversible Single-Crystal to Single-Crystal Reduction of Metal-Organic Frameworks," Angew. Chem., Int. Ed., vol. 50, pp. 8674-8678 (2011).
Falkowski et al., "Metal-Organic Frameworks as Single-Site Solid Catalysts for Asymmetric Reactions," Isr. J. Chem., vol. 52, pp. 591-603 (2012).
Falkowski et al., "Highly Stable and Porous Metal-Organic Frameworks for Asymmetric Catalysis," poster presented at the 245th ACS National Meeting, New Orleans, LA, Apr. 7-11, 1 pg. (2013).
Férey et al., "Crystallized frameworks with giant pores: are there limits to the possible?" Acc. Chem. Res., vol. 38, pp. 217-25 (2005).
Ferey et al., "Large breathing effects in three-dimensional porous hybrid matter: facts, analyses, rules and consequences," Chem. Soc. Rev., vol. 38, pp. 1380-1399 (2009).
Ford and Woodward, "Catalytic Enantioselective Reduction of Ketones by a Chiral Gallium Complex and Catecholborane," Angew. Chem., Int. Ed., vol. 38, No. 3, pp. 335-336 (1999).
Genna et al., "Heterogenization of Homogeneous Catalysts in Metal-Organic Frameworks via Cation Exchange," J. Am. Chem. Soc., vol. 135, pp. 10586-10589 (2013).
Gruning et al., "Bipyridine Periodic Mesoporous Organosilica: A Solid Ligand for the Iridium-Catalyzed Borylation of CH Bonds," Adv. Synth. Catal., vol. 356, pp. 673-679 (2014).
Holmes et al., "One-Pot Borylation/Amination Reactions: Syntheses of Arylamine Boronate Esters from Halogenated Arenes." Org. Lett., vol. 8, No. 7, pp. 1407-1410 (2006).
Hu et al., "Chiral Porous Hybrid Solids for Practical Heterogeneous Asymmetric Hydrogenation of Aromatic Ketones," J. Am. Chem. Soc., vol. 125, pp. 11490-11491 (2003).
Hu, et al., "Remarkable 4,4'-Substituent Effects on Binap: Highly Enantioselective Ru Catalysts for Asymmetric Hydrogenation of β-Aryl Ketoesters and Their Immobilization in Room-Temperature Ionic Liquids," Angew. Chem. Int. Ed., vol. 43, pp. 2501-2504 (2004).
Ihara et al., Easily Attachable and Detachable ortho-Directing Agent for Arylboronic Acids in Ruthenium-Catalyzed Aromatic C—H Silylation J. Am. Chem. Soc., vol. 131, No. 22, pp. 7502-7503 (2009).
Ishiyama et al., "Mild Iridium-Catalyzed Borylation of Arenes. High Turnover Numbers, Room Temperature Reactions, and Isolation of a Potential Intermediate," J. Am. Chem. Soc., vol. 124, No. 3, pp. 390-391 (2001).
Ishiyama et al., "A stoichiometric aromatic CbondH borylation catalyzed by iridium(i)/2,2'-bipyridine complexes at room temperature.," Angew. Chem., Int. Ed., vol. 41, No. 16, pp. 3056-3058 (2002).
Iverson et al., "Stoichiometric and Catalytic B—C Bond Formation from Unactivated Hydrocarbons and Boranes," J. Am. Chem. Soc., vol. 121, pp. 7696-7697 (1999).
Izawa et al., "Aerobic Oxidative Heck/Dehydrogenation Reactions of Cyclohexenones: Efficient Access to meta-Substituted Phenols," Angew. Chem. Int. Ed., vol. 52, pp. 3672-3675 (2013).
Jang et al., "Rhodium-catalyzed reductive cyclization of 1,6-diynes and 1,6-enynes mediated by hydrogen: catalytic C—C bond formation via capture of hydrogenation intermediates," J. Am. Chem. Soc., vol. 126, pp. 7875-7880 ( 2004).
Jang et al., "Enantioselective Reductive Cyclization of 1,6-Enynes via Rhodium-Catalyzed Asymmetric Hydrogenation: C—C Bond Formation Precedes Hydrogen Activation," J. Am. Chem. Soc., vol. 127, pp. 6174-6175 (2005).
Jones et al., "The Oxidation of the Carbon-Silicon Bond," Tetrahedron, vol. 52, No. 22, pp. 7599-7662 (1996).
Karnahl et al., "Synthesis and Photophysical Properties of 3,8-Disubstituted 1,10-Phenanthrolines and Their Ruthenium(II) Complexes." Eur. J. Inorg. Chem., pp. 4962-4971 (2009).
Kawamorita et al., "Directed Ortho Borylation of Functionalized Arenes Catalyzed by a Silica-Supported Compact Phosphine-Iridium System," J. Am. Chem. Soc., vol. 131, pp. 5058-5059 (2009).
Kesanli et al., "Chiral porous coordination networks: rational design and applications in enantioselective processes," Coord. Chem. Rev., vol. 246, pp. 305-326 (2003).
Khalimon et al., "Catalytic hydroboration by an imido-hydrido complex of Mo(IV)," Chem. Commun., vol. 48, pp. 455-457 (2012).
Kikuchi et al., "Practical synthesis of pinacolborane for one-pot synthesis of unsymmetrical biaryls via aromatic C—H borylation-cross-coupling sequence," Tetrahedron, vol. 64, pp. 4967-4971 (2008).
Kitagawa et al., "Functional Porous Coordination Polymers," Angew. Chem. Int. Ed. Engl, vol. 43, pp. 2334-2375 (2004).
Kong et al., "Assembly and Post-Modification of a Metal-Organic Nanotube for Highly Efficient Catalysis," J. Am. Chem. Soc., vol. 134, pp. 19851-19857 (2012).
Koren-Selfridge et al., A Boron-Substituted Analogue of the Shvo Hydrogenation Catalyst: Catalytic Hydroboration of Aldehydes, Imines, and Ketones, Organomettalics, vol. 28, 2085 (2009).
Kudo et al., "A Versatile Method for Suzuki Cross-Coupling Reactions of Nitrogen Heterocycles," Angew. CHem., Int. Ed., vol. 45, No. 8, pp. 1282-1284 (2006).
Kusaka et al., "meso-Alkynyl BODIPYs: Structure, Photoproperties, π-Extension, and Manipulation of Frontier Orbitals," Chem. Asian J., vol. 8, pp. 723-727 (2013).
Li et al., "Metal-organic frameworks for separations," Chem Rev, vol. 112, pp. 869-932 (2012).
Li et al., Iridium-Catalyzed Regioselective Silylation of Aromatic and Benzylic C—H Bonds Directed by a Secondary AmineAngew. Chem., Int. Ed., vol. 53, 8471 (2014).
Lindsley et al., "Metal Alkoxide Catalysis of Catecbolborane and Borane Reductions Medlanistie Studies.," Tetrahedron Letters, vol. 35, No. 29, pp. 5141-5144 (1994).
Locatelli et al., "Effective Modular Iminooxazoline (IMOX) Ligands for Asymmetric Catalysis : [Zn(IMOX)]-Promoted Enantioselective Reduction of Ketones by Catecholborane," Angew. Chem., Int. Ed., vol. 42, pp. 4928-4930 (2003).
Love et al., "Preparation of N-Tosylaldimines," Synlett, pp. 493-494 (Jul. 1994).
Ma et al., "A series of isoreticular chiral metal-organic frameworks as a tunable platform for asymmetric catalysis," Nature Chemistry, vol. 2, pp. 838-846 (Oct. 2010).

(56) References Cited

OTHER PUBLICATIONS

Maleczka et al., "C—H Activation/Borylation/Oxidation: A One-Pot Unified Route to Meta-Substituted Phenols Bearing Ortho-/Para-Directing Groups," J. Am. Chem. Soc., vol. 125, pp. 7792-7793 (2003).
Manna et al., "Salicylaldimine-Based Metal-Organic Framework Enabling Highly Active Olefin Hydrogenation with Iron and Cobalt Catalysts," J. Am. Chem. Soc., vol. 136, 13182-13185 (2014).
Mazzacano et al., "Base Metal Catalysts for Photochemical C—H Borylation That Utilize Metal-Metal Cooperativity." J. Am. Chem. Soc., vol. 135, pp. 17258-17261 (2013).
Mkhalid et al., "C—H Activation for the Construction of C—B Bonds," Chem. Rev., vol. 110, pp. 890-931 (2010).
Morimoto et al., "CO-Transfer Carbonylation Reactions. A Catalytic Pauson-Khand-Type Reaction of Enynes with Aldehydes as a Source of Carbon Monoxide," J. Am. Chem. Soc., vol. 124, pp. 3806-3807 (2002).
Moulton et al., "From molecules to crystal engineering: supramolecular isomerism and polymorphism in network solids," Chem Rev., vol. 101, pp. 1629-1658 (2001).
Mukherjee et al., "Magnesium-catalyzed hydroboration of esters: evidence for a new zwitterionic mechanism," Chemical Science, vol. 5, pp. 959-964 (2014).
Newkome et al., "Synthesis of 2,2'-Bipyridines: Versatile Building Blocks for Sexy Architectures and Functional Nanomaterials," Eur. J. Org. Chem., pp. 235-254 (2004).
Nickerl et al., "Integration of accessible secondary metal sites into MOFs for H2S removal," Inorga. Chem. Front., vol. 1, pp. 325-330 (2014).
Noyori, et al, "Asymmetric Hydrogenation of β-Keto Carboxylic Esters. A Practical, Purely Chemical Access to β-Hydroxy Esters in High Enantiomeric Purity," J. Am. Chem. Soc., vol. 109, pp. 5856-5858 (1987).
Noyori, et al., "BINAP: An Efficient Chiral Element for Asymmetric Catalysis," Ace. Chem. Res., vol. 23, pp. 345-350 (1990).
Noyori, "Asymmetric Catalysis: Science and Opportunities (Nobel Lecture)," Chem., Int. Ed. 2002, vol. 41, pp. 2008-2022 (2002).
Obligacion et al., "Cobalt-Catalyzed C—H Borylation," J. Am. Chem. Soc., vol. 136, pp. 4133-4136 (2014).
Ohta, et al, "Asymmetric Hydrogenation of Unsaturated Carboxylic Acids Catalyzed by BINAP-Ruthenium(II) Complexes," J. Org. Chem., vol. 52, No. 14, pp. 3174-3178 (1987).
Okamoto et al., "Electronic and steric tuning of chiral diene ligands for rhodium-catalyzed asymmetric arylation of imines," Chem. Commun., No. 32, pp. 4815-4817 (Aug. 28, 2009).
Pattison et al., "Enantioselective Rhodium-Catalyzed Addition of Arylboronic Acids to Alkenylheteroarenes," J. Am. Chem. Soc., vol. 132, pp. 14373-14375 (2010).
Preshlock et al., "High-Throughput Optimization of Ir-Catalyzed C—H Borylation: A Tutorial for Practical Applications," J. Am. Chem. Soc., vol. 135, pp. 7572-758 (2013).
Sarvary, et al., "Asymmetric reduction of ketones with catecholborane using 2,6-BODOL complexes of titanium(IV) as catalysts", Chem. Eur. J., vol. 7, No. 10, pp. 2158-2166 (2001).
Schaate et al., "Porous Interpenetrated Zirconium-Organic Frameworks (PIZOFs): A Chemically Versatile Family of Metal-Organic Frameworks," Chem. Eur. J., vol. 17, pp. 9320-9325 (2011).
Shibata et al., "Catalytic Pauson-Khand-Type Reaction Using Aldehydes as a CO Source," Org. Lett., vol. 4, No. 9, pp. 1619-1621 (2002).
Shibata et al., "Rhodium Complex-Catalyzed Pauson-Khand-Type Reaction With Aldehydes as a CO Source," J Org Chem, vol. 67, pp. 7446-7450 (2002).
Shustova et al., "Selective turn-on ammonia sensing enabled by high-temperature fluorescence in metal-organic frameworks with open metal sites," J Am Chem Soc, vol. 135, pp. 13326-13329 (2013).
Siewert, et al, "Rhodium-Catalyzed Enantioselective 1,2-Addition of Aluminum Organyl Compounds to Cyclic Enones," Angew. Chem.lnt. Ed., vol. 46, pp. 7122-7124 (2007).

Song et al., "Isoreticular chiral metal-organic frameworks for asymmetric alkene epoxidation: tuning catalytic activity by controlling framework catenation and varying open channel sizes," J Am Chem Soc, vol. 132, pp. 15390-15398 (2010).
Tagata et al., "Continuous-Flow C—H Borylation of Arene Derivatives," Adv. Synth. Catal., vol. 352, pp. 1662-1666 (2010).
Takaya, et al., Rhodium-Catalyzed Asymmetric 1,4-Addition of Aryl- and Alkenylboronic Acids to Enones, Am. Chem. Soc., vol. 120, pp. 5579-5580 (1998).
Tanabe et al., "Stabilizing unstable species through single-site isolation: A catalytically active TaV trialkyl in a porous organic polymer," Chem. Sci., vol. 4, pp. 2483-2489 (2013).
Tanaka et al., "A novel chiral porous metal-organic framework: asymmetric ring opening reaction of epoxide with amine in the chiral open space," Chem. Commun., pp. 820-822 (2008).
Torbati et al., "Dichlorido(6,6'-dimethyl-2,2'-bipyridine-K2N,N')cobalt(II)," Acta Crystallographica, vol. E66, pp. m1284 plus supporting information (7 pages total) (2010).
Wang et al., "Elucidating Molecular Iridium Water Oxidation Catalysts Using Metal-Organic Frameworks: A Comprehensive Structural, Catalytic, Spectroscopic, and Kinetic Study," J. Am. Chem. Soc., vol. 134, pp. 19895-19908 (2012).
Wu et al., "A homochiral porous metal-organic framework for highly enantioselective heterogeneous asymmetric catalysis," J Am Chem Soc, vol. 127, pp. 8940-8941 (2005).
Wu et al., "Recyclable Silica-Supported Iridium Bipyridine Catalyst for Aromatic C—H Borylation," ACS Catal. pp. 1365-1375 (2014).
Yoon, et al., "Privileged Chiral Catalysts," Science, vol. 299, pp. 1691-1693 (Mar. 14 2003).
Yoon et al., "Homochiral metal-organic frameworks for asymmetric heterogeneous catalysis," Chem Rev, vol. 112, pp. 1196-1231 (2012).
Zheng et al., "Cavity-induced enantioselectivity reversal in a chiral metal-organic framework Brønsted acid catalyst," Chem. Sci., vol. 3, pp. 2623-2627 (2012).
Zhou, et al., "BINAP", Privileged Chiral Ligands and Catalysts; Wiley-VCH: Weinheim, Germany, pp. 1-53 (2011).
Zhu et al., "Chiral Nanoporous Metal-Metallosalen Frameworks for Hydrolytic Kinetic Resolution of Epoxides," J. Am. Chem. Soc., vol. 134, pp. 8058-8061 (2012).
Balskus, "Chiral Diene-Metal Complexes in Asymmetric Catalysis," F. Angew. Chem., Int. Ed., vol. 43, pp. 1-4 (2004).
Bloch et al., "Metal Insertion in a Microporous Metal-Organic Framework Lined with 2,2'-Bipyridine", J. Am. Chem. Soc., vol. 132, pp. 14382-14384 (Sep. 17, 2010).
Cavka et al., "A New Zirconium Inorganic Building Brick Forming Metal Organic Frameworks with Exceptional Stability," J. Am. Chem. Soc., vol. 130, No. 42, pp. 13850-13851 (2008).
Cho et al., "Remarkably selective iridium catalysts for the elaboration of aromatic C—H bonds," Science, vol. 295, No. 5553, pp. 305-308 (Jan. 11, 2002).
Cho et al., "A metal-organic framework material that functions as an enantioselective catalyst for olefin epoxidation," Chem. Commun., pp. 2563-2565 (2006).
Falkowski et al., "Privileged phosphine-based metal-organic frameworks for broad-scope asymmetric catalysis," Journal of the American Chemical Society, vol. 136, No. 14, pp. 5213-5216 (Mar. 31, 2014).
Fei et al., "A robust, catalytic metal-organic framework with open 2,2'-bipyridine sites," Chemical Communications, vol. 50, pp. 4810-4812 (published online Mar. 21, 2014).
Furukawa, et al., "The Chemistry and Applications of Metal-Organic Frameworks," Science, vol. 341, pp. 974-986 (Aug. 30, 2013).
Hadlington et al., "Low Coordinate Germanium(II) and Tin(II) Hydride Complexes: Efficient Catalysts for the Hydroboration of Carbonyl Compounds," J. Am. Chem. Soc., vol. 136, pp. 3028-3031 (Feb. 2014).
Hartwig, "Borylation and Silylation of C—H Bonds: A Platform for Diverse C—H Bond Functionalizations," Acc. Chem. Res., vol. 45, No. 6, pp. 864-873 (2012).

(56) References Cited

OTHER PUBLICATIONS

Hayashi et al., "Rhodium-catalyzed asymmetric 1,4-addition and its related asymmetric reactions.," Chem. Rev., vol. 103, No. 8, pp. 2829-2844 (2003).
He et al., "Nanoscale Metal-Organic Frameworks for the Co-delivery of Cisplatin and Pooled siRNAs to Enhance Therapeutic Efficacy in Drug-resistant Ovarian Cancer Cells," J. Am. Chem. Soc., vol. 136, 5181-5184 (2014).
Horcajada et al., "Metal-organic frameworks in biomedicine"m Chem. Rev. vol. 112, No. 8, pp. 1232-1268 (2012).
Hu et al., "Chiral, porous, hybrid solids for highly enantioselective heterogeneous asymmetric hydrogenation of beta-keto esters," Angewandte Chemie International Ed. vol. 42, pp. 6000-6003 (2003).
Izawa et al., Science, "Palladium-Catalyzed Aerobic Dehydrogenation of Substituted Cyclohexanones to Phenols," vol. 333, 209-213 (Jul. 8, 2011).
Kaes et al., "Bipyridine: the most widely used ligand. A review of molecules comprising at least two 2,2'-bipyridine units.," Chem. Rev., vol. 100, pp. 3553-3590 (Oct. 11, 2000).
Kandiah et al., "Synthesis and Stability of Tagged UiO-66 Zr-MOFs," Chem. Mater., vol. 22, No. 24, pp. 6632-6640 (2010).
Kreno et al., "Metal Organic Framework Materials as Chemical Sensors," Chem. Rev., vol. 112, pp. 1105-1125 (2012).
Lan et al., "A luminescent microporous metal-organic framework for the fast and reversible detection of high explosives," Angew Chem Int Ed Engl, vol. 48, pp. 2334-2338 (2009).
Lee et al., "Metal-organic framework materials as catalysts," Chem. Soc. Rev., vol. 38, 1450-1459 (2009).
Li et al., "Design and synthesis of an exceptionally stable and highly porousmetal-organic framework," Nature, vol. 402, 276-279 (Nov. 18, 1999).
Li et al., "High gas storage capacities and stepwise adsorption in a UiO type metal-organic framework incorporating Lewis basic bipyridyl sites," Chemical Communications, vol. 50, pp. 2304-2307 (2014).
Lau et al., "PLUXter: Rapid discovery of metal organic framework structures using PCA and HCA of high throughput synchrotron powder diffraction data," Combinatorial Chem. & High Throughput Screening, vol. 14, pp. 28-35 (2011).
Ma et al., "Enantioselective catalysis with homochiral metal-organic frameworks," Chemical Society Reviews, vol. 38, No. 5, pp. 1248-1256 (Feb. 23, 2009).
Manna et al., "Postsynthetic metalation of bipyridyl-containing metal-organic frameworks for highly efficient catalytic organic transformations," J. Am. Chem. Soc., vol. 136, pp. 6566-6569 (Apr. 23, 2014).
Miyashita, et al., "Synthesis of 2,2'-bis(diphenylphosphino)-1,1'-binaphthyl (BINAP), an atropisomeric chiral bis(triaryl)phosphine, and its use in the rhodium(I)-catalyzed asymmetric hydrogenation of .alpha.-(acylamino)acrylic acids," J. Am. Chem. Soc., vol. 102, No. 27, pp. 7932-7934 (Dec. 1980).
Miyaura et al., "Palladium-Catalyzed Cross-Coupling Reactions of Organoboron Compounds," Chem. Rev., vol. 95, pp. 2457-2483 (1995).
Murphy et al., "Meta Halogenation of 1,3-Disubstituted Arenes via Iridium-Catalyzed Arene Borylation," J. Am. Chem. Soc., vol. 129, pp. 15434-15435 (2007).
Notification Concerning Transmittal of Copy of International Preliminary Report on Patentability (Chapter I of the Patent Cooperation Treaty) corresponding to PCT/US2015/023331 dated Oct. 13, 2016.
Notification Concerning Transmittal of Copy of International Preliminary Report on Patentability (Chapter I of the Patent Cooperation Treaty) corresponding to PCT/US2015/023387 dated Oct. 13, 2016.
Notification of Transmittal of the International Search Report and the Written Opinion of the International Searching Authority, or the Declaration corresponding to PCT/US2015/023331 dated Jul. 7, 2015.
Notification of Transmittal of the International Search Report and the Written Opinion of the International Searching Authority, or the Declaration corresponding to PCT/US2015/023387, dated Jun. 24, 2015.
Oluyadi et al., "Titanocene(II)-Catalyzed Hydroboration of Carbonyl Compounds," Organometallics, vol. 32, pp. 70-78 (2012).
Ravel et al., "Athena, Artemis, Hephaestus: data analysis for X-ray absorption spectroscopy using IFEFFIT," Jour. Synchrotron Radiation, vol. 12, pp. 537-541 (2005).
Rehr, "Theoretical approaches to x-ray absorption fine structure," Rev. Mod. Phys., vol. 72, No. 3, p. 621-654 (Jul. 2000).
Roosen et al., "Outer-Sphere Direction in Iridium C—H Borylation," J. Am. Chem. Soc., vol. vol. 134, No. 28, pp. 11350-11353 (Jul. 18, 2012).
Saitoh et al., "Preparation of symmetric dibromides of 1,10-phenanthroline," Can. J. Chem., vol. 75, pp. 1336-1339 (1997).
Sawano et al., "Chiral Diene-Based Metal-Organic Frameworks for Highly Enantioselective Carbon-Carbon Bond Formation Reactions," Chem. Sci., 6, pp. 1-6 (2015).
Sawano et al., "Robust, Chiral, and Porous BINAP-Based Metal-Organic Frame-works for Highly Enantioselective Cyclization Reactions", J.Am. Chem. Soc., vol. 137, pp. 12241-12248 (Sep. 2015).
Schaate et al., "Modulated Synthesis of Zr-Based Metal-Organic Frameworks: From Nano to Single Crystals," Chemistry—A European Journal, vol. 17, pp. 6643-6651 (2011).
Schwab et al., "Preparation of 5-Brominated and 5,5'-Dibrominated 2,2'-Bipyridines and 2,2'-Bipyrimidines," J. Org. CHem., vol. 67, No. , pp. 443-449 (2002).
Sheldrick, Acta Crystallographica Section A, vol. 64, 112-122 (2008).
Sigman et al., "Imparting catalyst control upon classical palladium-catalyzed alkenyl C—H bond functionalization reactions," Acc. Chem. Res., vol. 45, No. 6, pp. 874-884 (2012).
Simmons et al., "Iridium-Catalyzed Arene Ortho-Silylation by Formal Hydroxyl-Directed C—H Activation," J. Am. CHem. Soc., vol. 132, No. 48, pp. 17092-17095 (Nov. 15, 2010).
Sheldrick, "A short history of SHELX," Acta Cryst., vol. A64, pp. 112-122 (2008).
Song et al., "Chiral porous metal-organic frameworks with dual active sites for sequential asymmetric catalysis," Proc. R. Soc., vol. 468, pp. 2035-2058 (Mar. 14, 2012).
Suh et al., "Hydrogen Storage in Metal-Organic Frameworks," Chem. Rev., vol. 112, No. 2, pp. 782-835 (2012).
Sumida et al., "Carbon dioxide capture in metal-organic frameworks," Chem. Rev., vol. 112, pp. 724-81 (2012).
Tamao et al., "Hydrogen Peroxide Oxidation of the Silicon-Carbon Bond in Organoaikoxysiiane." Organometallics, vol. 2, No. 11, 1694-1696 (1983).
Tzschucke et al., "Arenes to Anilines and Aryl Ethers by Sequential Iridium-Catalyzed Borylation and Copper-Catalyzed Coupling", Organic Letters, vol. 9, No. 5, pp. 761-764 (2007).
Uemura et al., "Polymerization reactions in porous coordination polymers," Chem. Rev., vol. 38, No. 5, pp. 1-9 (2009).
Wan, et al., "Cross-coupling of remote meta-C—H bonds directed by a U-shaped template," J. Am. Chem. Soc., vol. 135, 18056-18059 (2013).
Wang et al., "Doping metal-organic frameworks for water oxidation, carbon dioxide reduction, and organic photocatalysis.," J. Am. Chem. Soc., vol. 133, No. 34, pp. 13445-13454 (2011).
Wang et al., "Metal-organic Frameworks as a Tunable Platform for Designing Functional Molecular Materials," J. Am. Chem. Soc., vol. 135, No. 36, pp. 1-32 (Sep. 11, 2013).
Wiers et al., "A solid lithium electrolyte via addition of lithium isopropoxide to a metal-organic framework with open metal sites," J Am Chem Soc, vol. 133, No. 37, pp. 14522-14525 (Aug. 30, 2011).
Yinghuai et al., "Catalytic Phenylborylation Reaction by Iridium(0) Nanoparticles Produced from Hydridoiridium Carborane," Inorg. Chem., vol. 47, No. 13, pp. 5756-5761 (2008).
Office Action corresponding to U.S. Appl. No. 15/129,851 dated Mar. 1, 2018.
Office Action corresponding to U.S. Appl. No. 15/129,851 dated Aug. 25, 2017.

(56) References Cited

OTHER PUBLICATIONS

Notice of Allowance and Interview Summary corresponding to U.S. Appl. No. 15/129,851 dated Jul. 2, 2018.
Office Action (Restriction Requirement) corresponding to U.S. Appl. No. 15/129,851 dated May 2, 2017.

* cited by examiner

METAL-ORGANIC FRAMEWORKS CONTAINING NITROGEN-DONOR LIGANDS FOR EFFICIENT CATALYTIC ORGANIC TRANSFORMATIONS

RELATED APPLICATIONS

The presently disclosed subject matter claims the benefit of U.S. Provisional Patent Application Ser. No. 61/971,890, filed Mar. 28, 2014; and of U.S. Provisional Patent Application Ser. No. 61/982,722, filed Apr. 22, 2014, the disclosures of each of which are incorporated herein by reference in their entireties.

STATEMENT OF GOVERNMENT SUPPORT

This invention was made with government support under Grant No. CHE-1111490 from the National Science Foundation. The government has certain rights to this invention.

TECHNICAL FIELD

The presently disclosed subject matter relates to metal-organic framework (MOF) materials containing organic bridging ligands containing nitrogen donors, such as bipyridine, phenanthroline, terpyridine, salcylaldimine, pyridylphenol, 1,3-diketimine (NacNac), and bis(oxazoline), their preparation, and their use as heterogeneous catalysts for organic transformations, such as the borylation of substituted cyclohexenones, the hydrogenation of olefins and ketones, hydrosilation, hydroboration, carbon-carbon bond coupling reactions, and others.

ABBREVIATIONS

Å=angstrom
° C.=degrees Celsius
%=percentage
μL=microliter
μmol=micromole
acac=acetylacetonate
Ar=aryl
atm=atmosphere
BINOL=1,1'-bi-2-naphthol
BPY=bipyridine
cod=cyclooctadiene
d=day
DCE=dichloroethane
DMF=dimethylformamide
DMSO=dimethylsulfoxide
e.e. (or ee)=enantiomeric excess
EtOH=ethanol
EXFAS=extended x-ray absorption fine structure
g=gram
GC=gas chromatography
h=hour
HPLC=high performance liquid chromatography
ICP-MS=inductively coupled plasma-mass spectrometry
kg=kilogram
mg=milligram
min=minute
mL=milliliter
mM=millimolar
mmol=millimole
MOF=metal-organic framework
mol=mole
nbd=norbornadiene
nm=nanometer
NMOF=nano-metal-organic frameworks
NMR=nuclear magnetic resonance
Ph=phenyl
pin=pinacolate
PXRD=power x-ray diffraction
r.t.=room temperature
SBU=secondary building unit
TEM=transmission electron microscopy
TFA=trifluoroacetic acid
TGA=thermogravimetric analysis
TLC=thin layer chromatography
TON=turn over number
XAFS=x-ray absorption fine structure spectroscopy
XANES=x-ray absorption near edge structure

BACKGROUND

Metal-organic frameworks (MOFs) are an emerging class of porous molecular materials (see Moulton et al., Chem. Rev., 2001, 101, 1629; Evans et al., Acc. Chem. Res., 2002, 35, 511; Lan et al., Angew. Chem., Int. Ed., 2009, 48, 2334; Uemura et al., Chem. Soc. Rev., 2009, 38, 1228; Das et al., Angew. Chem., Int. Ed., 2011, 50, 10510; Wiers et al., J. Am. Chem. Soc., 2011, 133, 14522; Kreno et al., Chem. Rev., 2012, 112, 1105; Li et al., Chem. Rev., 2012, 112, 869; Furukawa et al., Science, 2013, 341; and Shustova et al., J. Am. Chem. Soc., 2013, 135, 13326) assembled from organic linkers and metal ions or metal cluster nodes. They find application in gas storage (e.g., hydrogen, carbon dioxide, and methane storage), molecule separation, and drug delivery. MOFs can also provide a highly tunable platform to engineer heterogeneous catalysts for chemical reactions, including asymmetric organic transformations and/or transformations that cannot be achieved with traditional porous inorganic materials. See Kesanli et al., Coord. Chem. Rev., 2003, 246, 305.

Some asymmetric MOF catalysts have been reported that can provide enantio-differentiation. See Ma et al., Chem. Soc. Rev., 2009, 38, 1248; Falkowski et al., Isr. J. Chem., 2012, 52, 591; and Yoon et al., Chem. Rev., 2012, 112, 1196. The first MOF catalyst with significant enantiomeric excesses (e.e.'s) contained the $C_2$-symmetric 1,1'-bi-2-naphthol (BINOL). See Evans et al., J. Am. Chem. Soc., 2001, 123, 10395; and Wu et al., J. Am. Chem. Soc., 2005, 127, 8940. The postsynthetically-generated Ti-BINOLate moiety in the chiral MOF was responsible for high e.e.'s observed for diethylzinc additions to aromatic aldehydes. See Wu et al., J. Am. Chem. Soc., 2005, 127, 8940. Subsequently, a Mn-salen-based MOF was used for the asymmetric epoxidation of alkenes. See Cho et al., Chem. Commun. 2006, 2563. Since these reports, additional stereoselective MOF catalysts have been developed based on BINOL- and salen-based ligands. See Tanaka et al., Chem. Commun., 2008, 820; Ma et al., Nat. Chem., 2010, 2, 838; Song et al., J. Am. Chem. Soc., 2010, 132, 15390; Falkowski et al., Angew. Chem., Int. Ed., 2011, 50, 8674; Zheng et al., Chem. Sci., 2012, 3, 2623; and Shu et al., J. Am. Chem. Soc., 2012, 134, 8058.

However, there remains an ongoing need in the art for additional heterogeneous catalysts for catalysis. In particular, there is an ongoing need for additional catalysts that have good efficiency and/or that have good stability and recyclability and/or that are based on earth abundant metals such as V, Cr, Mn, Fe, Co, Ni, and Cu. For example, there is an ongoing need for additional heterogeneous catalysts that can catalyze reactions at low catalyst loadings. There is also a need for additional asymmetric heterogeneous catalysts to catalyze additional types of enantioselective reactions.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

Disclosed herein in some embodiments is a method for preparing a crystalline and/or porous metal-organic framework (MOF). In some embodiments, the crystalline and/or porous MOF comprises periodic repeats of a metal-based secondary building unit (SBU) and a nitrogen donor-based bridging ligand. In some embodiments, the method comprises providing a nitrogen donor-based bridging ligand; and contacting the nitrogen donor-based bridging ligand with a first metal source to obtain a crystalline and/or porous MOF.

In some embodiments, the nitrogen donor-based bridging ligand is a derivative of one of the nitrogen donor moieties selected from the group comprising bipyridines, phenanthrolines, terpyridines, salicylaldimines, pyridylphenols, 1,3-diketimine (NacNac), and bis(oxazolines). In some embodiments, the nitrogen donor-based bridging ligand is a derivative of a nitrogen donor moiety, wherein the nitrogen donor moiety is substituted by one or more substituents comprising a carboxylate, pyridine, and/or phosphonate moiety. In some embodiments, the nitrogen donor-based bridging ligand is a dicarboxylate, a tricarboxylate, a tetracarboxylate, a bipyridine, a tripyridine, a tetrapyridine, a diphosphonate, a triphosphonate, or a tetraphosphonate derivative of a nitrogen donor moiety. In some embodiments, the nitrogen donor-based bridging ligand is a nitrogen donor moiety substituted with at least two substituents selected from the group comprising carboxylate, pyridine, and phosphonate.

In some embodiments, the nitrogen donor-based bridging ligand is a carboxylate, pyridine, or phosphonate derivative of a nitrogen donor moiety selected from the group comprising bipyridines, phenanthrolines, terpyridines, salicylaldimines, pyridylphenols, and bis(oxazolines). In some embodiments, the nitrogen donor-based bridging ligand is a dicarboxylate-substituted bipyridine, phenanthroline, terpyridine, salicylaldimine, pyridylphenol, 1,3-diketimine (NacNac), or bis(oxazoline). In some embodiments, the nitrogen-donor based bridging ligand is not a derivative of an N,N'-alkylenebis(salicylimine) or a derivative of an N,N'-arylenebis(salicylimine). In some embodiments, the nitrogen-donor-based bridging ligand is a chiral bridging ligand.

In some embodiments, the SBU is selected from the group comprising Hf-oxo clusters, Zr-oxo clusters, Zn-oxo clusters, Ti-oxo clusters, Cu-carboxylate paddlewheels, and other SBUs used to construct MOFs. In some embodiments, the first metal source is a metal alkoxide or a metal halide. In some embodiments, the first metal source is $ZrCl_4$.

In some embodiments, the method further comprises contacting the crystalline and porous MOF with a second metal source to metalate the bridging ligand. In some embodiments, the second metal source comprises Fe, Co, Ni, Rh, Ru, Ir, Os, Pt, Pd, V, Cr, Mn or Cu. In some embodiments, the second metal source is $FeCl_3$, $CoCl_2$, $NiCl_2$.

In some embodiments, the MOF further comprises a bridging ligand that is not a nitrogen donor-based bridging ligand. In some embodiments, the nitrogen donor-based bridging ligand and the first metal source are contacted in a solvent or mixture of solvents selected based on solvent molecule size, such that the sizes and/or shapes of internal pores, cavities, and/or open channels in the crystalline and porous MOF can be tailored to enhance catalytic activity and selectivity.

In some embodiments, disclosed is a heterogeneous catalyst comprising a crystalline and porous MOF, wherein said crystalline and porous MOF comprises periodic repeats of a metal-based secondary building unit (SBU), wherein said metal-based SBU comprises a first metal, and a nitrogen donor-based bridging ligand, wherein said nitrogen donor-based bridging ligand is further complexed to a second metal. In some embodiments, the heterogeneous catalyst is prepared according to any of the methods disclosed herein.

In some embodiments, disclosed is a method for preparing a compound comprising contacting a substrate capable of forming a product by catalytic transformation with a heterogeneous catalyst as disclosed herein. In some embodiments, the catalytic transformation is selected from the group comprising hydrogenation; dehydrogenation; isomerization, optionally the isomerization of an allylamine, an allyl alcohol, or an $\alpha,\beta$-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an $\alpha$-substitution reaction, optionally wherein the $\alpha$-substitution reaction is a protonation, a fluorination, an amination, an arylation, or an orthoester alkylation; an ene reaction; a Diels-Alder reaction; a Pauson-Khand reaction; an enyne intramolecular cyclization; a [2+2+2] cycloaddition; a [3+2] cycloaddition; and a ring-opening reaction.

Accordingly, it is an object of the presently disclosed subject matter to provide metal-organic framework (MOFs) materials comprising nitrogen donor-based bridging ligands, as well as methods of making and using the MOFs as heterogeneous catalysts for organic transformations. This and other objects are achieved in whole or in part by the presently disclosed subject matter.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). A further understanding of the presently disclosed subject matter can be obtained by reference to an embodiment set forth in the illustrations of the accompanying drawings. Although the illustrated embodiment is merely exemplary of the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, but merely to clarify and exemplify the presently disclosed subject matter.

For a more complete understanding of the presently disclosed subject matter, reference is now made to the following drawings in which.

DETAILED DESCRIPTION

Figure 1B:
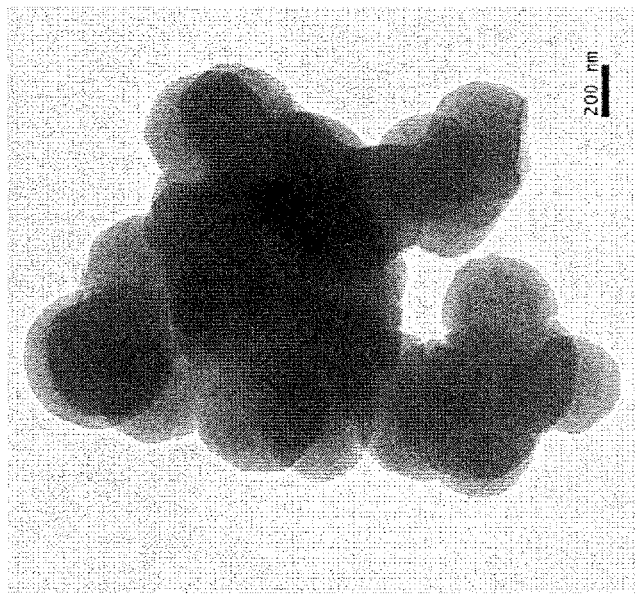
FIG. 1B is a transmission electron microscopy (TEM) image of the metal-organic framework (MOF) described in FIG. 1A. The scale bar in the lower right-hand corner represents 200 nanometers (nm).

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. Although any methods, devices, and materials similar or equivalent to those described herein can be used in the practice or testing of the presently disclosed subject matter, representative methods, devices, and materials are now described. All publications, patent applications, patents, and other references mentioned herein are incorporated by reference in their entirety.

Throughout the specification and claims, a given chemical formula or name shall encompass all optical and stereoisomers, as well as racemic mixtures where such isomers and mixtures exist.

I. Definitions

While the following terms are believed to be well understood by one of ordinary skill in the art, the following definitions are set forth to facilitate explanation of the presently disclosed subject matter.

Following long-standing patent law convention, the terms "a", "an", and "the" refer to "one or more" when used in this application, including the claims. Thus, for example, reference to "a metal ion" includes a plurality of such metal ions, and so forth.

Unless otherwise indicated, all numbers expressing quantities of size, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value or to an amount of size (i.e., diameter), weight, concentration or percentage is meant to encompass variations of in one example ±20% or ±10%, in another example ±5%, in another example ±1%, and in still another example ±0.1% from the specified amount, as such variations are appropriate to perform the disclosed methods.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "comprising", which is synonymous with "including," "containing," or "characterized by" is inclusive or open-ended and does not exclude additional, unrecited elements or method steps. "Comprising" is a term of art used in claim language which means that the named elements are present, but other elements can be added and still form a construct or method within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein the term "alkyl" can refer to $C_{1-20}$ inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. In some embodiments, there can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Heteroaryl" as used herein refers to an aryl group that contains one or more non-carbon atoms (e.g., O, N, S, Se, etc) in the backbone of a ring structure. Nitrogen-containing heteroaryl moieties include, but are not limited to, pyridine, imidazole, benzimidazole, pyrazole, pyrazine, triazine, pyrimidine, and the like.

"Aralkyl" refers to an -alkyl-aryl group, optionally wherein the alkyl and/or aryl moiety is substituted.

"Alkylene" refers to a straight or branched bivalent aliphatic hydrocarbon group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH$_2$—); ethylene (—CH$_2$—CH$_2$—); propylene (—(CH$_2$)$_3$—); cyclohexylene (—C$_6$H$_{10}$—); —CH=CH—CH=CH—; —CH=CH—CH$_2$—; —(CH$_2$)$_q$—N(R)—(CH$_2$)$_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—CH$_2$—O—); and ethylenedioxy (—O—(CH$_2$)$_2$—O—). An alkylene group can have about 2 to about 3 carbon atoms and can further have 6-20 carbons.

The term "arylene" refers to a bivalent aromatic group, e.g., a bivalent phenyl or napthyl group. The arylene group can optionally be substituted with one or more aryl group substituents and/or include one or more heteroatoms.

The term "amino" refers to the group —N(R)$_2$ wherein each R is independently H, alkyl, substituted alkyl, aryl, substituted aryl, aralkyl, or substituted aralkyl. The terms "aminoalkyl" and "alkylamino" can refer to the group —N(R)$_2$ wherein each R is H, alkyl or substituted alkyl, and wherein at least one R is alkyl or substituted alkyl. "Arylamine" and "aminoaryl" refer to the group —N(R)$_2$ wherein each R is H, aryl, or substituted aryl, and wherein at least one R is aryl or substituted aryl, e.g., aniline (i.e., —NHC$_6$H$_5$).

The terms "halo", "halide", or "halogen" as used herein refer to fluoro, chloro, bromo, and iodo groups.

The term "hydroxyl" refers to the —OH group.

The terms "mercapto" or "thiol" refer to the —SH group.

The terms "carboxylate" and "carboxylic acid" can refer to the groups —C(=O)O$^-$ and —C(=O)OH, respectively. In some embodiments, "carboxylate" can refer to either the —C(=O)O$^-$ or —C(=O)OH group.

The term "phosphonate" refers to the —P(=O)(OR)$_2$ group, wherein each R can be independently H, alkyl, substituted alkyl, aralkyl, substituted aralkyl, aryl, substituted aryl, or a negative charge (i.e., wherein effectively there is no R group present to bond to the oxygen atom, resulting in the presence of an unshared pair of electrons on the oxygen atom). Thus, stated another way, each R can be present or absent, and when present is selected from H, alkyl, aralkyl, or aryl.

The term "phosphine" refers to the —P(R)$_3$ group, wherein each R is independently H, alkyl, substituted alkyl, aralkyl, substituted aralkyl, aryl, or substituted aryl.

The term "silyl" refers to groups comprising silicon atoms (Si).

The term "chiral" refers to the geometric property of a rigid object (or spatial arrangement of points or atoms in a chemical compound) of being non-superimposable on its mirror image. If the object is superimposable on its mirror image the object is described as being achiral or non-chiral. In some embodiments, a chiral molecule can comprise a "chiral center" or "stereogenic center", which refers to an atom attached to a set of substituents wherein interchanging any two substituents results in a stereoisomer. In some embodiments, the chiral center is an asymmetric carbon atom. Each chiral center (*C) can be labeled R or S according to a system by which its substituents are each designated a priority according to the Cahn Ingold Prelog priority rules (CIP), based on atomic number. In some embodiments, the stereochemistry of the chiral centers (marked by "*C") represents all possible combinations in terms of relative and absolute chemistry. In some embodiments, a chiral molecule does not contain a chiral center, but instead has axial chirality, i.e., an axis about which a set of substituents is held in a spatial arrangement that is not superimposable upon its mirror image, or inherent chirality (e.g., as a result of curvature of the molecule).

The term "isomer" as used herein refers to one of two or more molecules having the same number and kind of atoms and hence the same molecular weight, but differing in chemical structure. Isomers can differ in the connectivities of the atoms (structural isomers), or they can have the same atomic connectivities but differ only in the arrangement or configuration of the atoms in space (stereoisomers). "Stereoisomer" or "stereoisomers" refer to compounds that differ in chirality, e.g., that differ in the chirality of one or more stereocenters. Stereoisomers can include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images.

As used herein, the term "metal-organic matrix material" refers to a solid material comprising both metal and organic components, wherein the organic components include at least one, and typically more than one carbon atom. In some embodiments, the material is crystalline. In some embodiments, the material is porous. In some embodiments, the metal-organic matrix material is a coordination polymer, which comprises repeating units of coordination complexes comprising a metal-based secondary building unit (SBU, such as a metal ion or metal complex, and a bridging polydentate (e.g., bidentate) organic ligand. In some embodiments, the material contains more than one type of metal ion. In some embodiments, the material can contain more than one type of organic bridging ligand.

A "coordination complex" is a compound in which there is a coordinate bond between a metal ion and an electron pair donor, ligand or chelating group. Thus, ligands or chelating groups are generally electron pair donors, molecules or molecular ions having unshared electron pairs available for donation to a metal ion.

The term "coordinate bond" refers to an interaction between an electron pair donor and a coordination site on a metal ion resulting in an attractive force between the electron pair donor and the metal ion. The use of this term is not intended to be limiting, in so much as certain coordinate bonds also can be classified as have more or less covalent character (if not entirely covalent character) depending on the characteristics of the metal ion and the electron pair donor.

As used herein, the term "ligand" refers generally to a species, such as a molecule or ion, which interacts, e.g., binds, in some way with another species. More particularly, as used herein, a "ligand" can refer to a molecule or ion that binds a metal ion in solution to form a "coordination complex." See Martell, A. E., and Hancock, R. D., *Metal Complexes in Aqueous Solutions*, Plenum: New York (1996), which is incorporated herein by reference in its entirety. The terms "ligand" and "chelating group" can be used interchangeably.

The term "bridging ligand" can refer to a group that bonds to more than one metal ion or complex, thus providing a "bridge" between the metal ions or complexes. Organic bridging ligands can have two or more groups with unshared electron pairs separated by, for example, an alkylene or arylene group. Groups with unshared electron pairs, include, but are not limited to, —$CO_2H$, —$NO_2$, amino, hydroxyl, thio, thioalkyl, —$B(OH)_2$, —$SO_3H$, $PO_3H$, phosphonate, and heteroatoms (e.g., nitrogen, oxygen, or sulfur) in heterocycles. In some embodiments, in addition to binding to at least two metal ions or complexes in an MOF, the bridging ligand can also bind to a further metal ion or complex, e.g., to provide a catalytic moiety.

As used herein, turn over number (TON) refers to the number of moles of substrate that a mole of catalyst can convert before being inactivated.

As used herein, the term "stable" refers to a characteristic of a MOF of the presently disclosed subject matter. A "stable" MOF refers to a MOF that retains its framework structure during the catalytic reaction; such stability can be manifested by the retention of the powder X-ray diffraction pattern after the catalytic reaction.

II. Metal-Organic Framework (MOF) Catalysts and Their Synthesis

As noted above, as an emerging class of porous molecular materials, metal-organic frameworks (MOFs) provide a highly tunable platform to engineer heterogeneous catalysts for various potential reactions that cannot be achieved with traditional porous inorganic materials. See Li et al., Nature, 1999, 402, 276; Moulton et al., Chem. Rev., 2001, 101, 1629; Kitagawa et al., Angew. Chem. Int. Ed., 2004, 43, 2334; Das et al., Angew. Chem. Ing. Ed., 2011, 50, 10510; Horcajada et al., Chem. Rev., 2012, 112, 1232; Suh et al., Chem. Rev., 2012, 112, 782; Sumida et al., Chem. Rev., 2012, 112, 724; and Wang et al., J. Am. Chem. Soc., 2013, 135, 13222. In some embodiments, the presently disclosed subject matter provides MOFs that can stabilize highly active species that could undergo bimolecular or multimolecular deactivation in solution.

Chelating ligands containing pyridyl moieties such as bipyridines, phenanthrolines, and terpyridines are extensively used ligand frameworks in coordination chemistry and homogeneous catalysis. See Constable et al., Coord. Chem. Rev. 1989, 93, 205; Kaes et al., Chem. Rev., 2000, 100, 3553; Chelussi et al., Chem. Rev., 2002, 102, 3129; and Newkome et al., Eur. J. Org. Chem., 2004, 2004, 235. Owing to their robust redox stability, coordinating ability with a wide range of metal ions, and the ease of functionalization, these pyridyl ligands have offered an interesting alternative to phosphine-based ligands in developing catalytic systems for fine chemical synthesis. See Mkhalid et al., Chem. Rev. 2009, 110, 890; Hartwig, Acc. Chem. Res., 2012, 45, 864; Campbell et al., Acc. Chem. Res., 2012, 45, 851; and Sigman et al., Acc. Chem. Res., 2012, 45, 874. In some embodiments the presently disclosed subject matter provides nitrogen donor-based MOFs, such as bipyridine-based MOFs, for use in organic transformations.

In some embodiments, the presently disclosed subject matter provides metal-organic frameworks (MOFs) based on organic bridging ligands that contain nitrogen donor ligands, such as, but not limited to bipyridine, phenanthroline, terpyridine, salicylaldiminie, pyridylphenyl, 1,3-diketimine (NacNac), and bis(oxazoline). The nitrogen donor ligands can be achiral, chiral, or a mixture of chiral and achiral ligands. Further, the MOFs can contain mixtures of nitrogen donor ligands and non-nitrogen donor ligands. When the nitrogen donor ligands are complexed to catalytically active moieties, they can be used as highly active catalysts for various organic transformations. In some embodiments, the MOFs containing nitrogen donor ligands can be prepared (e.g., by contacting the nitrogen donor ligands with a first metal source, wherein the first metal source provides the metal for secondary building units of the MOF) and then post-synthetically metalated with metal precursors (such as, but not limited to Ir, Rh, Pd, V, Cr, Mn, Fe, Co, Ni, and Cu complexes) to afford metalated MOFs that can be used as catalysts. Alternatively, nitrogen bridging ligands can be complexed with catalytically active metal moieties and then used to grow MOF crystals.

In some embodiments, the catalytically active moiety comprises a first row transition metal, e.g., Cr, Mn, Fe, Co, Ni, and Cu. The MOF framework isolates the catalytic sites from each other, leading to much enhanced catalyst stability, which allows the use of first-row metal catalysts for a number of reactions that are typically catalyzed by precious metal catalysts. MOF frameworks disclosed herein thus allow the transition from precious metal catalysis to base metal catalysis.

In some embodiments, the metal-functionalized MOFs can be more active than their homogeneous controls in catalysis. For instance, these MOFs can provide a versatile family of single-site solid catalysts for catalyzing a broad scope of organic transformations, including the borylation of aromatic C—H bonds using $B_2(pin)_2$ (pin=pinacolate), ortho-silylation of benzylicsilyl ethers to corresponding benzoxasiloles as well as the dehydrogenation of substituted cyclohexenones to phenol derivatives with oxygen as the oxidant. The MOFs were also used to catalyze hydrogenation, hydrosilylation, and hydroboration of olefins and ketones.

In some embodiments the presently disclosed subject matter provides methods for preparing crystalline and porous metal-organic frameworks (MOFs) containing bipyridine ligand and other nitrogen donor ligands. The crystalline MOFs can optionally have long-range orders with periodic repeats of the metal-based secondary building units and nitrogen donor bridging ligands. Typical MOF synthesis involves heating a mixture of metal ions and bridging ligands or precursors to bridging ligands in appropriate solvent mixtures (such as dimethylformamide, diethylforamide, or others). In some instances, various amounts of acids are added to the reaction mixtures to enhance the crystallinity of the MOF crystals/microcrystals. In some cases, crystal growth modulators such as acetic acid or benzoic acid are added to the reaction mixtures to control the particle sizes of the microcrystals.

In some embodiments, the secondary building blocks can be Zr-oxo clusters as shown in the examples, Hf-oxo clusters, Zn-oxo clusters, Ti-oxo clusters, Cu-carboxylate paddlewheels, and other secondary building units that have been used to construct MOFs.

In some embodiments the presently disclosed subject matter provides uses of thus obtained nitrogen donor ligand based MOFs, such as but not limited to the catalytic organic reactions shown in Scheme 4 or other related reactions in a batch mode, in conventional solvents, or in the absence of solvents, or in unconventional solvents, such as supercritical carbon dioxide. In some embodiments the presently disclosed subject matter provides uses of thus obtained MOFs for organic transformations shown in Scheme 4 or other related reactions in a flow reactor. In some embodiments the presently disclosed subject matter provides for the use of MOFs to catalyze sequential or multistep reactions.

Typical MOF synthesis involves heating a mixture of metal ions or complexes (i.e., a first metal source) and organic bridging ligands or precursors to organic bridging ligands (e.g., nitrogen donor organic bridging ligands or their precursors or mixtures of nitrogen donor and non-nitrogen donor bridging ligands or their precursors) in appropriate solvent mixtures (such as dimethylformamide (DMF), diethylformamide, or others). In some instances, various amounts of acids, such as trifluoroacetic acid (TFA), are added to the reaction mixtures to enhance the crystallinity of the MOF crystals/microcrystals. In some cases, crystal growth modulators such as acetic acid or benzoic acid are added to the reaction mixtures to control the particle sizes of the microcrystals.

In some embodiments, the crystalline MOFs have internal pores, cavities, and open channels to transport organic substrates and products in and out of the MOFs. In some embodiments, the particle sizes of the MOFs can also be tuned to minimize the diffusion distance needed for the organic substrates and products to maximize the catalytic turnover frequency and total catalytic turnover number. For example, in some embodiments, the MOF can be prepared by contacting a nitrogen donor bridging ligand and a first metal source in a solvent or mixture of solvents selected based on solvent molecule size, such that the sizes and/or shapes of internal pores, cavities and/or open channels in the MOF can be tailored to enhance catalytic activity and/or selectivity. In some embodiments, the solvent comprises DMF.

In some embodiments, the MOFs can contain a mixture of two or more different organic bridging ligands. In some embodiments, one of the organic bridging ligands in such a "mixed" MOF can be a nitrogen donor ligand, while the other bridging ligand can be a non-nitrogen donor organic bridging ligand. In some embodiments, the nitrogen donor organic bridging ligand is chiral and the non-nitrogen donor organic bridging ligand is achiral. In some embodiments, the "mixed" MOFs can be prepared to increase the channel size of the MOF and/or to maximize the efficiency of chiral ligand usage.

When a mixture of chiral and non-chiral bridging ligands are used, the ratio of chiral and non-chiral ligand can be any desirable ratio. In some embodiments, the molar ratio can range from 9:1 non-chiral ligand:chiral ligand to 1:9 non-chiral ligand:chiral ligand. In some embodiments, it can be economically advantageous to use a greater amount of non-chiral ligand. In some embodiments, the ratio of non-chiral:chiral ligand can be between 9:1 to about 2:1 (e.g., about 9:1, about 8:1, about 7:1, about 6:1, about 5:1, about 4:1, about 3:1, or about 2:1).

In some embodiments, the first metal source, i.e., the source of the metal of the SBU is a metal alkoxide or a metal halide. In some embodiments, the first metal source is zirconium tetrachloride ($ZrCl_4$) or hafnium tetrachloride ($HfCl_4$).

In addition to comprising a nitrogen donor moiety or moieties (i.e., that can bind to a second metal, such as Ti, V, Cr, Mn, Fe, Co, Ni, Cu, Rh, Ru, Ir, Os, Pt, or Pd), the nitrogen donor organic bridging ligand also includes chemical moieties that can bond (e.g., coordinatively bond) to the metal containing SBUs. Thus, the nitrogen donor organic bridging ligand can comprise a nitrogen donor moiety core structure that is further substituted (or derivatized with) with one or more groups that include a moiety, such as, but not limited to, a carboxylate or carboxylic acid, an ester, an amide, a pyridine or other nitrogen containing aromatic group, an amine (including nitrogen-containing heterocycles), a hydroxyl, a thiol, a thioalkyl, —$B(OH)_2$, —$SO_3H$, —$PO_3H$, —$NO_2$, or a phosphonate. In some embodiments, the nitrogen donor-based bridging ligand is substituted with one or more groups selected from a carboxylate, a pyridine or a phosphonate. In some embodiments, the nitrogen donor-based bridging ligand is a dicarboxylate, a tricarboxylate, a tetracarboxylate, a bipyridine, a tripyridine, a tetrapyridine, a diphosphonate, a triphosphonate, or a tetraphosphonate.

The nitrogen donor core structure of the nitrogen donor organic bridging ligand can comprise any suitable nitrogen donor moiety. The nitrogen donor core structure can include aromatic rings that include a nitrogen in an aromatic ring and/or that are substituted with an nitrogen-containing group. The nitrogen donor core structure can also be non-aromatic. Exemplary nitrogen donor core structures that can be used according to the presently disclosed subject matter are shown in Scheme 1, below.

Scheme 1. Examples of nitrogen-based donors that can be modified and used to build MOFs.
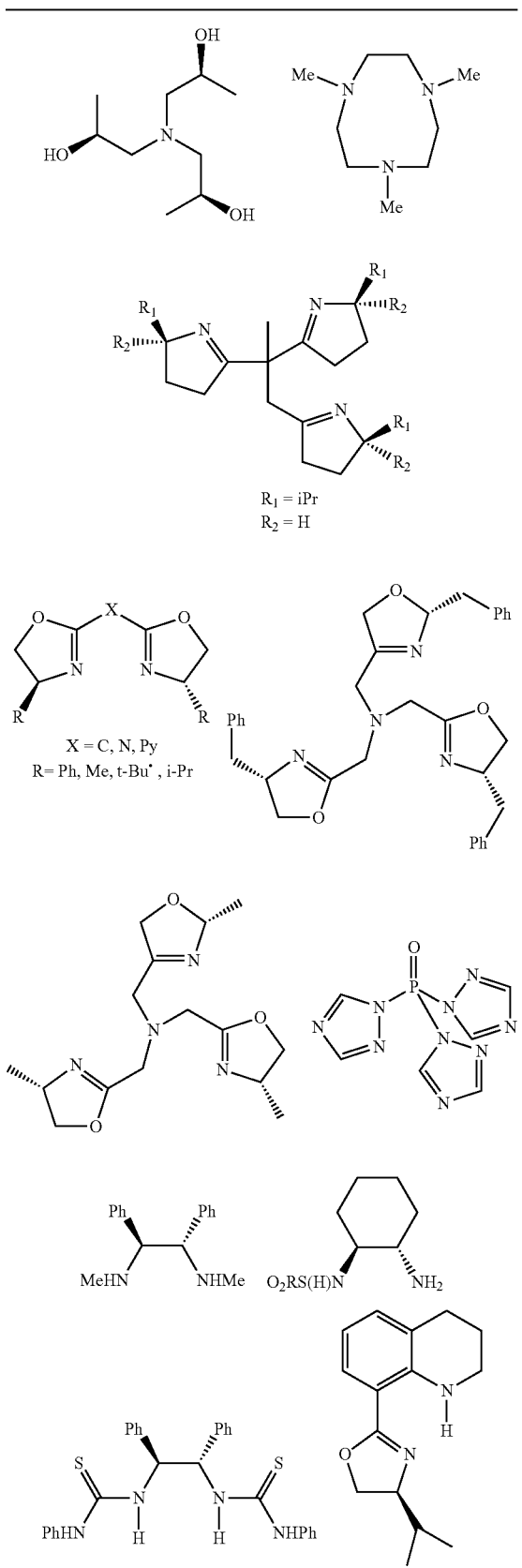
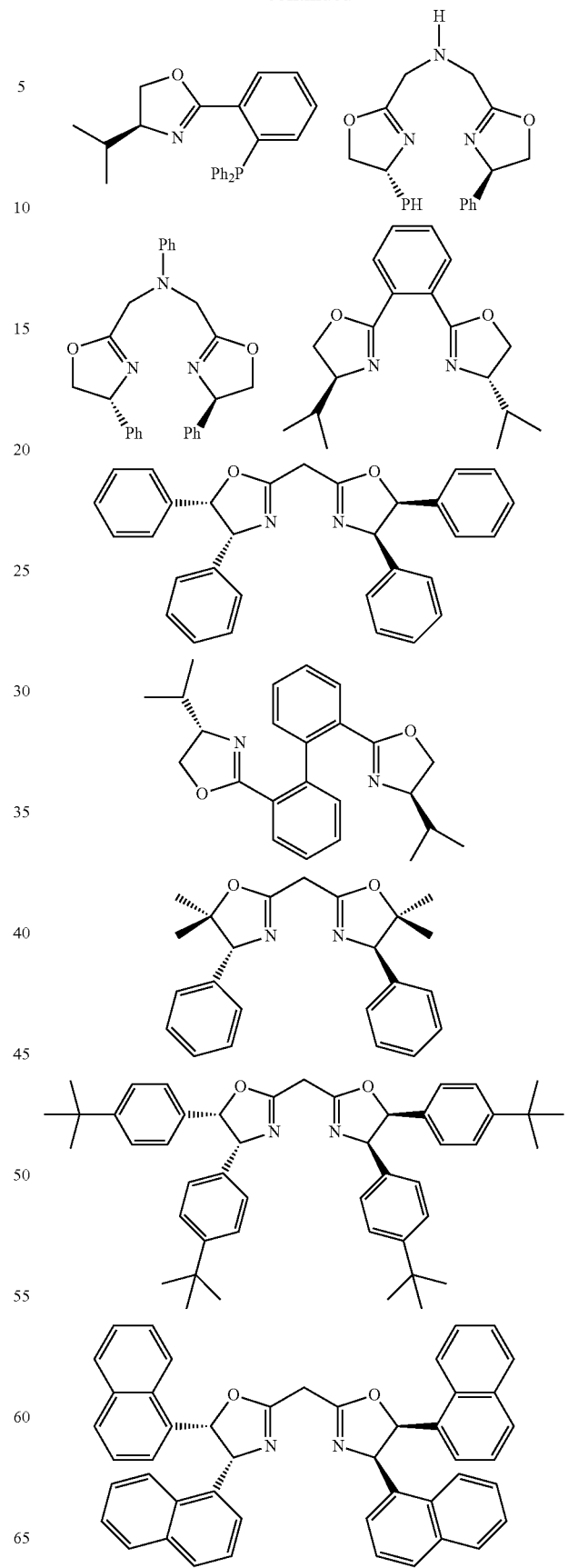
-continued

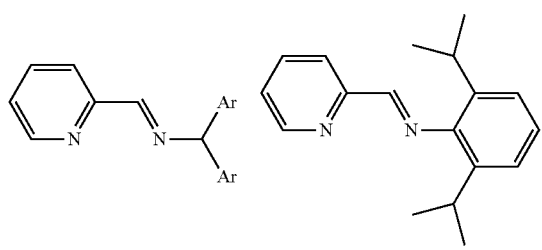
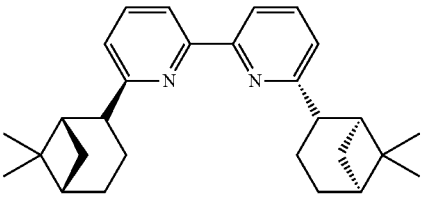
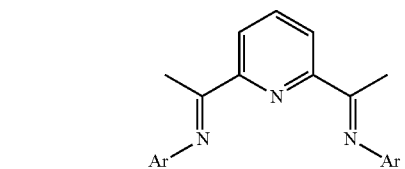
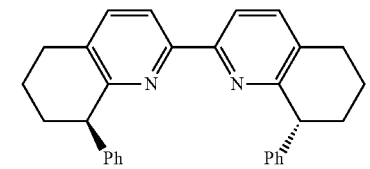
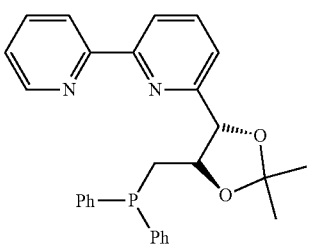
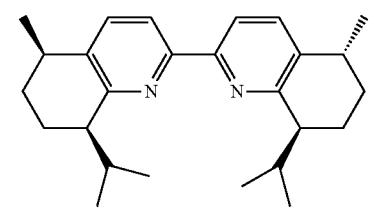
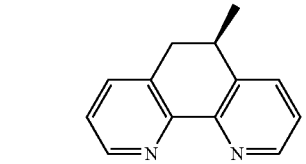
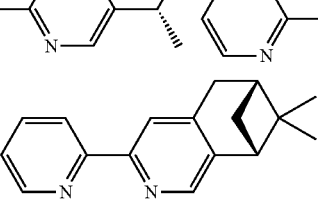
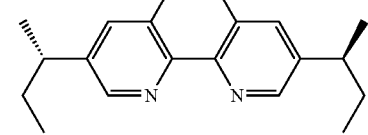
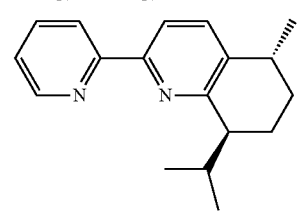
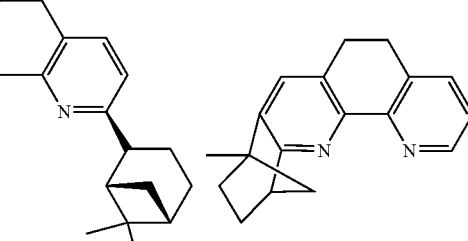
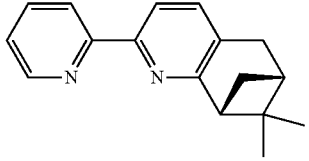
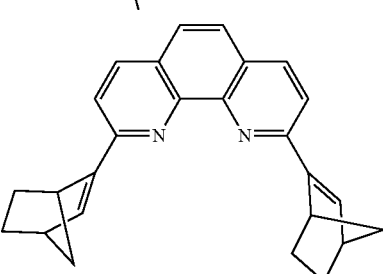
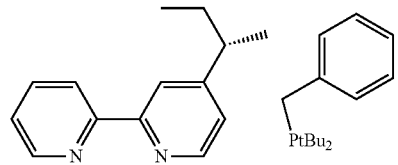
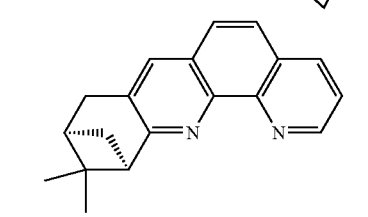
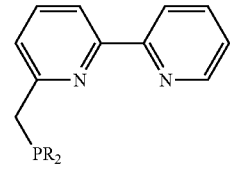

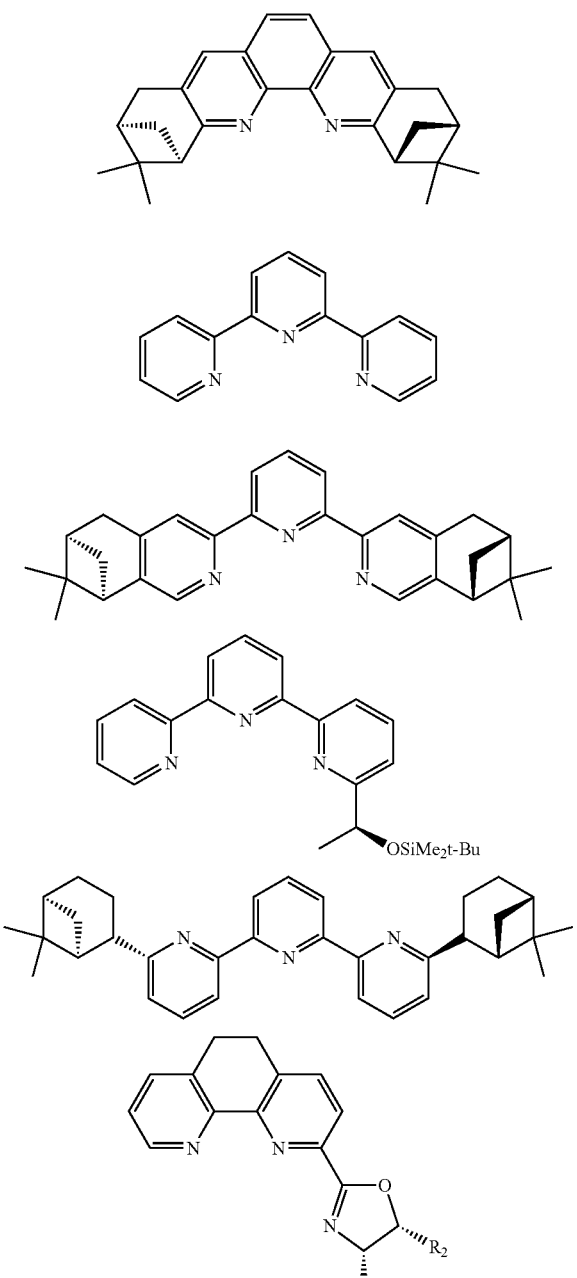

R₁ = CH₃, R₂ = H
R₁ = CH₂CH(CH3)₂, R₂ = H
R₁ = CH₃, R₂ = H
R₁ = CH₃, R₂ = Ph

In some embodiments, the nitrogen donor-based bridging ligand is not a derivative of a N,N'-alkylenebis(salicylimine) or of a N,N'-arylenebis(salicylimine). Thus, the nitrogen donor core structure of the nitrogen donor-based bridging ligand is not a structure such as shown in Scheme 2, below, wherein R is alkylene, substituted alkylene, arylene, or substited arylene. Accordingly, the core structure of the nitrogen donor-based is other than salen or salen-like moieties such as shown in Scheme 3.

Scheme 2. Structure of N,N'-alkylenebis (salicylimine) (wherein R is alkylene of substituted alkylene) and N,N'-arylenebis (salicylimine) (where R is arylene or substituted arylene).

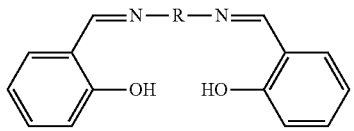

Scheme 3. Structure of salen (top) and similar compounds.

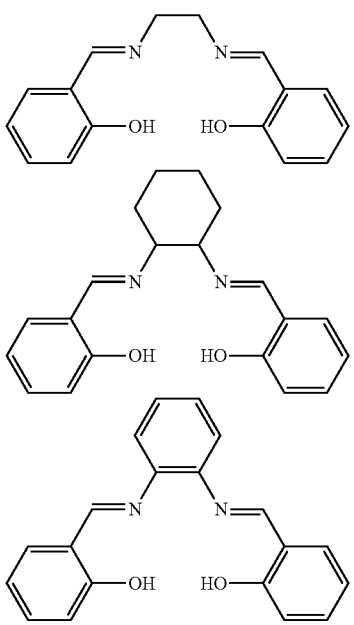

In some embodiments, the MOF is based on a bipyridine-derived dicarboxylate linker (L) and is called Bpy-UiO. The Bpy-UiO can be post-synthetically metalated to afford highly active catalysts. This bpy-UiO-MOF contains the $Zr_6O_4(OH)_4(O_2CR)_{12}$ cluster SBU and adopts the same framework topology as UiO-67 that was previously reported by Lillerud and coworkers. See Bloch et al., J. Am. Chem. Soc., 2010, 132, 14382; Li et al., Chem. Commun., 2014, 50, 2304; Nickerl et al., Inorg. Chem. Front., 2014; doi: 10.1039/c3qi00093q, and Fei et al., Chem., Commun., 2014, 50, 4810. The UiO structure provides an ideal platform to design MOF-based heterogeneous catalysts due to their stability under a range of reaction conditions. As described in the Examples, Bpy-UiO is a versatile precursor to multiple catalytic systems through the judicious choice of post-synthetic metalation conditions. The metalated bpy-UiO materials are efficient catalysts for the borylation of aromatic C—H bonds and ortho-silylation of benzylicsilyl ethers as well as dehydrogenation of substituted cyclohexenones.

III. Catalytic Reactions

In some embodiments the presently disclosed subject matter provides uses of the presently disclosed MOF-based catalysts, such as but not limited to, as catalysts for one or more of the organic transformations shown in Scheme 4, below, or other related reactions in a batch mode, in conventional solvents, in the absence of solvents, or in unconventional solvents, such as supercritical carbon dioxide. In some embodiments the presently disclosed subject matter provides uses of MOF catalysts for catalyzing organic transformations shown in Scheme 4 or other related reactions in a flow reactor or a supercritical fluid reactor to enable green manufacturing of fine chemicals. In some embodiments the presently disclosed subject matter provides for the use of MOF catalysts to catalyze sequential or multistep reactions. In some embodiments the presently disclosed subject matter provides for the use of MOFs in the same system to catalyze sequential or multistep reactions. In some embodiments, the presently disclosed subject matter provides for the use of chiral MOF catalysts to catalyze asymmetric organic transformations.

Scheme 4. Examples of asymmetric organic reactions that can be catalyzed by MOFs.

Hydrogentation:

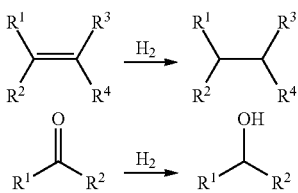

Hydroformylation:

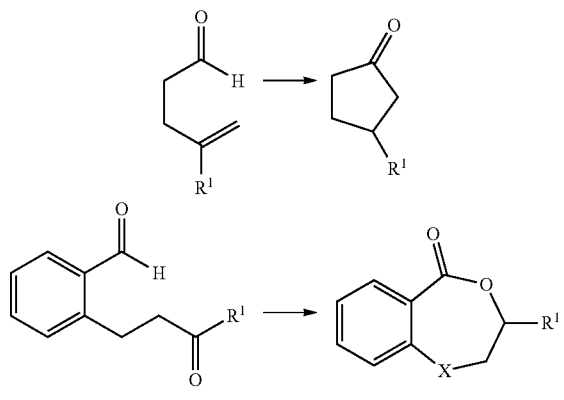

X = O, S, $NR^2$

Hydroboration:

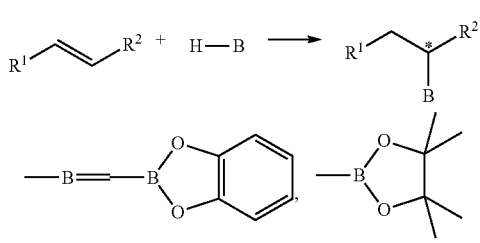

Hydroamination:

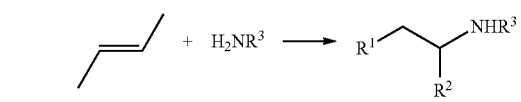

Primary C—H silylation

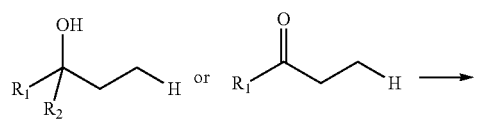

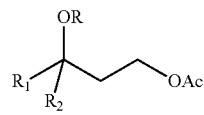

Oxidation of Primary Alcohols to Aldehydes

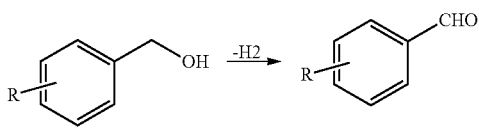

Hydrosilylation of olefins and ketones

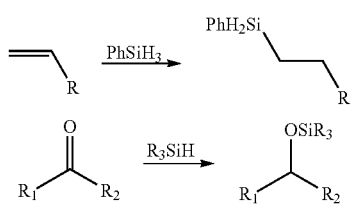

Direct Arylation through Directed C—H Bond Activation

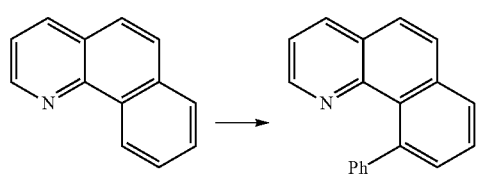

Biaryl Coupling

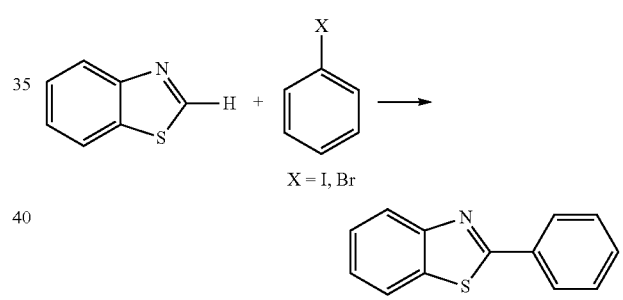

X = I, Br

Ar—H/Ar—Si couplings of azoles and trimethoxyarylsilanes

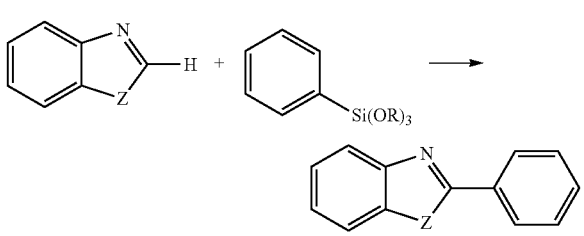

Tandem C—H Activation/ Arylation

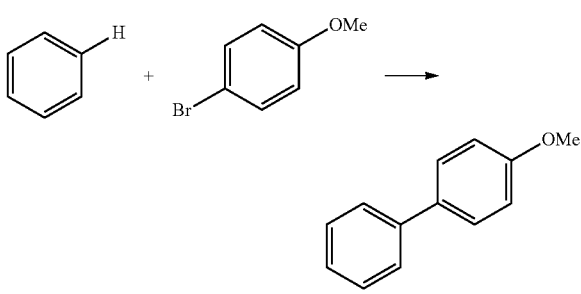

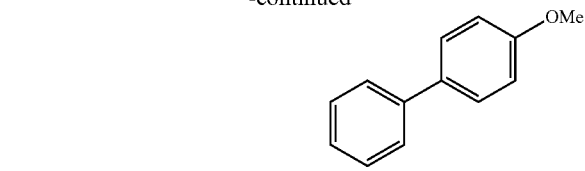

Olefin C—H functionalization:

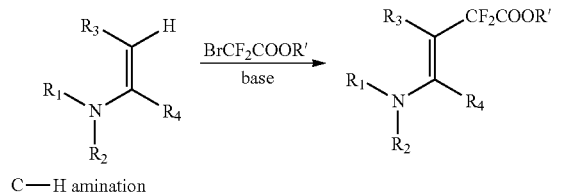

C—H amination:

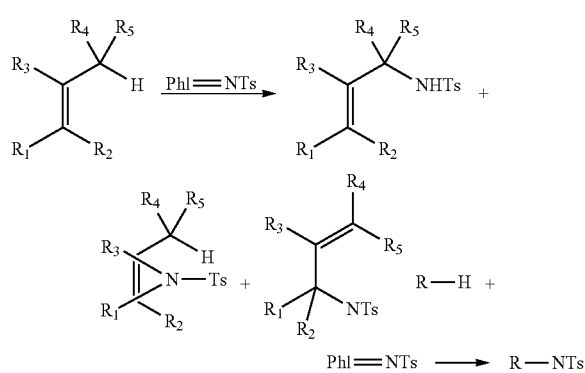

Alkene oxidation

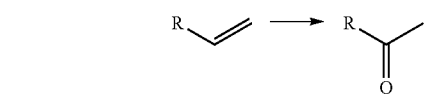

Cyclopropanation

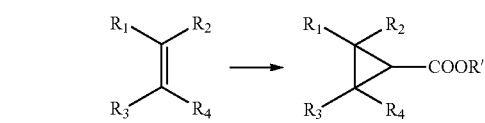

Ring expansion

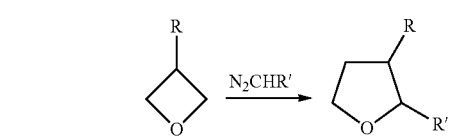

Allylic substitution

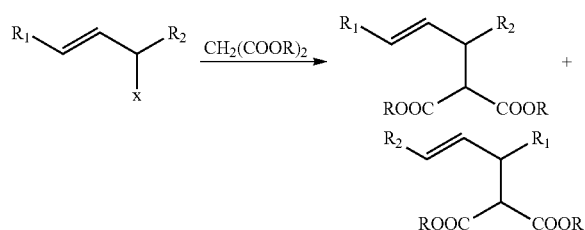

Nucleophilic addition

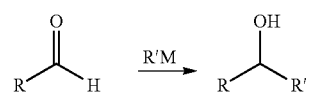

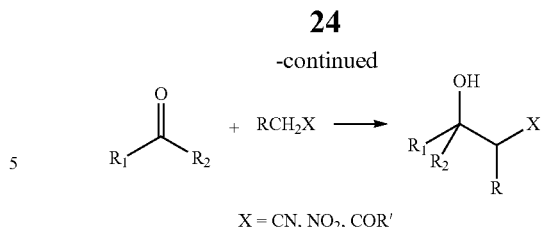

X = CN, NO$_2$, COR'

Transfer hydrogenation

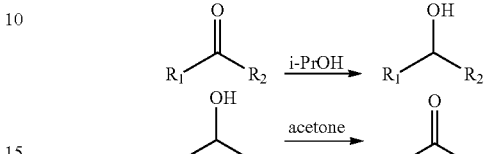

Allylic oxidation

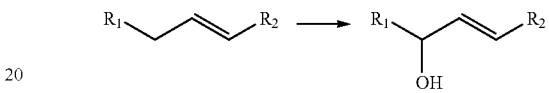

Epoxidation

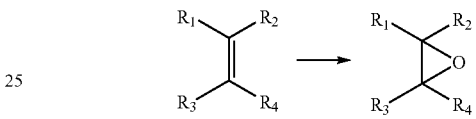

Conjugated additions:

a) Michael Reaction

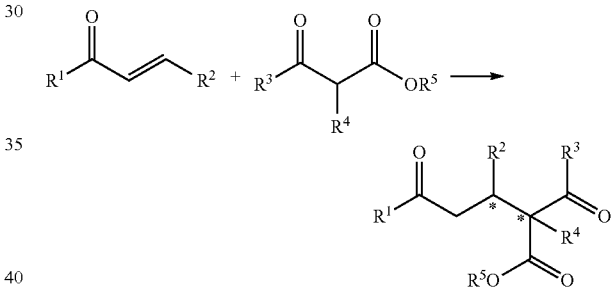

b) Aza-Michael Reaction

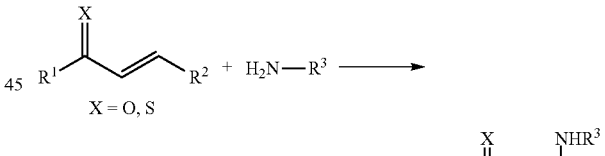

For instance, in some embodiments, the presently disclosed subject matter provides a method for preparing a compound comprising contacting a substrate (or substrates) capable of forming a product by catalytic transformation with a heterogeneous catalyst of the presently disclosed subject matter. In some embodiments, the catalytic transformation is selected from the group comprising hydrogenation; dehydrogenation; isomerization, optionally the isomerization of an allylamine, an allyl alcohol, or an α,β-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an α-substitution reaction, optionally wherein the α-substitution reaction is a protonation, a fluorination, an amination, an arylation, or an orthoester alkylation; an ene reaction; a Diels-Alder reaction; a Pauson-Khand reaction; an enyne intramolecular cyclization; a [2+2+2] cycloaddition; a [3+2] cycloaddition; and a ring-opening reaction. In some embodiments, the catalytic transformation is selected from a hydroboration of an arene (i.e., a CH borylation of an arene), an ortho-silylation of an arene, dehydrogenation of a cyclohexenone, or hydrogenation of an olefin.

The contacting can take place in any suitable solvent, e.g., a solvent in which the substrate can be dissolved. In some embodiments, the solvent is an ether, such as tetrahydrofuran or dioxane; an alkane, such as a hexane (e.g., n-hexane), a heptane (e.g., n-heptane), or an octane (e.g., n-octane); a halogenated alkene, such as dichloromethane, dichloroethane, or chloroform; an aromatic solvent, such as benzene, toluene, or a xylene; DMF, dimethylsulfoxide (DMSO), an alcohol, such as methanol or ethanol; water, or mixtures thereof. In some embodiments, the solvent is an unconventional solvent, such as supercritical carbon dioxide. In some embodiments, no solvent is present (i.e., the reaction is performed "neat"). In some embodiments, the contacting takes place in the presence of a gas, such as hydrogen gas, and/or under pressure. In some embodiments, the contacting is done in conjunction with heating or cooling.

In some embodiments, the asymmetric reaction is done in a flow reactor, e.g., wherein the catalyst is present in a reaction chamber into which a solvent or solvents can be pumped in and out and wherein the solvent or solvents can comprise a substrate or substrates dissolved therein.

The presently disclosed catalysts can have high turnover number (TON). For example, in some embodiments, the presently disclosed MOF-based catalysts can have a TON of greater than about 50, greater than about 100, greater than about 200, greater than about 400, greater than about 1000, greater than about 10,000, greater than about 30,000, greater than about 60,000, greater than about 100,000, greater than about 200,000, greater than about 500,000, or greater than about 1,000,000.

In some embodiments, the presently disclosed catalysts can be used at low catalyst loadings, e.g., at less than about 10 mole %, less than about 5 mole %, less than about 4 mole %, less than about 3 mole %, less than about 2 mole %, less than about 1 mole %, less than about 0.5 mole %, or less than about 0.2 mole % compared to the substrate. In some embodiments, the catalysts can be used at a catalyst loading of between about 0.001 mole % and about 1.5 mole %. In some embodiments, the catalysts can be used at a catalyst loading of between about 0.04 mole % and about 1.2 mole % (e.g., at about 0.04, 0.05. 0.06, 0.07, 0.08, 0.09, 0.1, 0.2, 0.3, 0.4, 0.5, 0.6, 0.7, 0.8, 0.9, 1.0, 1.1, or about 1.2 mole %).

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods

All solvents were purchased from Fisher (Thermo Fisher Scientific, Waltham, Mass., United States of America) and used without further purification. All of the reactions and manipulations were carried out under nitrogen with the use of standard inert atmosphere and Schlenk techniques unless otherwise indicated. Diethyl(hydrido)silyl ethers (3a-3e), 5,5'-bis-methoxycarbonyl-2,2'-bipyridine, 3-ethylcyclohex-2-enone (5c), 3-phenylcyclohex-2-enone (5d), (see Kitagawa et al., Angew. Chem. Int. Ed., 2004, 43, 2334) and $[Pd(CH_3CN)_4][BF_4]_2$ were prepared according to published procedures. $[Ir(COD)(OMe)]_2$ and 2,2'-bipyridine-5,5'-dicarboxylic acid were purchased from Aldrich (Sigma-Aldrich, St. Louis, Mo., United States of America) and $Et_2SiH_2$ was purchased from Alfa Aesar (Ward Hill, Mass., United States of America). All of the other substrates and reagents are commercially available and used as received unless otherwise indicated. 1,2-dimethoxybenzene, o-xylene, m-xylene, 1-bromo-3-iodobenzene and 1,2-dichlorobenzene were dried with freshly activated 4 Å molecular sieves in a glovebox prior to use. $^1H$ NMR spectra were recorded on a Bruker NMR 400 DRX spectrometer (Bruker Corporation, Billerica, Mass., United States of America) at 400 MHz and referenced to the proton resonance resulting from incomplete deuteration of the deuterated chloroform (δ 7.26). Thermogravimetric analysis (TGA) was performed in air using a Shimadzu TGA-50 thermogravimetric analyzer (Shimadzu Corporation, Kyoto, Japan) equipped with a platinum pan. Powder X-ray diffraction (PXRD) patterns were collected on a Bruker D8 Venture, dual microsource (Cu and Mo) diffractometer with a CMOS detector (Bruker Corporation, Billerica, Mass., United States of America). Cu Kα radiation was used. The PXRD patterns were processed with the APEX 2 package using PILOT plug-in. The conversions of reactions and yields of the products were determined by gas chromatography (GC) using a Shimadzu GC-2010 gas chromatograph (Shimadzu Corporation, Kyoto, Japan) equipped with a flame ionization detector (FID) and Supelco β-dex 120 column (Sigma-Aldrich, St. Louis, Mo., United States of Americ). GC conditions: Inj: 220° C.; Det: 250° C.; Column temp: 100° C. isothermal for 30 minutes followed by a ramp of 10° C./min to 200° C. and held for 15 minutes; Column flow: 1.01 mL/min. ICP-MS data were obtained with an Agilent 7700x ICP-MS (Agilent Technologies, Santa Clara, Calif., United States of America) and analyzed using ICP-MS MassHunter version B01.03. Samples were diluted in a 2% $HNO_3$ matrix and analyzed with a $^{159}Tb$ internal standard against a six-point standard curve over the range from 0.1 ppb to 1000 ppb. The correlation coefficient was >0.9997 for all analytes of interest. Data collection was performed in Spectrum Mode with five replicates per sample and 100 sweeps per replicate.

Example 2

Synthesis and Characterization of Bipyridine MOFs (bpy-UiOs)

Synthesis of $Zr_6(OH)_4O_4L_6$ (bpy-UiO)

$ZrCl_4$ (30 mg, 0.13 mmol), 2,2'-bipyridine-5,5'-dicarboxylic acid ($H_2L$, 30 mg, 0.12 mmol), DMF (15 mL) and trifluoroacetic acid (0.06 mL) were charged in a vial and heated to 100° C. for 5 days. The resulting solid was collected and washed with DMF to give 40 mg of bpy-UiO (yield 65%).

Figure 1A:
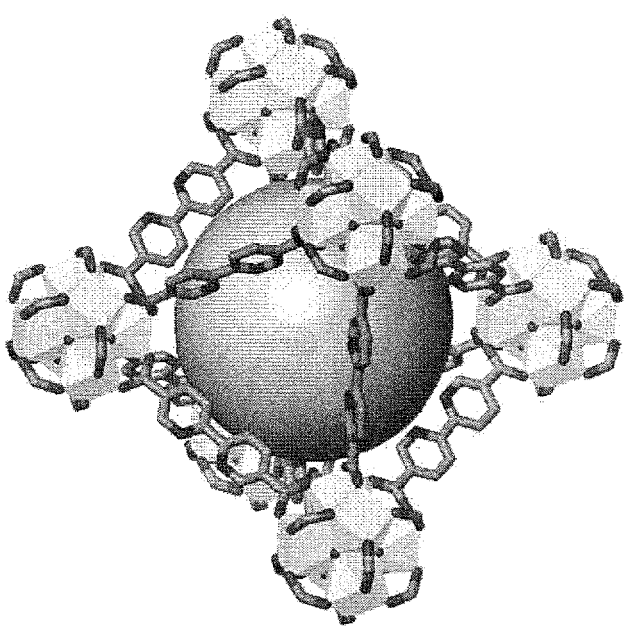
FIG. 1A is a schematic drawing of the x-ray crystal structure of a metal-organic framework (MOF) of the presently disclosed subject matter, referred to as Bpy-UiO, comprising a bipyridine-based organic bridging ligand and zirconium-oxo clusters as secondary building units.
Figure 1C:
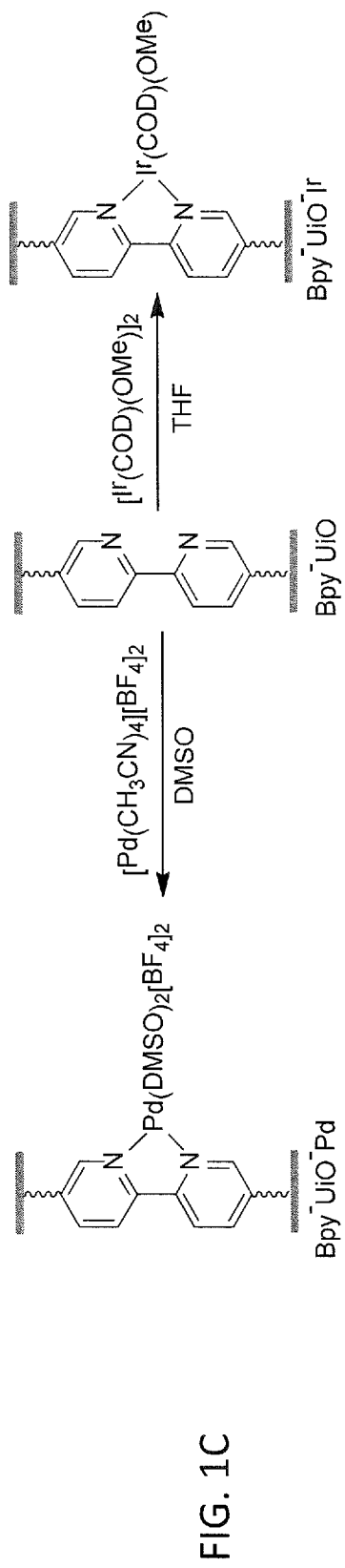
FIG. 1C is a schematic drawing showing the post-synthetic metalation of the metal-organic framework (MOF) described in FIG. 1A, i.e., Bpy-UiO (middle structure) with either a palladium (Pd) metal complex (left-hand reaction) or an iridium (Ir) metal complex (right-hand reaction) to prepare the Pd and Ir metalated MOFs, i.e., Bpy-UiO-Pd and Bpy-UiO-Ir, respectively.
Figure 1D:
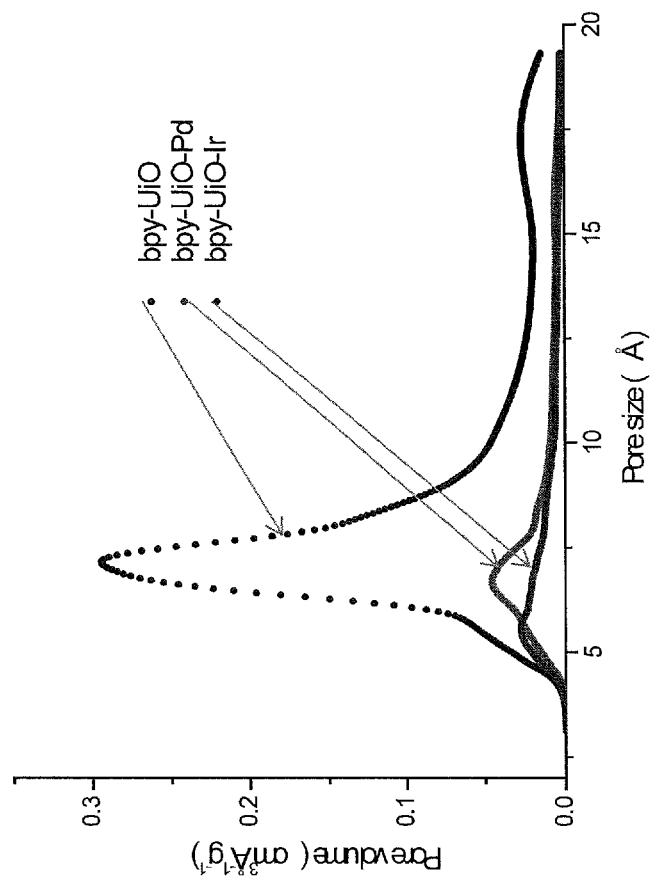
FIG. 1D is a graph showing the pore size (in angstroms, Å) and pore volume of a metal-organic framework (MOF) of the presently disclosed subject matter, referred to as Bpy-UiO, comprising a bipyridine-based organic bridging ligand and zirconium-oxo clusters as secondary building units; as well as those of Bpy-UiO metalated with palladium, i.e., Bpy-UiO-Pd; and Bpy-UiO metalated with iridium, i.e., Bpy-UiO-Ir.

The bpy-UiO solid showed an identical powder pattern to that simulated from the single crystal structure. See FIGS. 1A and 1G. See also Li et al., Chem. Commun., 2014, 50, 2304. Bpy-UiO exhibited a BET surface area of 2277 $m^2/g$ and a pore size of about 7.2 Å, consistent with the single crystal structure. See FIG. 1D.

Post-Synthetic Metalation of bpy-UiO with [Ir(COD)(OMe)]$_2$ to Provide bpy-UiO-Ir:

In a glovebox, bpy-UiO (30.0 mg) was weighed onto a filter paper and then charged into a vial. [Ir(COD)(OMe)]$_2$ (9.3 mg, 14.1 µmol) dissolved in 2.0 mL of THF was added to the vial and the mixture was kept in the glovebox for 12 h. See FIG. 1C. The resultant deep green solid was centrifuged out of suspension and washed with THF 3-4 times. The resulting bpy-UiO-Ir was stored in THF in the glovebox. Bpy-UiO-Ir has 24% solvent weight based on TGA analysis.

Post-Synthetic Metalation of bpy-UiO with [Pd(CH$_3$CN)$_4$][BF$_4$]$_2$ to Provide bpy-UiO-Pd:

Bpy-UiO (20.0 mg) was weighed onto a filter paper and then charged into a dram vial. 3.0 mL DMSO and [Pd(CH$_3$CN)$_4$][BF$_4$]$_2$ (8.3 mg, 18.8 µmol) were added to the vial and the mixture was slowly stirred at room temperature for 4 h. See FIG. 1C. The resultant light yellow bpy-UiO-Pd was centrifuged out of suspension washed with DMSO 3-4 times and stored in DMSO. Bpy-UiO-Pd has 15% solvent weight based on TGA analysis.

Figure 1F:
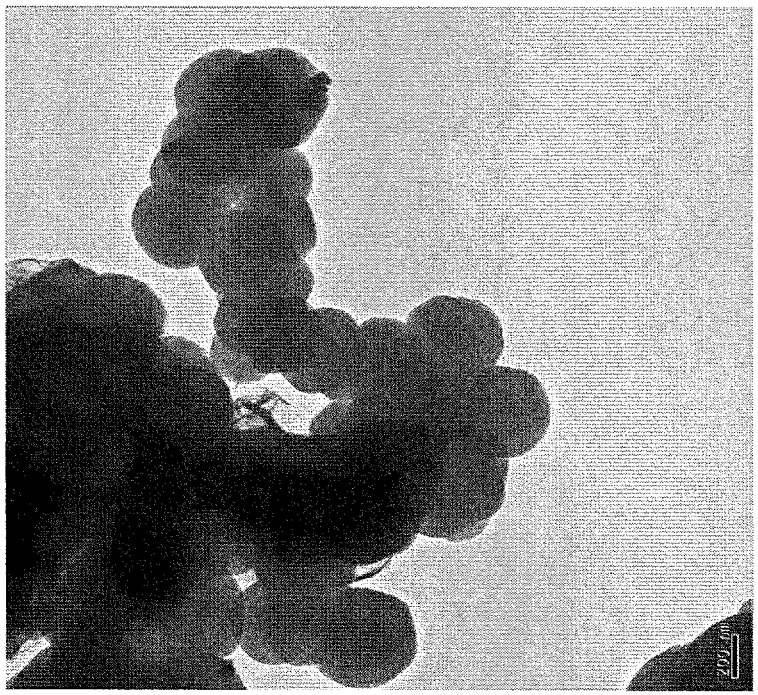
FIG. 1F is a transmission electron microscopy (TEM) image of the metal-organic framework (MOF) described in FIG. 1A, metalated with palladium, i.e., Bpy-UiO-Pd. The scale bar in the lower left-hand corner represents 200 nanometers (nm).
Figure 1E:
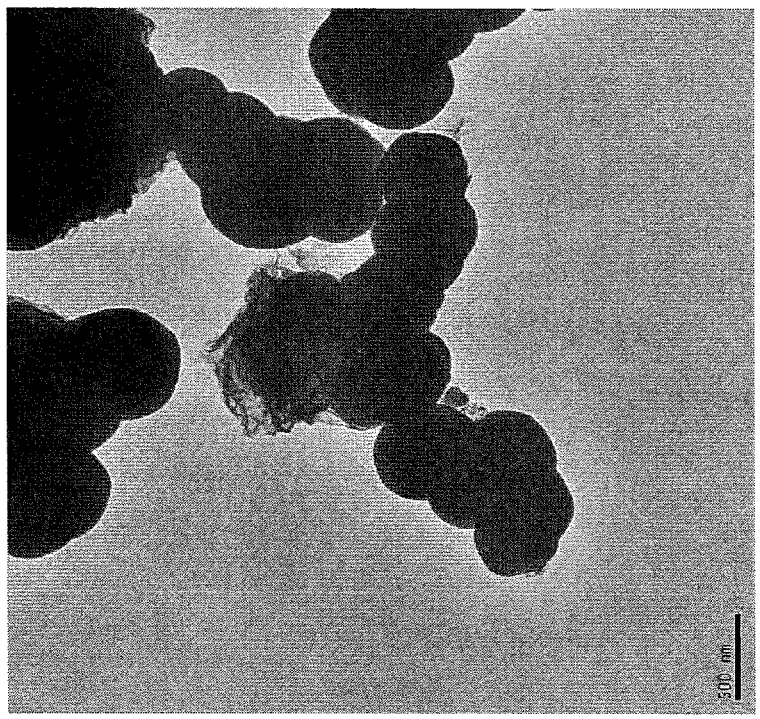
FIG. 1E is a transmission electron microscopy (TEM) image of the metal-organic framework (MOF) described in FIG. 1A, metalated with iridium, i.e., Bpy-UiO-Ir. The scale bar in the lower left-hand corner represents 500 nanometers (nm).
Figure 1G:
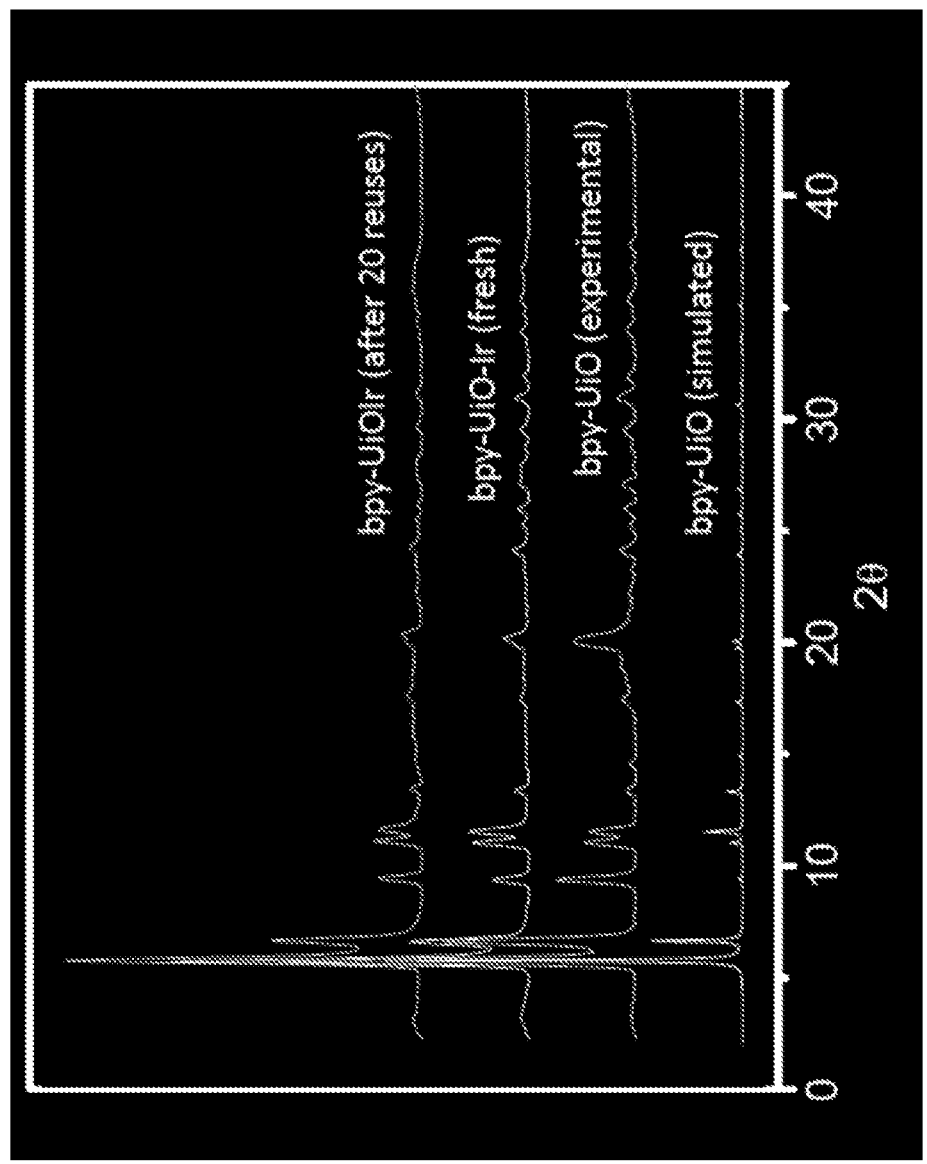
FIG. 1G is a graph showing the powder x-ray diffraction (PXRD) patterns for metal-organic frameworks (MOFs) according to the presently disclosed subject matter prepared from a bipyridine-based organic bridging ligand and zirconium-oxo clusters. The pattern at the bottom is a simulated curve for the unmetalated MOF, i.e., Bpy-UiO. The pattern second from the bottom is the experimental curve for the unmetalated MOF. The pattern third from the bottom is for the MOF freshly metalated with iridium, i.e., Bpy-UiO-Ir. The pattern at the top is for the iridium metalated MOF after 20 reuses as a catalyst for the borylation of m-xylene.

The crystallinity of bpy-UiO was maintained in both bpy-UiO-Ir and bpy-UiO-Pd as shown by their PXRD patterns that are the same as that of bpy-UiO. See FIG. 1G. Nitrogen adsorption measurements indicated that both bpy-UiO-Ir and bpy-UiO-Pd have much reduced BET surface areas (365.0 and 457.5 $m^2/g$, respectively) and slightly reduced pore sizes of 5.6 and 6.7 Å, respectively. See FIG. 1D. The smaller surface areas, pore sizes, and pore volumes of bpy-UiO-Ir and bpy-UiO-Pd are believed due to the presence of Ir/Pd cations and associated ligands in the MOF cavities. Transmission electron microscopy (TEM) images showed that bpy-UiO has a particle size of around 300 nm (See FIG. 1B) and the particles appear to be highly aggregated. TEM images for the metalated MOF are shown in FIGS. 1E and 1F.

Dye Uptake Experiments of bpy-UiO:

Bpy-UiO was soaked in a solution of azobenzene (10 g/L in ethanol/water 7:3 v/v) or rhodamine 6G (10 g/L in ethanol) overnight and then centrifuged. The supernatants were diluted to fit the dynamic range of the UV-vis spectrometer on which absorption spectra were taken and compared with the original solution. Amounts of dye uptake were determined to be 99 mg/g and 60 mg/g for azobenzene and rhodamine 6G, respectively, with regard to the framework weight.

Example 3

C—H Borylation of Arenes Catalyzed by Bipyridine MOF Catalysts

Scheme 5. C—H Borylation Reaction of an Exemplary Arene Catalyzed by a Bipyridine MOF Catalyst

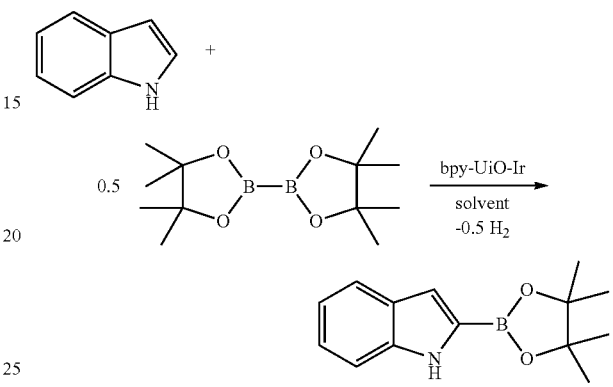

General Procedure for bpy-UiO-Ir Catalyzed C—H Borylation of Arenes:

Scheme 5 shows a C—H borylation reaction of an exemplary arene catalyzed by a bipyridine MOF catalyst. In a glovebox, bpy-UiO-Ir in THF (1.6 mg, 0.5 mol % Ir) was quickly weighed onto a filter paper, charged into a vial and 2 mL n-heptane was added. Then, arene (163.9 µmol) and $B_2(pinacolate)_2$ ($B_2pin_2$; 20.8 mg, 81.9 µmol) were added to the vial and the resultant mixture was transferred to a storage tube. The tube was sealed with a teflon stopper and heated at 100° C. in an oil bath for 10-30 h with gentle shaking. The reaction mixture was cooled to room temperature and the solid was centrifuged out of suspension in the glovebox. The solid was extracted with n-heptane 2-3 times and recycled. The combined organic extracts were concentrated in vacuo and purified by silica gel preparative TLC to yield the pure product.

Table 1 shows how the reaction conversion percentage (%) varied by reaction solvent, temperature, and time.

TABLE 1

Conversion (%) under different solvents, temperatures and reaction times for catalytic C—H borylation of arenes.[a]

| Entry | Ir loading (mol %) | Solvent | Temperature (° C.) | Time | Conversion (%)[b] |
|---|---|---|---|---|---|
| 1 | 1.0 | hexane | 23 | 40 h | 30 |
| 2 | 1.0 | hexane | 60 | 2 d | 72 |
| 3 | 1.0 | heptane | 100 | 16 h | 100 |
| 4 | 0.5 | heptane | 100 | 30 h | 100 |
| 5 | 0.1 | heptane | 100 | 4 d | 100 |
| 6 | 1.0 | THF | 80 | 36 h | 94 |

[a]Reaction conditions: 1.0 ml solvent.
[b]Conversion was determined by GC analysis.

Exemplary Procedure for bpy-UiO-Ir Catalyzed C—H Borylation of Neat Arenes:

Scheme 6
C—H Borylation of an Exemplary Arene Catalyzed by a Bipyridine MOF.

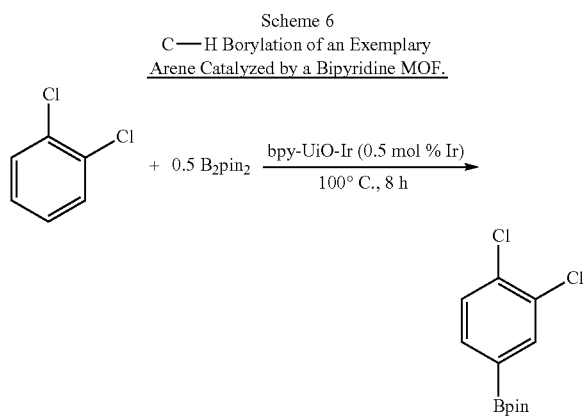

As shown in scheme 6, in a glovebox, bpy-UiO-Ir in THF (1.6 mg, 0.5 mol % Ir) was quickly weighed onto a filter paper, charged into a vial and 0.5 mL 1,2-dichlorobenzene was added. Then, 1,2-dichlorobenzene (1.0 mL) and B$_2$pin$_2$ (20.8 mg, 81.9 µmol) were added to the vial and the resultant mixture was transferred to a storage tube. The tube was sealed and heated at 100° C. for 8 h. The reaction mixture was cooled to room temperature and the solid was centrifuged out of suspension in the glovebox. The extract was concentrated in vacuo and purified by preparative TLC (Hexane:EtOAc=9:1) to give 1,2-dichloro-4-(4,4,5,5-tetramethyl-1,3,2-dioxaborolan-2-yl)benzene as a colorless solid (41.6 mg, 152.4 µmol, 93.0%). $^1$H NMR (chloroform-d$_1$, 400 MHz): δ 7.87 (d, 1H, J$_{H-H}$=1.2 Hz) 7.60 (m, 1H), 7.44 (m, 1H), 1.34 (s, 12H).

Recyclability Test for bpy-UiO-Ir in Borylation of Arenes:

Scheme 7
Recycle and reuse of bpy-UiO-Ir for C—H borylation of m-xylene.

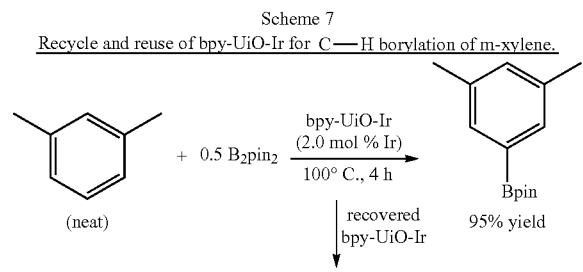

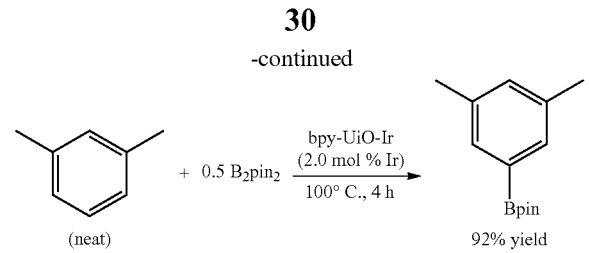

As shown in Scheme 7, in a glovebox, m-xylene (2.0 mL), B$_2$pin$_2$ (41.7 mg, 164.4 µmol) and bpy-UiO-Ir (13.2 mg, 2.0 mol % Ir) were charged into a storage tube. The tube was sealed and heated at 100° C. in an oil bath until complete consumption of B$_2$pin$_2$ was observed as determined by GC analysis (generally 4-7 h). During heating, the solution was gently shaked. After completion of the reaction, the mixture was cooled to room temperature and the solid catalyst was separated via centrifugation in the glovebox. All the volatiles of the supernatant were removed in vacuo to give crude 5-(4,4,5,5-tetramethyl-1,3,2-dioxaborolan-2-yl)-m-xylene as a colorless solid (isolated yield of crude product: 73.6 mg, 317.1 µmol, 96.4%; GC yield: 94.9%), which was sufficiently pure as shown by $^1$H NMR spectrum.

The recovered solid catalyst was added to a 2.0 mL solution of B$_2$pin$_2$ (41.7 mg, 164.4 µmol) in m-xylene and transferred to the storage tube. After heating at 100° C. for 4-7 h, the solid catalyst was separated via centrifugation in the glovebox. The volatiles of the supernatant was removed in vacuo to give 5-(4,4,5,5-Tetramethyl-1,3,2-dioxaborolan-2-yl)-m-xylene (GC yield: 92%).

Test of Air-Sensitivity of the bpy-UiO-Ir Catalyst:

A vial was charged with bpy-UiO-Ir (5.0 mg, 0.5 mol % Ir) in THF and the mixture was exposed to air for 26 h. O-xylene (2.0 mL) and B$_2$pin$_2$ (63.5 mg, 250.1 µmol) were added to the vial in air. The vial was sealed with a plastic cap and then heated at 100° C. for 15 h. 4-(4,4,5,5-Tetramethyl-1,3,2-dioxaborolan-2-yl)-o-xylene was produced in only 13% yield. This result suggests that the bpy-UiO-Ir catalyst is air-sensitive.

Test of "Heterogeneity" of bpy-UiO-Ir:

Scheme 8
The C—H borylation of m-xylene reaction stopped after removing bpy-UiO-Ir from the reaction mixture, demonstrating the "heterogeneous" nature of MOF catalysis.

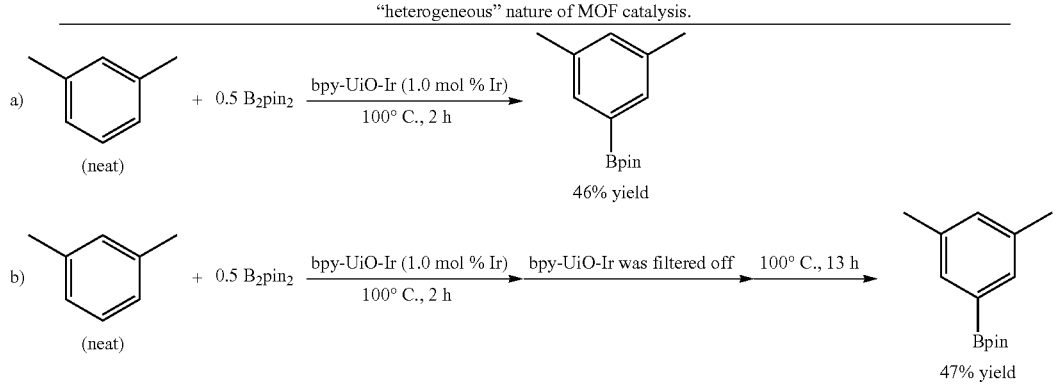

As shown in Scheme 8a), a mixture of m-xylene (2.0 mL), $B_2pin_2$ (30.0 mg, 118.1 μmol) and bpy-UiO-Ir (5.1 mg, 1.0 mol % Ir) were charged into a storage tube. The tube was sealed and heated at 100° C. for 2 h. The solid catalyst was separated via centrifugation. The extract was concentrated in vacuo and purified by preparative TLC (Hexane:EtOAc=9:1) to give 5-(4,4,5,5-tetramethyl-1,3,2-dioxaborolan-2-yl)-m-xylene in 46% yield.

As shown in Scheme 8b), a mixture of m-xylene (2.0 mL), $B_2pin_2$ (30.0 mg, 118.1 μmol) and bpy-UiO-Ir (5.1 mg, 1.0 mol % Ir) were heated into a storage tube at 100° C. for 2 h. The solid catalyst was separated via centrifugation and the supernatant was filtered through a celite. Then, the supernatant was stirred at 100° C. for an additional 13 h. The extract was concentrated in vacuo and purified by preparative TLC (Hexane:EtOAc=9:1) to give 5-(4,4,5,5-tetramethyl-1,3,2-dioxaborolan-2-yl)-m-xylene in 47% yield. These two reactions afforded almost the same yields.

Time Evaluation Studies for C—H Borylation of m-xylene Using bpy-UiO-Ir and [($CO_2Me$)$_2$bpy]Ir(COD)(OMe) as Catalysts Under Identical Conditions:

Two storage tubes, one was charged with m-xylene (2.0 mL), $B_2pin_2$ (42.1 mg, 165.8 μmol), bpy-UiO-Ir (3.5 mg, 0.5 mol % Ir), and another was charged with m-xylene (2.0 mL), $B_2pin_2$ (42.1 mg, 165.8 μmol) and [($CO_2Me$)$_2$bpy]Ir(cod)(OMe) (1.0 mg, 1.66 μmol, 0.5 mol % Ir) in a glovebox. The two storage tubes were heated at 100° C. simultaneously and the conversion (%) of the product was monitored by GC by withdrawing aliquots from the reaction mixture using mesitylene as an internal standard in 1 h interval of heating.

Figure 2A:
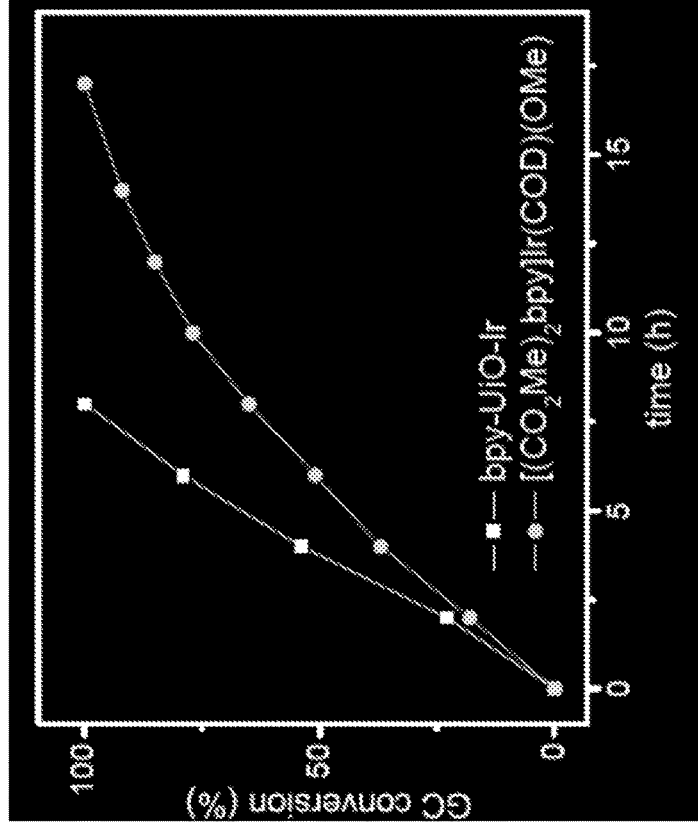
FIG. 2A is a graph showing plots for conversion (percentage, %, as measured by gas chromatography (GC)) versus time (hours, h) for the C—H borylation of m-xylene catalyzed by a metal-organic framework (MOF)-based catalyst comprising bipyridine bridging ligands and zirconium-oxo clusters and metalated with iridium, i.e., bpy-UiO-Ir (squares). For comparison, data is also shown for the reaction catalyzed by a homogeneous catalyst, i.e., [CO$_2$Me)$_2$ bpy]Ir(COD)(OMe) (circles). Reactions were performed using 0.5 mole % of catalyst.

Discussion:

Bpy-UiO-Ir exhibited excellent activity in dehydrogenative borylation of aromatic C—H bonds using $B_2(pin)_2$ as the borylating agent. Borylation of aryl C—H bonds provides aryl boronic esters, which are employed as reagents in many important reactions for synthesizing organic compounds. See Hayashi et al., Chem. Rev., 2003, 103, 2829; Maleczka et al., J. Am. Chem. Soc., 2003, 125, 7792; Murphy et al., J. Am. Chem. Soc., 2007, 129, 15434; Tzschucke et al., Org. Lett., 2007, 9, 761; Beck et al., Angew. Chem. Int. Ed., 2008, 47, 3004; and Kikuchi et al., Tetrahedron, 2008, 64, 4967. Bpy-UiO-Ir catalyzed borylation reactions with $B_2(pin)_2$ were first screened in several solvents and in neat arenes (without using a solvent) to obtain the best conditions of 100° C. in heptane or in neat arenes. At 0.5 mol % catalyst loading, bpy-UiO-Ir gave complete conversions and afforded the borylated arenes in 85-96% isolated yields. See Table 2. MOF-catalyzed borylation reactions have a broad substrate scope, allowing the borylation of a wide range of activated and unactivated arenes, including halogenated-, alkyl-, and alkoxy-arenes. The regioselectivities of the borylated products are the same as those reported for the homogeneous catalysts by functionalizing the α-C centers in heteroarenes and the least sterically hindered carbon centers in unactivated arenes. See Ishiyama et al., Angew Chem, Int. Ed., 2002, 295, 305. The C—H borylation of rigid and larger substrates required longer reaction times due to the slower diffusion of substrates and products through the MOFs channels (see Table 2; Entries 1, 3 and 4). Time-dependent GC conversion curves indicated that, in spite of slower diffusion of reactants through MOF channels than in homogeneous solution, bpy-UiO-Ir was at least twice as active as the homogeneous control [($CO_2Me$)$_2$ bpy]-Ir(COD)(OMe) in terms of turnover frequency. See FIG. 2A. At 0.5 mol % catalyst loading, the borylation of m-xylene was completed in 8 and 17 h for bpy-UiO-Ir and [($CO_2Me$)$_2$bpy]Ir(COD)(OMe), respectively. See FIG. 2A. The higher activity of bpy-UiO-Ir is presumably due to active site isolation which prevents any intermolecular deactivation pathways.

TABLE 2

Bpy-UiO-Ir catalyzed C—H borylation of arenes.[a]

$$2\ Ar-H + \text{B}_2\text{pin}_2 \xrightarrow[\substack{100°\ C. \\ -H_2}]{\text{bpy-UiO-Ir} \\ 0.1\text{-}0.5\ \text{mol\%\ cat.}} 2\ Ar-\text{Bpin}$$

| Entry | Arene | Product | Time | Isolated Yield (%) |
|---|---|---|---|---|
| 1 | indole | 2-Bpin indole | 28 h | 85 |
| 2 | indole | 2-Bpin indole | 4 d | 83[b] |
| 3 | 1-Br-3-I-benzene | 1-Br-3-I-5-Bpin-benzene | 12 h | 86 |
| 4 | 1,2-(OMe)$_2$-benzene | 1,2-(OMe)$_2$-4-Bpin-benzene | 10 h | 93 |
| 5[c] | o-xylene | 4-Bpin-o-xylene | 9 h | 96 |
| 6[c] | o-xylene | 4-Bpin-o-xylene | 4 d | 96[b] |
| 7[c] | m-xylene | 5-Bpin-m-xylene | 7 h | 94 |
| 8[c] | 1,2-Cl$_2$-benzene | 4-Bpin-1,2-Cl$_2$-benzene | 8 h | 93 |
| 9[c] | 1,2-Cl$_2$-benzene | 4-Bpin-1,2-Cl$_2$-benzene | 4 d | 95[b] |

TABLE 2-continued

Bpy-UiO-Ir catalyzed C—H borylation of arenes.[a]

| Entry | Arene | Product | Time | Isolated Yield (%) |
|---|---|---|---|---|
| 10 | Cl-C6H4-Cl | Cl-C6H3(Bpin)-Cl | 17 h | 91 |
| 11[c] | toluene | Bpin-toluene | 15 h | 93 (o:m:p = 0:60:40) |

Reaction conditions: 0.5 mol % bpy-UiO-Ir, 81.9 μmol B2pin2, 163.9 μmol arene, 2.0 ml heptane, 100° C. [b]0.1 mol % bpy-UiO-Ir. [c]Neat arene was used.

Figure 2B:
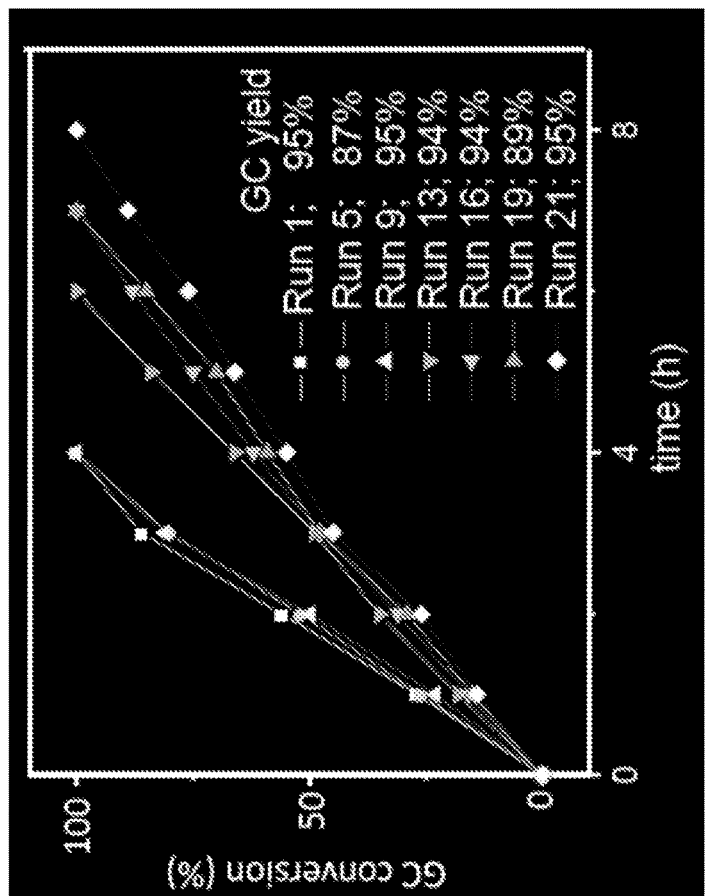
FIG. 2B is a graph showing plots for conversion (percentage, %, as measured by gas chromatography (GC)) versus time (hours, h) for the C—H borylation of m-xylene catalyzed by a metal-organic framework (MOF)-based catalyst comprising bipyridine bridging ligands and zirconium-oxo clusters and metalated with iridium, i.e., bpy-UiO-Ir. Data is shown for the initial use of the catalyst (i.e., run 1, squares), as well as for reuse of the catalyst for the fifth, ninth, thirteenth, sixteenth, nineteenth, or twenty-first times (run 5, circles; run 9, triangles; run 13, inverted triangles; run 16, triangles pointing left; run 19, triangles pointing right; and run 21, diamonds).

Remarkably, at a 2 mol % catalyst loading, bpy-UiO-Ir could be recovered and reused for the borylation of m-xylene for at least 20 times without significant loss of catalytic activity (see FIG. 2B) or MOF crystallinity. See FIG. 1G. Excellent yields (87-95%) of the borylated product, 5-(4,4,5,5-tetramethyl-1,3,2-dioxaborolan-2-yl)-m-xylene, were obtained consistently in the reuse experiments. $B_2(pin)_2$ was completely consumed within four hours during the first 9 runs, but the reaction took progressively longer time to complete starting from the 13$^{th}$ run. See FIG. 2B. The reaction took 6 h to complete in the 13$^{th}$ run and 8 h in the 21$^{st}$ run. Without being bound to any one theory, the slightly longer reaction time needed for the later runs is presumably due to the accidental loss of the MOF catalyst during the work up step (due to the small reaction scale). The bpy-UiO-Ir catalyst thus gives higher total turnover number (at least 20 times) as result of catalyst recycling and reuse. Importantly, the borylation product was obtained in high purity simply by removing the solid catalyst and the organic volatiles. The heterogeneous nature of bpy-UiO-Ir was further confirmed by several experiments. The PXRD patterns of bpy-UiO-Ir recovered from the 5th, 9$^{th}$ and 21$^{st}$ run remained essentially unchanged from that of freshly prepared bpy-UiO-Ir (see FIG. 1G), indicating that the MOF catalyst is very stable under the catalytic conditions. Additionally, ICP-MS analyses showed that the amounts of Ir and Zr leaching into the supernatant after the 1st run were <0.03% and <0.003%, respectively, and the amounts of leached Ir and Zr after the 9$^{th}$ run were <0.01% and <0.001%, respectively. Moreover, no further conversion was detected after removal of bpy-UiO-Ir during the course of the borylation reaction.

Example 4

Arene Ortho-Silylation Catalyzed by Bipyridine MOF Catalysts

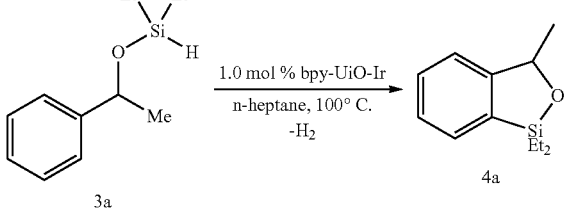

Scheme 9
Exemplary Arene Ortho-Silylation Reaction Catalyzed by a Bipyridine MOF Catalyst.

Exemplary Procedure for bpy-UiO-Ir Catalyzed Ortho-Silylation of Arenes:

As shown in Scheme 9, in a glovebox, diethyl(hydrido) silyl ether (3a, 17.0 mg, 81.6 μmol), bpy-UiO-Ir (1.6 mg, 1.0 mol % Ir) and 2.0 mL n-heptane were charged into a storage tube. The tube was sealed and heated at 100° C. for 30 h. The reaction mixture was cooled to room temperature and the solid was centrifuged out of suspension in the glovebox. The solid was extracted with n-heptane 2-3 times and it can be recycled and reused. The combined organic extracts were concentrated in vacuo and purified by silica gel preparative TLC yielding benzoxasilole (4a, 15.8 mg, 76.8 μmol, 94.1%).

Table 3 shows how the reaction conversion percentage (%) varied by reaction solvent, temperature, and time.

TABLE 3

Conversion (%) under different solvents, temperatures and reaction times for catalytic arene ortho-silylation.[a]

| Entry | Ir loading (mol %) | Solvent | Temperature (° C.) | Time | Conversion (%)[b] |
|---|---|---|---|---|---|
| 1 | 1.0 | THF | 80 | 40 h | 100 |
| 2 | 1.0 | heptane | 100 | 27 h | 100 |
| 3 | 0.1 | heptane | 100 | 6 d | 100 |
| 4 | 1.0 | n-octane | 100 | 48 h | 41 |

[a]Reaction conditions: 160 μmol substrate, 1.0 ml solvent.
[b]Conversion was determined by GC analysis.

Time Evaluation Studies for Ortho-Silylation of Arenes Using bpy-UiO-Ir and [(CO$_2$Me)$_2$bpy]Ir(COD)(OMe) as Catalysts Under Identical Conditions:

Diethyl(hydrido)silyl ether (3a, 280 mg, 1.39 mmol), bpy-UiO-Ir (3 mg, 0.1 mol % Ir) and n-heptane (2.0 mL) were charged into a storage tube in a glovebox. Another tube was charged with 3a (280 mg, 1.39 mol), [(CO$_2$Me)$_2$ bpy]Ir(COD)(OMe) (42 mg, 69.57 μmol, 5.0 mol % Ir) and n-heptane (2.0 mL). The two storage tubes were heated at 100° C. simultaneously and the conversion (%) of the product was monitored by GC using mesitylene as an internal standard in 1 d interval of heating.

Figure 2C:
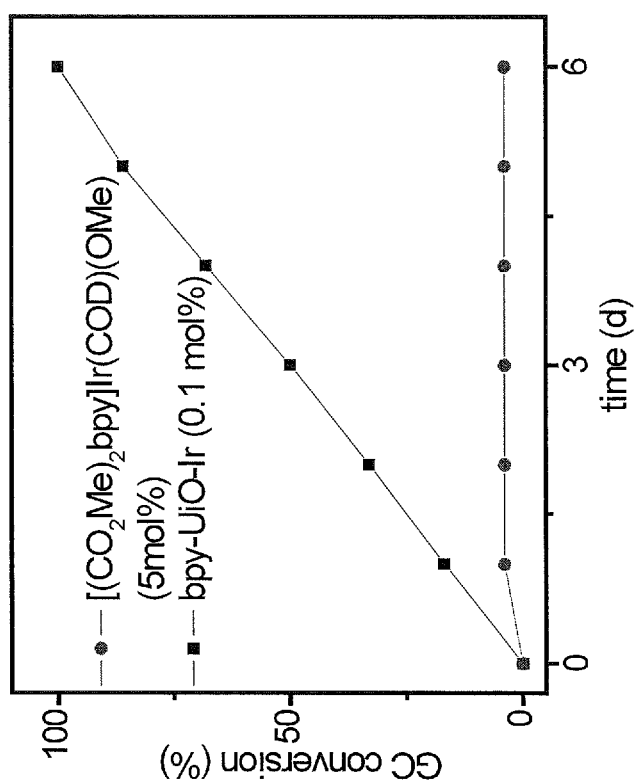
FIG. 2C is a graph showing plots for conversion (percentage, %, as measured by gas chromatography (GC)) versus time (hours, h) for the ortho-silylation of diethyl (hydrido)silyl ether catalyzed by a metal-organic framework (MOF)-based catalyst comprising bipyridine bridging ligands and zirconium oxoclusters and metalated with iridium, i.e., bpy-UiO-Ir, (0.1 mole percentage catalyst; squares). For comparison, data is also shown for the reaction catalyzed using a homogeneous catalyst, i.e., [CO$_2$Me)$_2$bpy]Ir(COD)(OMe) (5 mole percentage catalyst; circles).

Discussion:

Bpy-UiO-Ir is active in catalyzing intramolecular ortho-silylation of benzylicsilyl ethers to give benzoxasiloles. See Table 4. Benzoxasiloles are important in organic synthesis and can be converted to phenol by Tamao-Fleming oxidation (see Jones et al., Tetrahedron, 1996, 52, 7599) or to biaryl derivatives by Hiyama cross-coupling reactions. See Denmark, Acc. Chem. Res., 2002, 35, 835. Screening experiments of solvents and reaction conditions revealed that the silylation reaction gave the highest turnover frequency when performed in n-heptane at 100° C. See Table 3. At 1.0 mol % catalyst loading and under this optimized condition, bpy-UiO-Ir provided benzoxasiloles (4a-4e) in good isolated yields (83-94%). No hydrogen acceptor is needed for the silylation reaction, which is an improvement over the corresponding homogeneous silylation reaction in terms of atom efficiency. The catalyst loading could be decreased to 0.1 mol %, albeit at the cost of increasing the reaction time from 30 h to 6 days. See Table 4, Entries 2 & 4. Additionally, longer reaction times were required for larger substrates, presumably because of the slower substrate diffusion through the MOF channels. See Table 4; Entries 5-7. Notably, the homogeneous control [(CO$_2$Me)$_2$bpy]Ir(COD)(OMe) had a relatviely low activity for the silylation reaction. Under identical conditions, 5.0 mol % of [(CO$_2$Me)$_2$bpy]Ir(cod)(OMe) afforded 4a in only 4% conversion in a day, after which no further conversion was observed with prolonged heating. In contrast, the conversion of 4a proceeded linearly with time until completion in the presence of at 0.1 mol % of the bpy-UiO-Ir catalyst. See FIG. 2C. This result indicates that bpy-UiO-Ir is at least 1250 times more active than the homogeneous control for the silylation reaction, supporting the beneficial effect of active site isolation in a MOF catalyst. The PXRD of bpy-UiO-Ir recovered from the silylation reaction remained the same as that of freshly prepared bpy-UiO-Ir. All of these results indicate that bpy-UiO-Ir is a robust, reusable, and active single-site solid catalyst for important organic transformations.

TABLE 4

Bpy-UiO-Ir catalyzed intramolecular ortho-silylation of benzylicsilyl ethers to benzoxasiloles.[a]

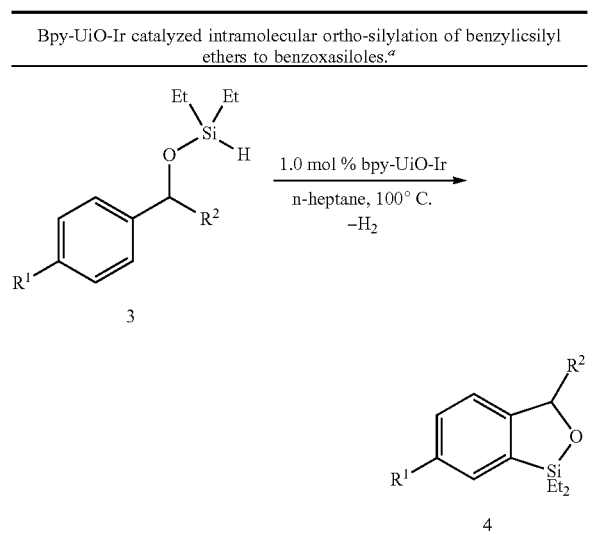

| Entry | R$^1$ | R$^2$ | Time | Yield[b] |
|---|---|---|---|---|
| 1 | H | Me | 30 h | 94 |
| 2 | H | Me | 6 d | 90 [c] |
| 3 | Me | Me | 30 h | 92 |
| 4 | Me | Me | 6 d | 91 [c] |
| 5 | OMe | Me | 50 h | 85 |
| 6 | Cl | Me | 44 h | 92 |
| 7 | H | Ph | 72 h | 83 |

[a]Reaction conditions: 1.0 mol % bpy-UiO-Ir, 2.0 ml n-heptane, 100° C. [b]Isolated yield. [c]0.1 mol % bpy-UiO-Ir.

Example 5

Dehydrogenation of Cyclohexenones with Bipyridine MOF Catalysts

Scheme 10. Exemplary Dehydrogenation of a Cyclohexenone Catalyzed by a Bipyridine MOF Catalyst.

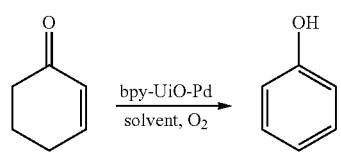

Exemplary Procedure for bpy-UiO-Pd Catalyzed Dehydrogenation of Substituted Cyclohexenones to Phenols:

3-methylcyclohex-2-enone (5b, 20.1 mg, 182.5 µmol), bpy-UiO-Pd (5.0 mg, 1.0 mol % Pd) and DMSO (2.0 mL) were charged into a vial containing a stir bar. The vial was sealed with a rubber septum and O$_2$ was bubbled through the suspension for 15 min via a syringe needle through the septum. Then, the mixture was heated at 100° C. in an oil bath with slow stirring for 35 h under O$_2$ atmosphere. The reaction mixture was cooled to room temperature and the solid was centrifuged out of suspension. The solid was extracted with DMSO two times and the combined organic extracts were concentrated in vacuo and purified by silica gel preparative TLC to give m-cresol (6b, 17.0 mg, 156.9 µmol, 86.0%).

Scheme 10 shows an exemplary dehydrogenation reaction that can be catalyzed by the presently disclosed MOFs. Table 5 shows how the reaction conversion percentage (%) varied by reaction solvent, temperature, and time.

TABLE 5

Conversion (%) under different solvents, temperatures and reaction times for the bpy-UiO-Pd catalyzed dehydrogenation of cyclohexenone to phenol using O$_2$.[a]

| Entry | Pd loading (mol %) | Solvent | Temperature (° C.) | Time | Conversion (%)[b] |
|---|---|---|---|---|---|
| 1 | 1.2 | toluene | 80 | 3 d | 46 |
| 2 | 1.2 | DMSO | 80 | 55 h | 100 |
| 3 | 1.2 | DMSO | 100 | 30 h | 100 |
| 4 | 1.2 | DMSO | 120 | 30 h | 64 |
| 5 | 1.2 | DMF | 100 | 3 d | 62 |
| 6 | 1.2 | m-xylene | 100 | 3 d | 39 |
| 7 | 1.0 | DMSO | 100 | 32 h | 100 |
| 8 | 0.5 | DMSO | 100 | 30 h | 32 |

[a]Reaction conditions: 1.0 ml solvent, 1 atm O$_2$.
[b]Conversion was determined by GC analysis.

Discussion:

Since the homogeneous catalyst [(6,6'-dmbpy)Pd(CH$_3$CN)$_4$][BF$_4$]$_2$ (6,6'-dmbpy=6,6'-dimethyl-2,2'-bipyridine) was recently shown by Stahl and coworkers to be a highly active catalyst for dehydrogenation of substituted cyclohexenones (see Izawa et al., Science, 2011, 333, 209; and Izawa et al., Angew. Chem. Int. Ed., 2013, 52, 3672, the ability of the presently disclosed heterogeneous catalysts was also studied. Bpy-UiO-Pd is active in dehydrogenation of substituted cyclohexenones to phenol under 1 atm of O$_2$. The reaction conditions were optimized by monitoring the conversion of cyclohexenone to phenol (6a) with 1.0 mol % bpy-UiO-Pd by GC analysis. Phenol could be obtained in moderate yields (39-80%) in DMF and aromatic solvents such as toluene and m-xylene at 80-100° C. The highest yield (93%) was obtained when the reaction was performed in DMSO at 100° C. However, the yield of phenol dropped significantly in DMSO at 120° C. even though the MOF catalyst remained crystalline, presumably due to the decomposition of the bpy-UiO-Pd catalyst. Under 1 atm of $O_2$, 1.0 mol % bpy-UiO-Pd afforded 3-substituted phenols 6b, 6c, and 6d (see Table 6, Entries 6, 7 & 8) in DMSO at 100° C. in 83-91% isolated yields. Bpy-UiO-Pd also compares favorably to its homogeneous counterpart, with at least three times as high activity as the homogeneous control. The homogeneous catalyst[{$(CO_2Me)_2$bpy}$Pd(CH_3CN)_4$][$BF_4$]$_2$ that was prepared in situ from $(CO_2Me)_2$bpy and [$Pd(CH_3CN)_4$][$BF_4$]$_2$ (1:1 equiv; 3 mol % Pd) afforded phenol quantitatively from cyclohexenone in 36 h in DMSO at 100° C. During the course of this reaction, a black precipitate formed due to the degradation of the catalyst. After removal of all the volatiles in vacuo, the remaining residue from the homogeneous reaction did not exhibit any catalytic activity for the dehydrogenation of cyclohexenone. In contrast, bpy-UiO-Pd was recycled and reused for twice in this reaction ($1^{st}$ run: 93%; $2^{nd}$ run: 91%; $3^{rd}$ run 79%). The bpy-UiO-Pd catalyst recovered from the dehydrogenation reaction showed the same PXRD pattern as the as-prepared bpy-UiO-Pd, indicating that the bpy-UiO-Pd catalyst is stable under the catalytic conditions.

TABLE 6

Bpy-UiO-Pd catalyzed dehydrogenation of substituted cyclohexenones to phenols.[a]

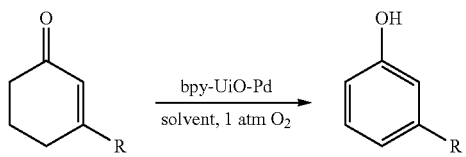

| Entry | R | Solvent | Temp. (° C.) | Time | Conv. (%)[b,c] |
|---|---|---|---|---|---|
| 1 | H | toluene | 80 | 3 d | 80 |
| 2 | H | DMSO | 80 | 55 h | 100 |
| 3 | H | m-xylene | 100 | 3 d | 39 |
| 4 | H | DMSO | 100 | 32 h | 100 (93) |
| 5 | H | DMF | 100 | 3 d | 82 |
| 6 | Me | DMSO | 100 | 35 h | 100 (86) |
| 7 | Et | DMSO | 100 | 44 h | 100 (91) |
| 8 | Ph | DMSO | 100 | 70 h | 100 (83) |

[a]Reaction conditions: 1.0 mol % bpy-UiO-Pd. [b]Conv. were determined by GC. [c]Isolated yield in the parentheses.

Example 6

First Row Transition Metal MOF Catalysts and Their Catalysis of Olefin Hydrogenation MOF catalysts metalated with first-row transition metals, e.g., bpy-UiO-Fe, bpy-UiO-Co and bpy-UiO-Ni, were prepared by first metalating bpy-UiO with solutions of the corresponding metal salts and then activating with $NaBEt_3H$ (superhydride) solution. The resulting solids were active for olefin hydrogenation reactions (see Scheme 11) with a low catalyst loading. See Table 7.

Scheme 11
Olefin Hydrogenation Reactions Catalyzed by MOF Catalysts.

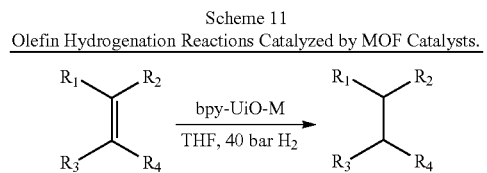

TABLE 7

Bpy-UiO-M (M = Fe, Co, Ni) catalyzed olefin hydrogenation.

| Entry | Metal | Olefin | Loading | Time | Conv. (%) |
|---|---|---|---|---|---|
| 1 | Fe | 1-octene | 0.15% | 18 h | 100 |
| 2 | Co | 1-octene | 0.04% | 18 h | 100 |
| 3 | Ni | 1-octene | 0.04% | 18 h | 100 |
| 4 | Fe | α-methylstyrene | 0.5% | 18 h | 100 |
| 5[a] | Fe | α-methylstyrene | 0.5% | 18 h | 100 |
| 6 | Co | α-methylstyrene | 0.5% | 18 h | 100 |
| 7[a] | Co | α-methylstyrene | 0.5% | 18 h | 100 |
| 8 | Fe | Styrene | 0.1% | 18 h | 57 |
| 9 | Co | Styrene | 0.1% | 18 h | 100 |

[a]Recycle Studies

Example 7

Elongated and Mixed Ligand MOFs

MOFs containing a mixture of two different bridging ligands, 4,4'-biphenyldicarboxylic acid ($H_2$BPDC) and 2,2'-bipyridine-5,5'-dicarboxylic acid ($H_2$BPYDC), were prepared in order to increase the channel sizes and to maximize the efficiency of ligand usage. See Scheme 14, below. Crystallinity of this mix-ligand MOF has been verified by powder X-ray diffraction. MOFs based on elongated bpy-derived and phenanthroline-derived ligands 5,5'-bis(carboxyvinyl)-2,2'-bipyridine ($H_2$BPVDC; prepared as shown in Scheme 12, below) and 3,8-bis(4-carboxyphenyl)-1,10-phenanthroline ($H_2$PTPDC; prepared as shown in Scheme 13, below) were also prepared (see Scheme 14) in order to increase the channel sizes and to accelerate the substrate diffusion through MOF channels. Crystalline materials were obtained.

Scheme 12
Synthesis of ligand 5,5'-bis(carboxyvinyl)-2,2'-bipyridine (H₂BPVDC).
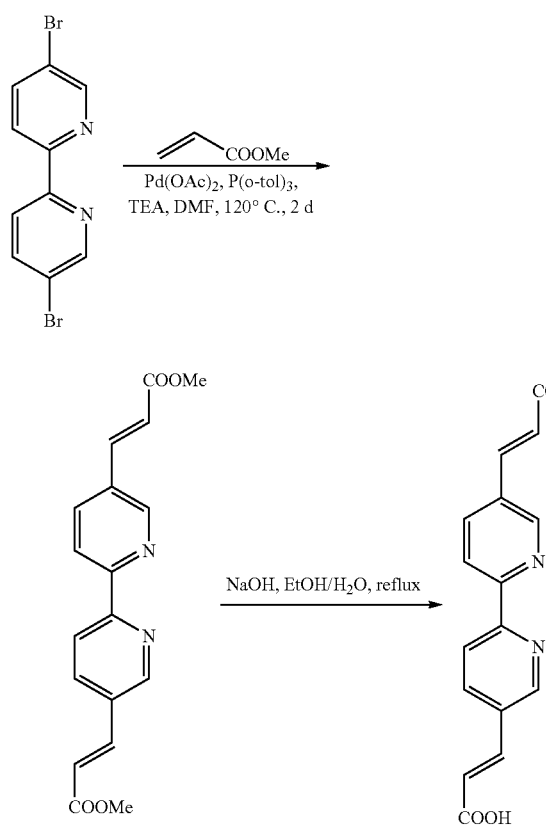
Scheme 13
Synthesis of ligand 3,8-bis(4-carboxyphenyl)-1,10-phenanthroline (H₂PTPDC).
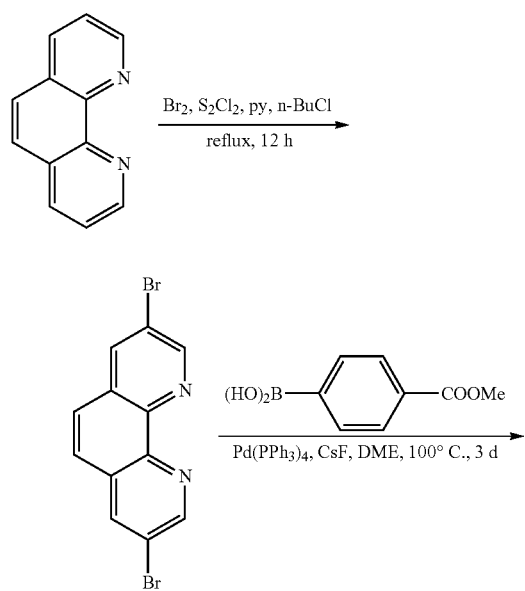
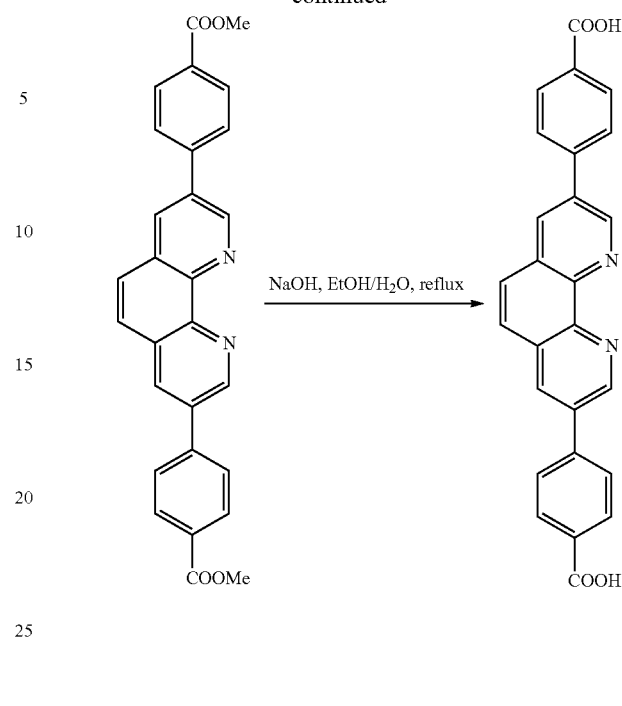
Scheme 14
Synthesis of MOFs containing the mixed ligands and elongated ligands.
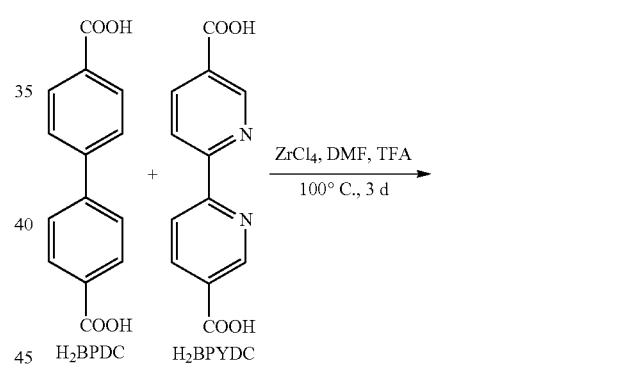
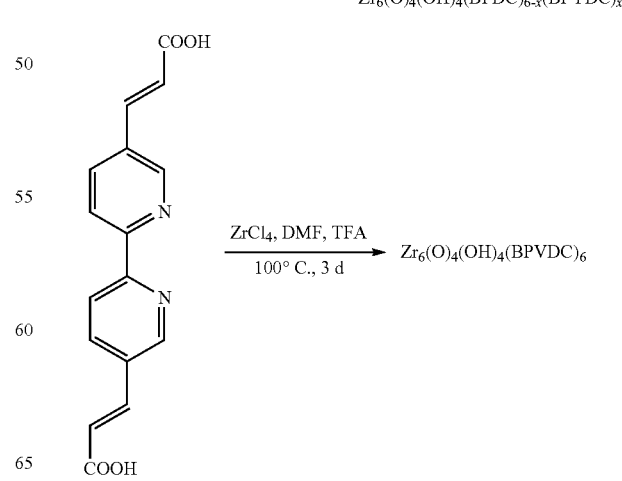

-continued

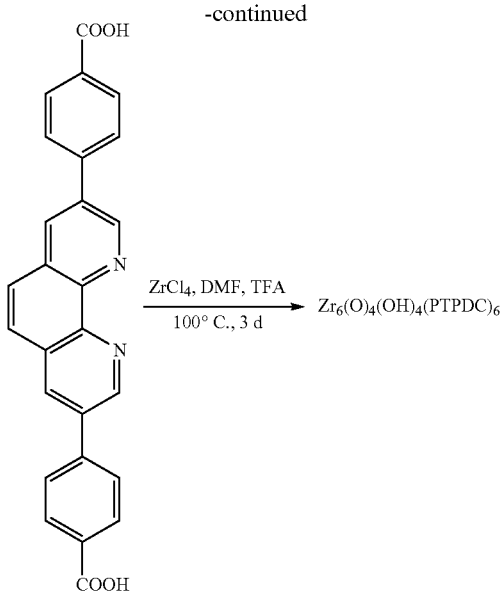

Example 8

MOFs with Salicylaldimine-Based Bridging Ligands

An MOF comprising a salicylaldimine-based bridging ligand ($H_2$SALI-TPD) was prepared. The synthesis of ligand was accomplished as shown in Scheme 15. Hydrothermal reactions between $H_2$SALI-TPD and $ZrCl_4$ led to crystalline SALI-MOF. PXRD studies indicated that SALI-MOF remained crystalline upon treatment with $FeCl_3$ to form SALI-MOF-Fe as comparative to the crystalline MOF, i.e., UiO-68-$NH_2$, that is composed of $Zr_6(\mu_3\text{-}O)_4(\mu_3\text{-}OH)_4$ SBUs and amino-terphenyldicarboxylated bridging ligands. Nitrogen surface area measurements indicated that SALI-MOF is highly porous with a BET surface area of 3330 $m^2/g$. Upon treatment with $NaBEt_3H$ in THF, we found that the SALI-MOF-Fe is highly active in alkene hydrogenation reactions, with a TON of >30,000. See Table 8.

Exemplary Procedure for SALI-MOF-Fe Catalyzed Hydrogenation of Olefins:

In a glovebox, SALI-MOF-Fe in THF (3.0 mg, 0.1 mol % Fe) was quickly weighed onto a filter paper, charged into a small vial and 1 mL THF was added. Then, 15 μL $NaEt_3BH$ (1.0 M in THF) was added to the vial and the mixture was stirred slowly for 1 h in the glovebox. During stirring, the solid became greenish black. The solid was centrifuged out of suspension and washed with THF 2-3 times. Then, the solid in 1 ml THF was transferred to a vial and olefin (1.56 mmol) was added. The vial was placed into a Parr pressure reactor in a nitrogen-filled glovebox. The reactor was then pressurized to 40 bar. After stirring at room temperature for 15-24 h, the solid was centrifuged out of suspension and extracted 2-3 times with THF. The combined organic extracts were concentrated in vacuo and purified either by silica gel preparative TLC or fractional distillation to yield the pure product.

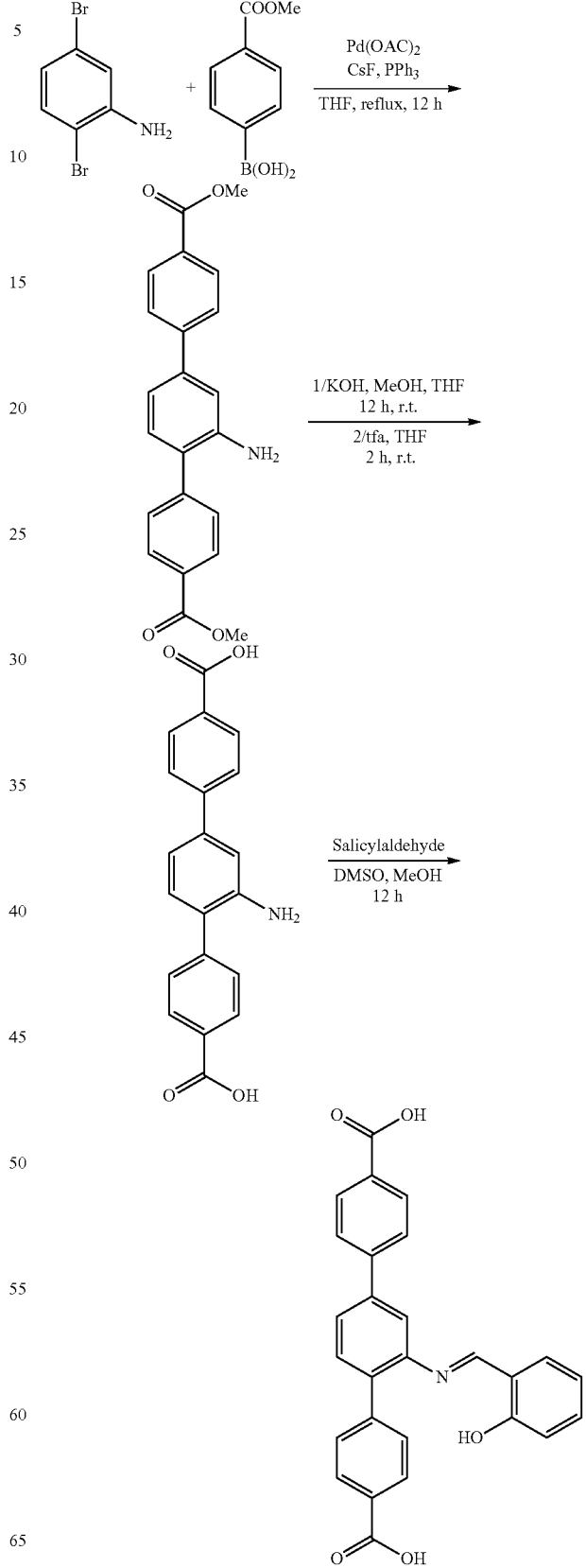

Scheme 15
Synthesis of ligand $H_2$SALI—TPD.

TABLE 8

SALI-MOF-Fe catalyzed hydrogenation reactions.

| Entry | Olefin | Product | Time (h) | Yield (%) |
|---|---|---|---|---|
| 1 | 1-octene | octane | 15 | 100 |
| 2 | 1-octene | octane | 18 | 100[b] |
|   |        |        | 24 | 30[c] |
| 3 | α-methylstyrene | isopropylbenzene | 18 | 100 |
| 4 | α-methylstyrene | isopropylbenzene | 18 | 95[b] |
| 5 | cis-β-methylstyrene | propylbenzene | 18 | 12 |
| 6 | cyclohexene | cyclohexane | 18 | 100 |
| 7 | 4-methoxyallylbenzene | 4-methoxypropylbenzene | 18 | 100 |
| 8 | diallyl ether | allyl propyl ether | 24 | 100 |
| 9 | styrene | ethylbenzene | 18 | 100 |
| 10 | styrene | ethylbenzene | 24 | 45[c] |

[a]Reaction conditions: 3.0 mg Uio-68-Fe (0.1 mol % Fe), 15 μL NaBEt$_3$H (1.0 M in THF), 1.84 mmol alkene, 0.5 ml THF, 40 atm H$_2$, 23° C. [b]0.01 mol % Fe. [c]0.001 mol % Fe.

Example 9

Metal-Organic Frameworks as Highly Efficient, Broad Scope Catalysis with Solution-Inaccessible Bipyridine-Co⁰ Complexes This Example discloses highly robust and active single-site solid catalysts based on cobalt complexes via postsynthetic metalation of bipyridyl- or phenanthryl-containing metal-organic frameworks (MOFs) of UiO structures. These MOF-Co catalysts are highly active in alkene hydrogenation and hydroboration, aldehyde/ketone hydroboration, and arene C—H borylation, as example. In alkene hydrogenation, the MOF catalysts displayed high turn-over numbers (TONs) of up to 1,200,000 and can be recycled and reused more than 15 times. Of note, the MOFs catalysts are more active and stable compared to their homogeneous controls, indicating the role of MOF frameworks in preventing intermolecular deactivation of reactive metal-sites. The presently disclosed MOFs thus provide sustainable chemical synthesis with base metal catalysts. Shown in this Example are MOFs containing orthogonal bipyridyl- and phenanthroline-derived ligands that can be readily metalated with Co(II) chlorides to afford highly active and reusable single-site solid catalysts for a broad scope of organic transformations.

Results and Discussion:

Two bipy-containing UiO MOFs, bpy-MOF and bpyv-MOF, were constructed from $Zr_6O_4(OH)_4(RCO_2)_{12}$ secondary building units (SBUs) and 2,2'-bipyridyl-5,5'-dicarboxylate (bpy) or 3,3'-(2,2'-bipyridyl-5,5'-diyl)diacrylate (bpyv) bridging ligands, respectively. UiO-type MOFs are stable under a variety of catalytic conditions (Falkowski, J. M.; et al., J. Am. Chem. Soc. 2014, 136, 5213; Fei, H.; Cohen, S. M. Chem Commun 2014, 50, 4810; Manna, K.; Zhang, T.; Carboni, M.; Abney, C. W.; Lin, W. J. Am. Chem. Soc. 2014, 136, 13182; Cavka, J. H.; Jakobsen, S.; Olsbye, U.; Guillou, Lamberti, C.; Bordiga, S.; Lillerud, K. P. J. Am. Chem. Soc. 2008, 130, 13850; Kandiah, M.; Nilsen, M. H.; Usseglio, S.; Jakobsen, S.; Olsbye, U.; Tilset, M.; Larabi, C.; Quadrelli, E. A.; Bonino, F.; Lillerud, K. P. Chemistry of Materials 2010, 22, 6632; Schaate, A.; Roy, P.; Godt, A.; Lippke, J.; Waltz, F.; Wiebcke, M.; Behrens, P. Chemistry—A European Journal 2011, 17, 6643; Schaate, A.; Roy, P.; Preuβe, T.; Lohmeier, S. J.; Godt, A.; Behrens, P. Chemistry—A European Journal 2011, 17, 9320; Wang, C.; Xie, Z. G.; deKrafft, K. E.; Lin, W. L. J. Am. Chem. Soc. 2011, 133, 13445; Wang, C.; Wang, J.-L.; Lin, W. J. Am. Chem. Soc. 2012, 134, 19895). Heating a mixture of the dicarboxylic acid ligand and ZrCl$_4$ in presence of trifluoroacetic acid in DMF at 100° C. afforded bpy-MOF and bpyv-MOF in ~65% yield. Single crystal structure of bpy-MOF has been previously reported (Li, L.; Tang, S.; Wang, C.; Lv, X.; Jiang, M.; Wu, H.; Zhao, X. Chem Commun 2014, 50, 2304).

Despite the bending nature of the bpyv linker, bpyv-MOF adopts the typical UiO structure with the cubic space group Fm-3m as revealed by single-crystal X-ray diffraction studies. Phase purity of the bulk samples was examined via powder X-ray diffraction (PXRD) studies. PXRD patterns of bulk bpyv-MOF showed several unexpected peaks, which can be attributed to structure distortion in nanoscale MOFs (He, C.; Lu, K.; Liu, D.; Lin, W. *J. Am. Chem. Soc.* 2014, 136, 5181). Post-synthetic metalation of bpy-MOF, bpyv-MOF, and MPT-MOF with 8 equiv. of $CoCl_2$ afforded MOF-Co materials as green-blue solids. PXRD patterns showed that bpy-MOF-Co, bpyv-MOF-Co, and mPT-MOF-Co remained crystalline, whereas inductively coupled plasma-mass spectrometry (ICP-MS) analyses of the digested metalated MOF samples revealed Co loading of 86%, 92%, and 12% for bpy-MOF-Co, bpyv-MOF-Co, and mPT-MOF-Co, respectively. Nitrogen sorption experiments revealed a BET surface area of 764 $m^2/g$ for bpy-MOF-Co. The reduced surface areas and pore sizes compared to the bpy-MOF ($S_{BET}$=2277 $m^2/g$) (Manna, K.; Zhang, T.; Lin, W. *J. Am. Chem. Soc.* 2014, 136, 6566; Li, L.; Tang, S.; Wang, C.; Lv, X.; Jiang, M.; Wu, H.; Zhao, X. *Chem Commun* 2014, 50, 2304) indicated presence of Co centers and associated ligands in the MOF cavities. Similarly, bpyv-MOF-Co exhibited a BET surface area of 294 $m^2/g$. In comparison, the BET surface area for bpyv-MOF is 373 $m^2/g$. The low surface areas for bpyv-MOF materials are likely caused by framework distortion upon solvent removal, which is not uncommon in MOFs with large channel sizes (Ferey, G.; Serre, C. *Chem Soc Rev* 2009, 38, 1380).

Figure 3:
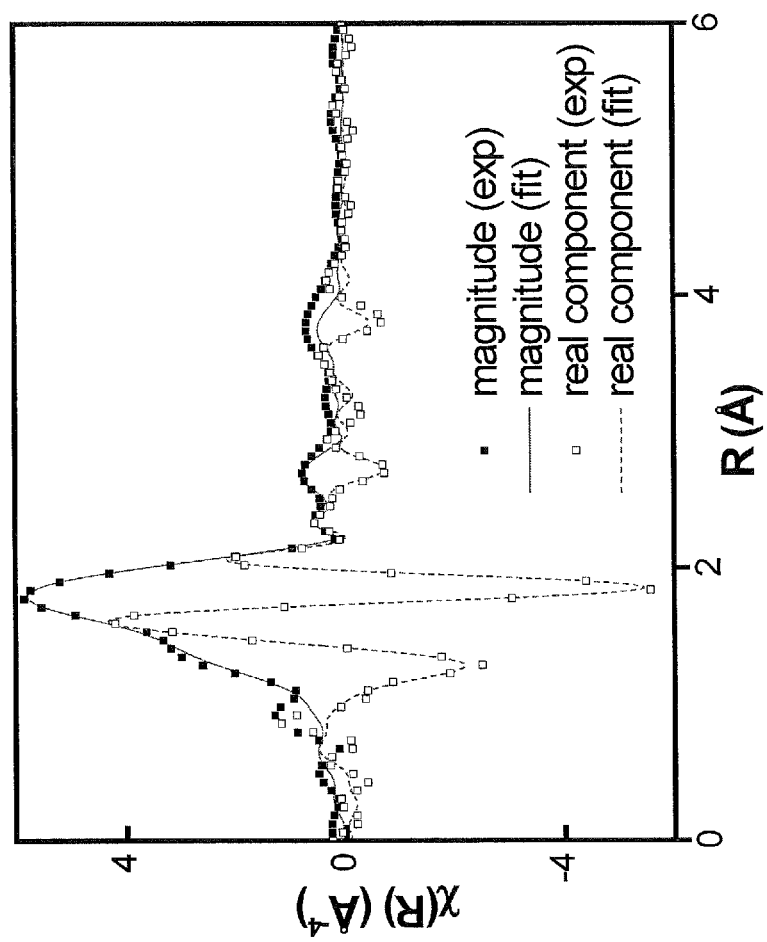
FIG. 3 shows EXAFS spectra and the fits in R-space at the Co K-edge of bpyv-MOF-Co showing the magnitude (solid squares, solid line) and real component (hollow squares, dash line) of the Fourier transform.

As the coordination spheres of Co cannot be characterized by single crystal X-ray diffraction due to intrinsic disorder and incomplete metalation, X-ray absorption spectroscopy (XAS) was relied on to investigate the Co coordination environments. Fitting the extended X-ray absorption fine structure (EXAFS) regions of bpy-MOF-Co and bpyv-MOF-Co X-ray absorption spectra confirmed that the Co centers in the MOFs adopt similar tetrahedral coordination environments as the model complex $Co(Me_2bpy)Cl_2$ ($Me_2bpy$=6,6'-dimethyl-2,2'-bipyridyl) (FIG. 3) (Akbarzadeh Torbati, N.; Rezvani, A. R.; Safari, N.; Saravani, H.; Amani, V. *Acta Crystallographica Section E* 2010, 66, m1284).

Upon treatment with $NaBEt_3H$, bpy-MOF-Co, bpyv-MOF-Co and mPT-MOF-Co became active catalysts for a broad scope of organic transformations including hydrogenation of olefins, hydroboration of alkenes and carbonyl compounds, and direct C—H borylation of arenes. All MOF-Co materials are highly active catalysts for hydrogenation of a range of olefins at room temperature (Table 9). Mono-substituted alkenes such as 1-octene, styrene, and 4-allylanisole were readily hydrogenated within 24 h in quantitative yields using 0.1-0.01 mol % catalysts (entries 1-4 and 8-11, Table 9). At 0.1 mol % Co-loading, bpy-MOF-Co and bpyv-MOF-Co catalyzed hydrogenation of 1,1-, cis-1,2-, and trans-1,2-disubstituted alkenes in 88-100% yields (entries 14-23, Table 9). Additionally, dialkenes such as 1,7-octadiene was completely hydrogenated by mPT-MOF-Co with TON>20,000. In general, the order of catalytic activity of MOF-catalysts in hydrogenation was mPT-MOF-Co>bpyv-MOF-Co>bpy-MOF-Co (e.g, entries 5, 6, 12, and 13, Table 9), presumably due to the larger channel sizes of bpyv-MOF-Co that facilitate the transport of substrates and products. Remarkably, TONs of 195,000 and 210,000 were observed for bpyv-MOF-Co and mPT-MOF-Co with 1-octene as the substrate (e.g., entry 7, Table 9), which is higher than that for previously reported Fe- and Co-functionalized sal-MOF catalysts (Manna, K.; Zhang, T.; Carboni, M.; Abney, C. W.; Lin, W. *J. Am. Chem. Soc.* 2014, 136, 13182). MOF-Co catalysts are also tolerant of carbonyl group. A functionalized alkene, allyl acetate, was hydrogenated to propyl acetate selectively in moderate yield (e.g., entries 24 and 25, Table 9).

Scheme 16

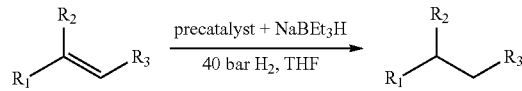

TABLE 9

| | Catalytic Hydrogenation of Olefins[a] | | | | |
|---|---|---|---|---|---|
| Entry | Substrate | Precatalyst | Time | Yield (%) | TONs |
| 1 | | 0.1% bpy-MOF-Co | 20 h | 100 | >1000 |
| 2 | | 0.1% bpyv-MOF-Co | 20 h | 100 | >1000 |
| 3 | | 0.01% bpy-MOF-Co | 20 h | 23 | 10000 |
| 4 | | 0.01% bpyv-MOF-Co | 20 h | 100 | >10000 |
| 5 | | 4 ppm bpyv-MOF-Co | 7 d | 78 | $1.95 \times 10^5$ |
| 6 | | mPT-MOF-Co | 9 d | 66 | $2.1 \times 10^5$ |
| | | 0.1% bpy-MOF-Co | 20 h | 100 | >1000 |
| 9 | | 0.1% bpyv-MOF-Co | 20 h | 100 | >1000 |
| 11 | | 0.01% bpy-MOF-Co | 20 h | 15 | 1500 |
| 12 | | 0.01% bpyv-MOF-Co | 20 h | 100 | >10000 |
| 13 | | 0.01% mPT-MOF-Co | h | 0 | |
| | | 0.01% bpyv-MOF-Co | | | |
| | | 0.01% mPT-MOF-Co | | | |
| 15 | | 0.1% bpy-MOF-Co | 20 h | 100 | >1000 |
| 17 | | 0.1% bpyv-MOF-Co | 20 h | 100 | >1000 |
| | | 0.01% mPT-MOF-Co | h | 0 | 0 |

TABLE 9-continued

Catalytic Hydrogenation of Olefins[a]

| Entry | Substrate | Precatalyst | Time | Yield (%) | TONs |
|---|---|---|---|---|---|
| 18 | Ph-CH=CH- | 0.1% bpy-MOF-Co | 20 h | 100 | >1000 |
| 19 |  | 0.1% bpyv-MOF-Co | 20 h | 100 | >1000 |
|  |  | 0.01% mPT-MOF-Co | h | 0 | 0 |
| 20 | Ph-CH=CH-CH3 | 0.1% bpy-MOF-Co | 20 h | 88 | 880 |
| 21 |  | 0.01% bpyv-MOF-Co | 20 h | 100 | >1000 |
| 22 | cyclohexene | 0.1% bpy-MOF-Co | 20 h | 100 | >1000 |
| 23 |  | 0.1% bpyv-MOF-Co | 20 h | 100 | >1000 |
|  |  | 0.01% mPT-MOF-Co | h | 0 | 0 |
|  | diene |  0.01% bpyv-MOF-Co 0.01% mPT-MOF-Co |  |  |  |
| 24 | allyl OAc | 0.1% bpy-MOF-Co | 70 h | 15 | 150 |
| 25 |  | 0.1% bpyv-MOF-Co | 70 h | 66 | 660 |

[a]Reaction conditions: 2-3 mg of MOF-CoCl$_2$, 8 equiv of NaBEt$_3$H (1.0 M in THF) w.r.t. Co, alkene, THF, 40 bar H$_2$, 23° C.

Figure 4A:
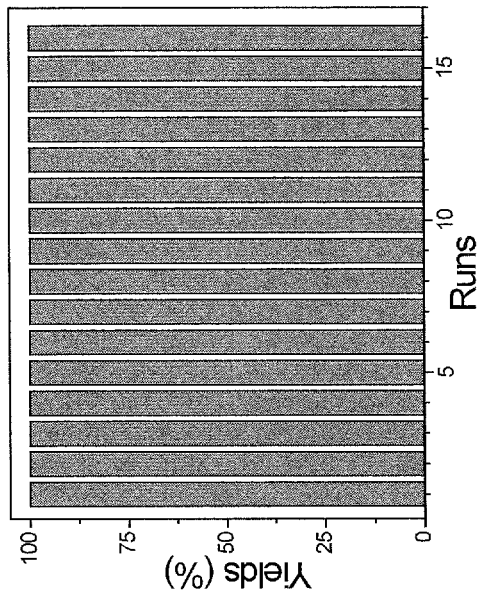
FIGS. 4A and 4B are plots of yield (%) of n-octane at different runs in the reuse experiments of bpy-MOF-Co (FIG. 4A) and bpyv-MOF-Co (FIG. 4B) for hydrogenation of 1-octene. The Co loadings were 0.5 mol %.
Figure 4B:
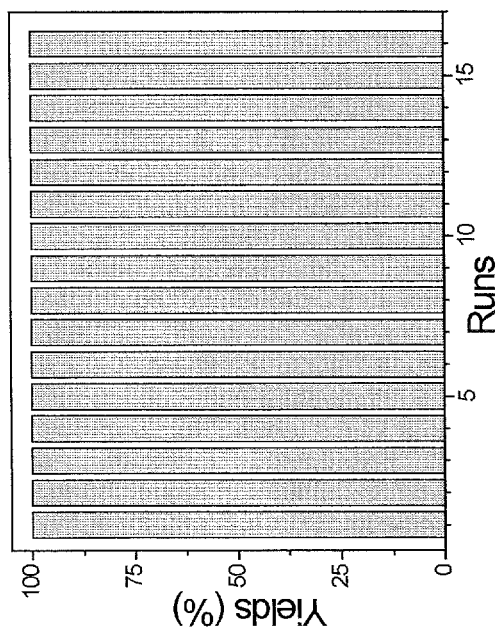

Impressively, at 0.5 mol % Co loading, both bpy-MOF-Co and bpyv-MOF-Co catalysts can be recovered and reused for at least 16 times for the hydrogenation of 1-octene without loss of catalytic activity (FIGS. 4A and 4B). Complete conversion was observed in every run without evidence of olefin isomerization or other byproducts. PXRD patterns of the MOF catalysts after catalysis were identical to those of the pristine MOF catalysts, indicating the stability of the framework under catalytic conditions. Additionally, ICP-MS analyses of the organic product showed negligible metal leaching after the 2$^{nd}$ run, with the leaching of 0.0004% Co and 0.001% Zr for bpy-MOF-Co, 0.0005% Co and 0.002% Zr for bpyv-MOF-Co, and 0.001% Co and 0.001% Zr for mPT-MOF-Co, respectively. A "cross" test further confirmed the heterogeneity of MOF-catalysts: after bpyv-MOF-Co was used to catalyze hydrogenation of styrene with complete conversion in 6 h, the MOF was separated from the supernatant and an equal molar amount of 1-octene was added to the solid and supernatant, respectively. After 18 h under hydrogen atmosphere, 1-octene was completely converted to n-octane in presence of the MOF solid but no conversion was observed in presence of the supernatant. This experiment proved that the MOF, not the leached species, was the active catalyst for hydrogenation.

To demonstrate the unique role of MOFs in stabilizing the catalytically active species, we compared the catalytic activities of the bipyridyl-MOF-Co catalysts with a molecular control, $^{Me2}$bpy-CoCl$_2$ ($^{Me2}$bpy=6,6'-dimethyl-2,2'-bipyridine) that was made from a 1:1 mixture of CoCl$_2$ and $^{Me2}$bpy in THF. Upon treatment with NaEt$_3$BH, 0.1 mol % $^{Me2}$bpy-CoCl$_2$ or CoCl$_2$ hydrogenated styrene to ethylbenzene in 100% conversion, however, no conversion was obtained with 0.01 mol % catalyst loading under identical reaction conditions (entries 1-4, Table 10). In contrast, at a 0.01 mol % Co loading, both bpy-MOF-Co and bpyv-MOF-Co afforded ethylbenzene quantitatively. Catalytic activity of the molecular control decreased dramatically in presence of mercury, indicating the contribution of catalytic activity from Co-nanoparticles formed during hydrogenation reactions. In contrast, the activities of MOFs-Co catalysts were not affected by the presence of mercury. The significantly enhanced stability and activity of MOF-Co catalysts compared to their homogeneous controls are likely due to active site isolation within MOF cavities which prevent any intermolecular deactivation pathways.

Scheme 17

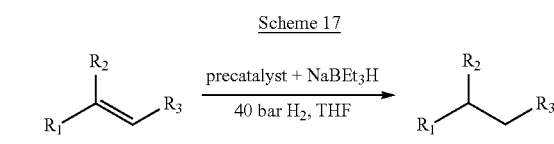

TABLE 10

Olefin hydrogenation catalyzed by MOF catalysts and homogeneous controls.[a]

| Entry | Precatalyst | Conversion (%)[b] |
|---|---|---|
| 1 | 0.1% CoCl$_2$ | 100 (78) |
| 2 | 0.1% $^{Me2}$bpy-CoCl$_2$ | 100 (28) |
| 3 | 0.01% CoCl$_2$ | 0 |
| 4 | 0.01% $^{Me2}$bpy-CoCl$_2$ | 0 |
| 5 | 0.01% bpy-MOF-Co | 100 |
| 6 | 0.01% bpyv-MOF-Co | 100 |

[a]Reaction conditions: 0.1% or 0.01% of precatalyst with 5 equiv. of NaBEt$_3$H, 40 bar H$_2$, THF, room temperature, 20 h.
[b]Conversions in parentheses are obtained in presence of metallic mercury.

To gain insight into the nature of MOF-Co catalysts and their analogous homogeneous molecular controls, effort was made on characterizing the active species generated after treating NaEt$_3$BH with cobalt precatalysts. The reaction of $^{Me2}$bpy-CoCl$_2$ with 2.0 equiv. NaEt$_3$BH in THF under dinitrogen atmosphere at room temperature provided a deep blue solution of ($^{Me2}$bpy)$_2$Co(0) (0.5 equiv), H$_2$ (1.0 equiv), and cobalt-nanoparticles (0.5 equiv) as a black precipitate within 15 minutes (Scheme 18). H$_2$ was identified and quantified by GC analysis. The composition of cobalt-nanoparticles were established by ICP-MS and TGA. ($^{Me2}$bpy)$_2$Co(0) was isolated as a paramagnetic bluish-black solid, which was structurally characterized by single crystal X-ray diffraction. Presumably, the reductive elimination of H$_2$ from the transient $^{Me2}$bpy-cobalt dihydride generates reduced $^{Me2}$bpy-Co, which undergoes intermolecular ligand-disproportionation (or unidirectional Schlenk equilibrium via intermolecular pathways) to furnish the observed products. Unfortunately, attempts to identify and isolate $^{Me2}$bpy-cobalt dihydride or $^{Me2}$bpy-Co species were unsuccessful. However, in a related reaction, the treatment of bulky aryl-substituted bis(imino) pyridine ($^{Ar}$PDI)-ligated iron dichloride or dibromide complexes with 2 equiv of NaEt$_3$BH resulted in isolation of iron(0) bis(dinitrogen) complex ($^{Ar}$PDI)Fe(N$_2$)$_2$ via reductive of H$_2$ from putative iron(II) dihydride intermediate. The steric protection around the iron center in ($^{Ar}$PDI)Fe(N$_2$)$_2$ is likely the key factor in stabilizing these iron(0) compounds from intermolecular decomposition. Similarly, the reaction of NaEt$_3$BH with MOF-CoCl$_2$ generated MOF-Co(0) with the liberation of H$_2$. The oxidation state and coordination sphere of cobalt in MOF-Co(0) were characterized by XANES and EXAFS.

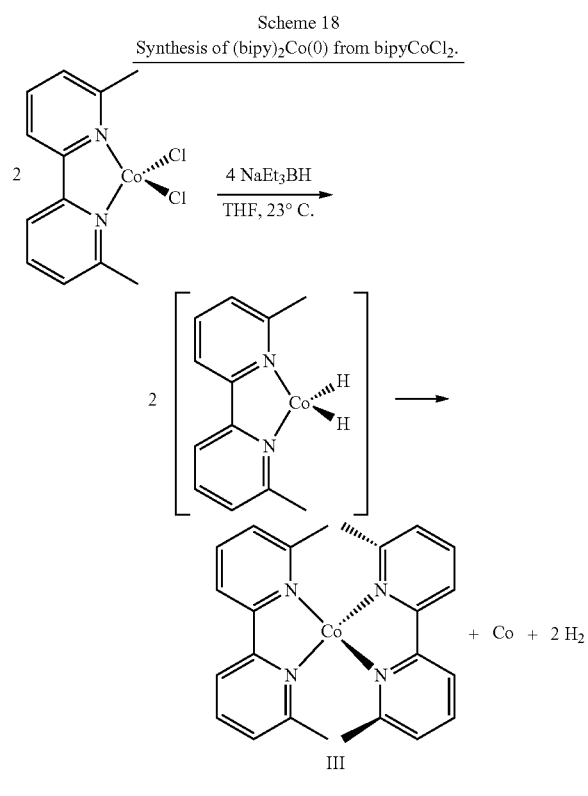

Scheme 18
Synthesis of (bipy)$_2$Co(0) from bipyCoCl$_2$.

MOF-Co catalysts are also active in hydroborylation of alkenes or dehydrogenative C—H borylation of arenes to afford alkyl or arylboronates, which are versatile reagents in organic synthesis. Alkene hydroboration reactions were performed with 0.1-0.01 mol % MOF-Co in a neat, 1:1.2 equiv mixtures of alkene and pinacolborane (HBpin) at room temperature to obtain the highest yields (Table 11). At a 0.1 mol % Co loading, bpyv-MOF-Co gave complete conversion of 1-octene within 16 h at room temperature to furnish a mixture of 66% anti-Markovnikov octylboronate ester and 34% internal alkenes. However, under identical reaction conditions, mPT-MOF-Co afforded exclusively octylboronate ester in 97% yield with TON up to 10,000 (Table 11). The hydroboration of other terminal alkenes such as 1-decene, 5-methyl-1-hexene and 6-chloro-1-hexene occurred selectively in anti-Markovnikov fashion to afford corresponding alkylboronates in excellent yields with 0.1-0.01 mol % mPT-MOF-Co. mPT-MOF-Co was also active in catalytic hydroboration of internal alkenes. Importantly, mPT-MOF-Co can be recycled at least 15 times without any noticeable diminishing activity in hydroboration of 1-octene. A negligible leaching of Co (<0.01%) and Zr (<0.005%) was observed into the supernatant after run 1. No hydroboration reaction was observed after removal of mPT-MOF-Co from the reaction mixture, which rules out any role of leached cobalt species in catalyzing hydroboration. Additionally, Co-nanoparticles or homogeneous controls, $^{Me2}$bpy-Co and PT-Co, are barely active in catalyzing hydroboration reactions (e.g., entry 1, Table 11). The higher activities of MOF-Co catalysts strongly support the beneficial effect of active site isolation in the MOF frameworks, which prevents any intermolecular deactivation.

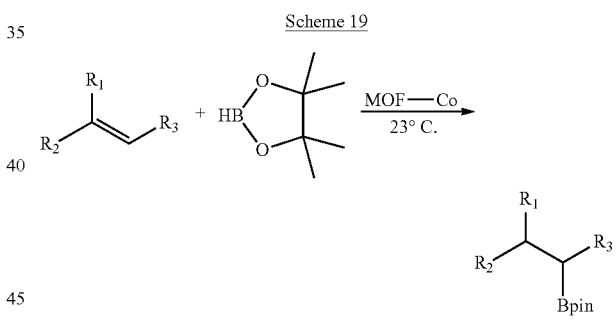

Scheme 19

TABLE 11

| | | | | | |
|---|---|---|---|---|---|
| Entry | Substrate | Product | Co-catalysts (mol % loading) | Time | % Yield (TONs) |
| | 1-octene | ⌇⌇⌇$_4$Bpin | bpyv-MOF-Co (0.1) mPT-MOF-Co (0.1) mPT-MOF-Co (0.01) CoCl$_2$ (0.1) Co($^{Me2}$bpy)Cl$_2$ (0.1) | 16 h 16 h 3 h 20 h 20 h | 66 (660) 100 (>1000) 100 (10000) 0 37 |
| | 1-decene | ⌇⌇⌇$_6$Bpin | mPT-MOF-Co (0.1) | 16 h | 100 (>1000) |
| | | ⌇⌇⌇$_2$Bpin | mPT-MOF-Co (0.1) mPT-MOF-Co (0.01) | 16 h 4 d | 100 (>1000) 100 (10000) |

TABLE 11-continued

MOF-Co-Catalyzed Hydroboration of Alkenes[a]

| Entry | Substrate | Product | Co-catalysts (mol % loading) | Time | % Yield (TONs) |
|---|---|---|---|---|---|
| | Cl~~~~= | Cl~(~)₃~Bpin | mPT-MOF-Co (0.1) | 2 d | 86 |
| | (2-methyl-2-butene) | (Bpin product) | mPT-MOF-Co (0.1) | 18 h | 100 (>1000) |
| | Ph\\=/Me (α-methylstyrene) | Ph\\~Bpin / Me | mPT-MOF-Co (0.1) | | |

[a]Reaction conditions: 0.1-0.01 mol % MOF-CoCl₂, 10 equiv NaBEt₃H (1.0 M in THF), alkene, pinacolborane (1.2 equiv w.r.t. alkene), 23° C.

Figure 5:
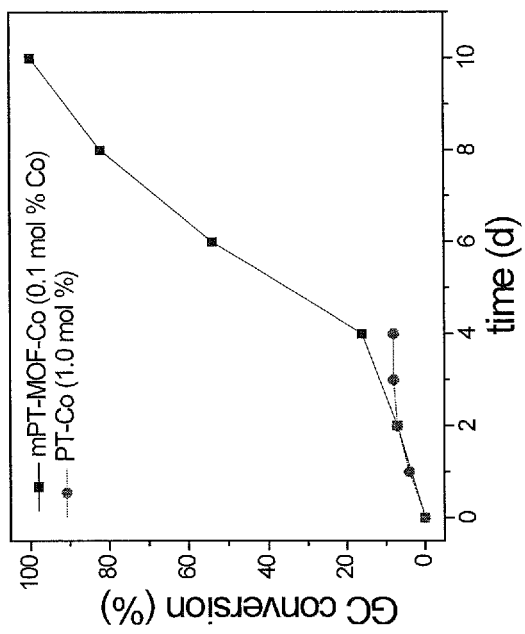
FIG. 5 shows plots of GC conversion (%) vs time (days, d) for C—H borylation of m-xylene using mPT-MOF-Co (0.1 mol %) and PT-Co (1.0 mol %) as catalysts at 100° C. under N$_2$.

Inspired by the high activity of mPT-MOF-Co in alkene hydroboration, the catalytic activity of MOF-Co catalysts in dehydrogenative borylation of aromatic C—H bonds were investigated. In homogeneous catalysis, although a number of nitrogen and phosphine-based iridium(I) catalysts have been reported, the bipyridyl- or phenanthryl-derived iridium catalysts are the most active and widely used in C—H borylation. Efforts in developing heterogeneous borylation catalysts has been made based on precious metals such as iridium(0) nanoparticles, insoluble iridium complex, or silica-supported rhodium and iridium catalysts. Recently, bis(imino)pyridine- and bis(phosphino)pyridine-supported cobalt catalysts have been reported for arene C—H borylation. mPT-MOF-Co was initially employed in C—H borylation reactions for optimized conditions such as temperature, activating and borylating reagents, solvents, and in neat arenes (without using a solvent) to obtain the best results. The screening experiments revealed that the highest yields were obtained when the borylation reactions were performed in neat arene at 100° C. or refluxed in n-heptane at 100° C. for solid substrates. mPT-MOF-Co catalyzed borylation of o- and m-xylene occurred selectively at the least sterically hindered C—H bonds. 1,2-Dimethyl-4-(4,4,5,5-tetramethyl-1,3,2-dioxaborolan-2-yl)benzene and 5-(4,4,5,5-tetramethyl-1,3,2-dioxaborolan-2-yl)-m-xylene were obtained from o- and m-xylene in 90 and 92% yield, respectively, with 0.1 mol % mPT-MOF-Co (e.g., entries 1 and 2, Table 12). Although only phenylboronate was afforded from benzene as a monoborylated product, the borylation of toluene furnished a mixture of meta- and para-substituted products in a 60:40 ratio. Interestingly, both mPT-MOF-Co is significantly more active in C—H borylation of arenes than their homogeneous control PT-Co. 1.0 mol % of PT-Co afforded 5-(4,4,5,5-tetramethyl-1,3,2-dioxaborolan-2-yl)-m-xylene from m-xylene in only 8% conversion in four days, after which no further conversion was observed with further heating. In contrast, the conversion of m-xylene proceeded with time until completion in the presence of 0.1 mol % mPT-MOF-Co (FIG. 5). This result indicates that mPT-MOF-Ir is at least 125 times more active than the homogeneous control for the C—H borylation reaction.

Scheme 20

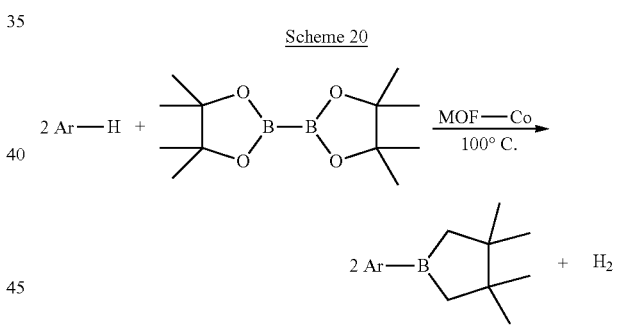

TABLE 12

MOF-Co-Catalyzed C—H Borylation of Arenes[a]

| Entry | Substrate | Product | MOF-Co (mol % loading) | Time | % Yield |
|---|---|---|---|---|---|
| 1 | m-xylene | Bpin-m-xylene | bpyv-MOF-Co (0.1) mBPP-MOF-Co (0.5) mPT-MOF-Co (0.1) | 4 d 10 d | 50 100 (92) |

TABLE 12-continued

MOF-Co-Catalyzed C—H Borylation of Arenes[a]

| Entry | Substrate | Product | MOF-Co (mol % loading) | Time | % Yield |
|---|---|---|---|---|---|
| 2 | o-xylene | 4-Bpin-o-xylene | mPT-MOF-Co (0.1) | d | 100 |
| 3 | benzene | PhBpin | bpyv-MOF-Co (1.0)<br>mPT-MOF-Co (0.1)<br>mPT-MOF-Co (0.05) | 11 d<br>12 d | 85<br>51 |
| 4 | toluene | Bpin-toluene | mPT-MOF-Co (0.1) | 6 d | 90 (o:m:p = 0:60:40) |
| 5 | indole | 2-Bpin-indole | mPT-MOF-Co (0.25)<br>mPT-MOF-Co (0.1) | 3 d<br>4.5 | 100<br>76 |

[a]Reaction conditions: 0.25-0.05 mol % MOF-CoCl$_2$, 10 equiv NaBEt$_3$H (1.0 M in THF), arene, B$_2$pin$_2$, 100° C., reflux under N$_2$.

The catalytic activity of MOFs-Co was also evaluated for hydroboration of ketones and aldehydes (Lindsley, C. W.; DiMare, M. *Tetrahedron Letters* 1994, 35, 5141; Blake, A. J.; Cunningham, A.; Ford, A.; Teat, S. J.; Woodward, S. *Chemistry—A European Journal* 2000, 6, 3586; Koren-Selfridge, L.; Londino, H. N.; Vellucci, J. K.; Simmons, B. J.; Casey, C. P.; Clark, T. B. *Organometallics* 2009, 28, 2085; Arrowsmith, M.; Hadlington, T. J.; Hill, M. S.; Kociok-Kohn, G. *Chem Commun* 2012, 48, 4567; Almqvist, F.; Torstensson, L.; Gudmundsson, A.; Frejd, T. *Angewandte Chemie International Edition in English* 1997, 36, 376; Ford, A.; Woodward, S. *Angewandte Chemie International Edition* 1999, 38, 335; Sarvary, I.; Almqvist, F.; Frejd, T. *Chemistry—A European Journal* 2001, 7, 2158; Locatelli, M.; Cozzi, P. G. *Angewandte Chemie International Edition* 2003, 42, 4928; Khalimon, A. Y.; Farha, P.; Kuzmina, L. G.; Nikonov, G. I. *Chem Commun* 2012, 48, 455; Oluyadi, A. A.; Ma, S.; Muhoro, C. N. *Organometallics* 2012, 32, 70; Hadlington, T. J.; Hermann, M.; Frenking, G.; Jones, C. *J. Am. Chem. Soc.* 2014, 136, 3028; Mukherjee, D.; Ellern, A.; Sadow, A. D. *Chemical Science* 2014, 5, 959). The hydroboration of carbonyl compounds was performed by treating ketones or aldehydes with equimolar HBpin in presence of 0.05-0.01 mol % MOF-Co at r.t. (Table 5). 0.05 mol % bpyv-MOF-Co afforded borate ester products from a range of carbonyl substrates, including alkyl, halogenated, and alkoxy-functionalized aryl ketones and aldehydes in essentially quantitative yields. A TON of >20,000 was obtained for hydroboration of 4-methoxyacetophenone (e.g., entry 3, Table 5). Borate ester was also obtained from heterocyclic carbonyl compounds such as 2-acetylthiophene in excellent yields (e.g, entry 7, Table 13). Notably, pure products were obtained by simply removing the catalyst via centrifugation followed by removal of the organic volatiles. ICP-MS analyses showed that the amounts of Co and Zr leaching into the supernatant after hydroboration of 4-methoxyacetophenone were 1.93% and 0.82%, respectively. Interestingly, bpyv-MOF-Co is significantly more active in hydroboration than its homogeneous counterpart. 0.05 mol % of (bpy)CoCl$_2$ afforded borate ester from 2-acetylthiophene in 62% conversion and no further conversion was observed with a prologed reaction time. This result indicates that bpyv-MOF-Co is at least three times more active than its homogeneous control.

Scheme 21

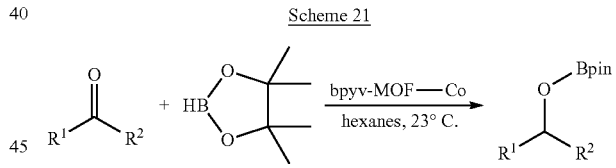

TABLE 13 bpyv-MOF-Co catalyzed hydroboration of ketones and aldehydes.[a]

| Entry | Substrate | mol % Co | Time | % Conversion[b] |
|---|---|---|---|---|
| 1 | acetophenone | 0.05 | 1 d | 100 (98) |
| 2 | 4-methoxyacetophenone | 0.05 | 24 h | 100 |
| 3 | 4-methoxyacetophenone | 0.005 | 3 d | 100 |

TABLE 13-continued bpyv-MOF-Co catalyzed hydroboration of ketones and aldehydes.[a]

| Entry | Substrate | mol % Co | Time | % Conversion[b] |
|---|---|---|---|---|
| 4 | benzophenone | 0.01 | 1 d | 100 (96) |
| 5 | 4-chlorobenzaldehyde | 0.05 | 40 h | 100 |
| 6 | 4-chlorobenzaldehyde | 0.01 | 3 d | 84 |
| 7 | 2-acetylthiophene | 0.05 | 1 d | 100 (96) |
| 8 | 2-acetylthiophene | 0.01 | 3 d | 41 |

[a]Reaction conditions: bpyv-MOF-CoCl₂, 10 equiv. of NaBEt₃H, carbonyl substrate, hexanes, 23° C. [b]Isolated yield in the parenthesis.

In summary, this Example discloses a highly active, robust, and recyclable single-site base-metal catalysts for a broad scope of organic transformations by simple post-synthetic metalation of bipyridyl- and phenanthryl-based MOFs. While it is not desired to be bound by any particular theory of operation, site isolation of the active bpy- and phen-Co species within MOF cavities is likely key to their enhanced activities and stabilities. In addition, we believe that MOF catalysts constructed with longer functionalized linkers or with doping of functionalized and unfunctionalized linkers have much larger open channels, which facilitates the transport of the substrates and products through the MOF channels. Therefore, MOFs provide a unique platform of new base metal catalysts for sustainable chemical synthesis.

1. General Experimental for Example 9

All of the solvents were purchased from Fisher and used without further purification unless otherwise noticed. All of the other substrates and reagents are commercially available and used as received unless otherwise indicated. 1-octene, styrene, α-methylstyrene, cis-β-methylstyrene, trans-β-methylstyrene, allyl acetate, and benzaldehyde were distilled and then dried over freshly activated 4 Å molecular sieves prior to use. Cyclohexene, acetophenone, cyclohexanone, 2-acetylthiophene, 1-decene, 5-methyl-1-hexene, 3-methyl-2-butene, and 6-chloro-1-hexene were dried with freshly activated 4 Å molecular sieves in a glovebox prior to use. Pinacolborane was purchased from Fisher and was freshly distilled prior to use. $^1$H NMR spectra were recorded on a Bruker NMR 400 DRX spectrometer at 500 MHz and referenced to the proton resonance resulting from incomplete deuteration of the deuterated chloroform (δ 7.26) or deuterated DMSO (δ 2.50). Thermogravimetric analysis (TGA) was performed in air using a Shimadzu TGA-50 equipped with a platinum pan. Powder X-ray diffraction (PXRD) patterns were collected on a Bruker D8 Venture, dual microsource (Cu and Mo) diffractometer with a CMOS detector. Cu Kα radiation was used. The PXRD patterns were processed with the APEX 2 package using PILOT plug-in. Background diffraction signal from glass capillary tube and solvent at 2θ~20° was simulated and removed by the program PowderX. ICP-MS data were obtained with an Agilent 7700x ICP-MS and analyzed using ICP-MS Mass-Hunter version B01.03. Samples were diluted in a 2% HNO₃ matrix and analyzed with a $^{159}$Tb internal standard against a six-point standard curve over the range from 0.1 ppb to 1000 ppb. The correlation coefficient was >0.9997 for all analytes of interest. Data collection was performed in Spectrum Mode with five replicates per sample and 100 sweeps per replicate.

2. Synthesis and Characterization of Ligands, MOFs, and Metalated MOFs 2.1. 5,5'-bis(methoxycarbonylethenyl)-2,2%bipyridine 5,5'-dibromo-2,2'-bipyridine (646 mg, 2.0 mmol) was dissolved in a mixture of 10 mL of DMF and 10 mL of triethylamine and degassed with nitrogen. Palladium acetate (19 mg), tris(o-tolyl)phosphine (84 mg), and methyl acrylate (2.5 mL, 27.6 mmol) were then added to the solution. The reaction vessel was sealed in a pressure vessel under nitrogen and heated at 120° C. for 2 days. After cooling to r.t., the solution was concentrated to afford a yellow solid as the crude product, which was purified through Soxhlet extraction with chloroform to afford the pure 5,5'-bis(methoxycarbonylethenyl)-2,2'-bipyridine as a light yellow solid (428 mg, 66%). $^1$H NMR (500 MHz, CDCl₃) δ 8.83 (s, 2H), 8.51 (d, 2H, $^3J_{HH}$=8.2 Hz), 8.01 (dd, 2H, $^3J_{HH}$=8.2 Hz, $^4J_{HH}$=2.0 Hz), 7.77 (d, 2H, $^3J_{HH}$=16.0 Hz), 6.61 (d, 2H, $^3J_{HH}$=16.0 Hz), 3.87 (s, 6H).

2.2. 3,3'-(2,2'-bipyridyl-5,5'-diyl)diacrylic acid (H₂BPYV)

5,5'-bis(methoxycarbonylethenyl)-2,2'-bipyridine (428 mg, 1.3 mmol) was dissolved in a mixture of equal volume of 6 M NaOH (aq) and ethanol and refluxed overnight. After cooling to r.t., the solution was acidified with 2 M HCl and centrifuged. The solid was washed sequentially with water, ethanol, and ether, then dried under vacuum to afford 3,3'-(2,2'-bipyridyl-5,5'-diyl)diacrylic acid as a white solid (350 mg, 91%). $^1$H NMR (500 MHz, DMSO-d₆) δ 12.64 (br s, 2H), 9.00 (s, 2H), 8.44 (d, 2H, $^3J_{HH}$=8.5 Hz), 8.33 (dd, 2H, $^3J_{HH}$=8.5 Hz, $^4J_{HH}$=2.0 Hz), 7.71 (d, 2H, $^3J_{HH}$=16.0 Hz), 6.78 (d, 2H, $^3J_{HH}$=16.0 Hz). ESI-MS: m/z [M+H]⁺=297.1 (calcd. 297.09).

2.3. bpy-MOF

ZrCl₄ (30 mg, 0.13 mmol), 2,2'-bipyridine-5,5'-dicarboxylic acid (H₂BPY, 30 mg, 0.12 mmol), DMF (15 mL) and trifluoroacetic acid (0.06 mL) were charged in a vial and heated to 100° C. for 5 days. The resulting white solid was collected and washed with DMF to give the MOF product (yield: 40 mg, 65%).

2.4. bpyv-MOF

ZrCl₄ (10 mg, 0.043 mmol), H₂BPYV (10 mg, 0.034 mmol), DMF (5 mL) and trifluoroacetic acid (0.08 mL) were charged in a vial and heated to 100° C. for 5 days. The resulting white to pale yellow solid was collected and washed with DMF to give the MOF product (yield: 20 mg, 65%).

2.5. mBPP-MOF

ZrCl₄ (10 mg), H₂BPP (6 mg) and 4,4'-bis(carboxyphenyl)-2-nitro-1,1'-biphenyl (14 mg) were dissolved in 5 mL of DMF and 0.05 mL of trifluoroacetic acid was added. The solution was then heated to 100° C. for 5 days to afford a pale yellow solid as the MOF product (yield 17 mg, 45%).

Analysis of Digested mBPP-MOF by $^1$H NMR.

To determine the ratio of the two ligands, 10 mg of mBPP-MOF was first washed with THF and dried under vacuum. The resulting solid was then digested in a 1:1 mixture of saturated $K_3PO_4/D_2O$ solution and DMSO-$d_6$ and shaken for 5 minutes. The organic layer was then analyzed by $^1$H NMR and the ligand ratio was determined by comparing the peaks corresponding to each ligand.

2.6. mPT-MOF $ZrCl_4$ (10 mg), $H_2PT$ (6 mg) and 4,4'-bis(carboxyphenyl)-2-nitro-1,1'-biphenyl (14 mg) were dissolved in 5 mL of DMF and 0.05 mL of trifluoroacetic acid was added. The solution was then heated to 100° C. for 5 days to afford a pale yellow solid as the MOF product (yield 17 mg, 45%).

2.7. bpy-MOF-CoCl$_2$

In a glovebox, $CoCl_2$ (13.0 mg, 0.10 mmol) was dissolved in 10 mL of THF. bpy-MOF (10.0 mg) was weighted onto filter paper, washed with THF for several times and added to the metal salt solution. The resulting suspension was stirred at room temperature slowly overnight and the blue-green solid was then centrifuged out and washed with THF for 4-5 times. The metalated MOFs were then stored in THF in the glovebox for further uses.

BET surface areas for bpy-MOF-FeCl$_2$ and bpy-MOF-CoCl$_2$ are 758 m$^2$/g and 764 m$^2$/g, respectively. BET surface area of bpy-MOF is 2277 m$^2$/g.

2.8. bpyv-MOF-CoCl$_2$

In a glovebox, $CoCl_2$ (13.0 mg, 0.10 mmol) was dissolved in 10 mL of THF. bpyv-MOF (18.0 mg) was weighted onto filter paper, washed with THF for several times and added to the metal salt solution. The resulting suspension was stirred at room temperature slowly overnight and then blue-green solid was then centrifuged out and washed with THF for 4-5 times. The metalated MOFs were then stored in THF for further uses. Bpyv-MOF-CoCl$_2$ has 54% solvent weight based on TGA analysis and 92% Ir-loading with respect to Zr centers (i.e. total bridging ligands) based on ICP-MS analysis. TGA curves of freshly prepared bpyv-MOF and bpyv-MOF-CoCl$_2$ in the 25-600° C. range and 200-600° C. range were prepared. The increased residual mass at 600° C. is due to the presence of Co in bpyv-MOF-CoCl$_2$.

BET surface areas for bpyv-MOF-FeCl$_2$ and bpyv-MOF-CoCl$_2$ are 371 m$^2$/g and 294 m$^2$/g, respectively. BET surface area of bpyv-MOF is 373 m$^2$/g. HK pore size distribution of bpyv-MOF-CoCl$_2$ was also evaluated.

2.9. mBPP-MOF-CoCl$_2$

In a glovebox, $CoCl_2$ (13.0 mg, 0.10 mmol) was dissolved in 10 mL of THF in a vial. mBPP-MOF (40.0 mg) in THF was added to the metal salt solution. The resulting suspension was stirred at room temperature slowly overnight. The resultant blue-green solid was then centrifuged out and washed with THF for 4-5 times. The metalated MOFs were then stored in heptane for further uses. mBPP-MOF-CoCl$_2$ has 31% solvent weight based on TGA analysis and 21% Ir-loading with respect to Zr centers (i.e. total bridging ligands) based on ICP-MS analysis. TGA curves of freshly prepared mBPP-MOF and mBPP-MOF-CoCl$_2$ in the 25-600° C. range and 200-600° C. range were prepared. An increased residual mass at 600° C. was due to the presence of Co in mBPP-MOF-CoCl$_2$.

2.10. mPT-MOF-CoCl$_2$

In a glovebox, $CoCl_2$ (8.0 mg, 0.06 mmol) was dissolved in 10 mL of THF. mPT-MOF (30.0 mg) was weighted onto filter paper, washed with THF for several times and added to the metal salt solution. The resulting suspension was stirred at room temperature slowly overnight. The resultant blue-green solid was then centrifuged out and washed with THF for 4-5 times. The metalated MOFs were then stored in heptane for further uses. mPT-MOF-Ir has 60% solvent weight based on TGA analysis and 12% Ir-loading with respect to Zr centers (i.e. total bridging ligands) based on ICP-MS analysis. TGA curves of freshly prepared mPT-MOF and mPT-MOF-CoCl$_2$ in the 25-600° C. range and 200-600° C. range were prepared. An increased residual mass at 600° C. is due to the presence of Co in mPT-MOF-CoCl$_2$.

3. Crystallographic Information and Structural Figures

Single crystal X-ray diffraction of bpyv-MOF was collected with a Bruker APEX II CCD-based detector at ChemMatCARS (Sector 15), Advanced Photon Source (APS), Argonne National Laboratory. The frames were integrated with the Bruker SAINT© build in APEX II software package using a narrow-frame integration algorithm, which also corrects for the Lorentz and polarization effects. Absorption corrections were applied using SADABS. Structures were solved by direct methods and refined to convergence by least squares method on F$^2$ using the SHELXTL-2013 software suite (G. Sheldrick, *Acta Crystallographica Section A* 2008, 64, 112-122).

Due to the relatively weak diffraction and low resolution, which is not uncommon for this kind of framework with very large solvent accessible void space, restraints (SIMU and DELU) on displacement parameters, and DFIX for bond lengths are applied. The pyridine ring is constrained to ideal geometry. Non-hydrogen atoms are refined isotropically. SQUEEZE subroutine of the PLATON software suite was applied to remove the scattering from the highly disordered guest molecules. The resulting new HKL4 files were used to further refine the structure.

TABLE 14

Crystallographic information.

| | Name | |
|---|---|---|
| | bpyv-MOF | 3Co(Me$_2$bpy)$_2$•THF |
| Formula | Zr$_6$O$_4$(OH)$_4$(C$_{16}$H$_{12}$N$_2$O$_4$)$_6$ | CoC12H24N2O |
| Fw | 2412.91 | 271.26 |
| Temperature (K) | 100 | 100 |
| Wavelength (Å) | 0.51800 | 0.71073 |

TABLE 14-continued

Crystallographic information.

| Name | bpyv-MOF | 3Co(Me$_2$bpy)$_2$•THF |
|---|---|---|
| Crystal system | Cubic | monoclinic |
| Space group | Fm$\bar{3}$m | C2/c |
| a, Å | 32.499 (7) | 25.4633 (16) |
| b, Å | 32.499 (7) | 12.1607 (8) |
| c, Å | 32.499 (7) | 22.1318 (14) |
| α, ° | 90 | 90 |
| β, ° | 90 | 107.914 (2) |
| γ, ° | 90 | 90 |
| V, Å$^3$ | 34326 (22) | 6520.9 (7) |
| Z | 4 | 24 |
| Density (calcd. g/cm$^3$) | 0.467 | 1.658 |
| Absorption coeff. (mm$^{-1}$) | 0.496 | 1.559 |
| F(000) | 4816 | 3480 |
| θ range data collection | 0.791-11.520 | 2.137-30.590 |
| Limiting indices | −25 <= h <= 25 | −36 <= h <= 32 |
|  | −24 <= k <= 25 | −17 <= k <= 17 |
|  | −23 <= l <= 25 | −31 <= l <= 31 |
| Reflection collected | 31759 | 54875 |
| Independent reflections | 473 | 9988 |
| R(int) | 0.0966 | 0.0895 |
| Data/restraints/parameters | 473/23/31 | 9988/0/411 |
| Goodness-of-fit on F$^2$ | 2.369 | 1.196 |
| Final R indices [I > 2σ(I)] | R1 = 0.1177, wR2 = 0.2742 | R1 = 0.0654, wR2 = 0.1723 |
| R indices (all data) | R1 = 0.1246, wR2 = 0.2770 | R1 = 0.1003, wR2 = 0.1895 |

4. Spectroscopic Characterization of MOF-Co(0) Species

4.1 Synthesis and Characterization of Homogeneous Molecular Controls

Synthesis of Co(Me$_2$bipy)Cl$_2$ was reported in previous literature (N. Akbarzadeh Torbati, A. R. Rezvani, N. Safari, H. Saravani, V. Amani, *Acta Crystallographica Section E* 2010, 66, m1284).

Synthesis of Co(Me$_2$bipy)$_2$.

Co(Me$_2$bipy)Cl$_2$ (20.0 mg, 0.063 mmol) was suspended in 6 mL of THF in a nitrogen filled glove box. To the suspension 0.15 mL of NaBEt$_3$H solution in THF (1.0 M) (2.5 equiv.) was added and the resulting mixture was stirred for another 15 min. The solution turned deep blue immediately and black precipitate was observed. The solution was then filtered, concentrated and the resulting solid was recrystallized in THF/diethyl ether at −30° C. to afford the desired product as dark crystal.

4.2 Characterization of MOF-Co(0) Species

Trapping the Co(0) Species with 2,2'-Bipyridine.

In a nitrogen-filled glove box, bpyv-MOF-Co (2.0 mg) in 1.0 mL benzene was charged into a glass vial. NaBEt$_3$H (15 μL, 1.0 M in THF) was then added to the vial and the mixture was stirred for 15 min. 2,2'-bipyridine (2 equiv. w.r.t. Co) was then added, the mixture stirred for another 30 min and washed with benzene for 3-4 times. The MOF was then quickly dried and digested with K$_3$PO$_4$/D$_2$O/DMSO and analyzed by $^1$H NMR. Comparing the peaks corresponding to H$_2$bpyv and 2,2'-bipyridyl gives 1:1 molar ratio of the two compounds in the digested sample. Control experiments using bpyv-MOF showed no 2,2'-bipyridyl peaks, excluding the possibility of simply adsorbing or trapping 2,2'-bipyridyl in the MOF channels without coordination bonding.

5. X-Ray Absorption Spectroscopic Analysis

5.1 Data Collection

X-ray absorption data were collected at Beamline 9-BM-C at the Advanced Photon Source (APS) at Argonne National Laboratory. Spectra were collected at the iron or cobalt K-edge in transmission mode. The X-ray beam was monochromatized by a Si(111) monochromater and detuned by 25% to minimize harmonics. A metallic iron or cobalt foil standard was used as the reference for energy calibration and was measured simultaneously with experimental samples. The incident beam intensity (I$_0$) was measured by an ionization chamber with 30% N$_2$ and 70% He gas composition. Data was collected in three regions: a pre-edge region −150 to −20 eV (5 eV step size, dwell time 1.0 s), XANES region −20 to 50 eV (0.5 eV step size, dwell time 1.0 s), and EXAFS region 3.62 Å$^{-1}$ to 13.93 Å$^{-1}$ (0.05 Å$^{-1}$ step size, dwell time increased linearly from 1.0 to 3.9 seconds over the region to facilitate higher k-weighted data processing). All energies are listed relative to the elemental Fe K-edge (7112 eV) or Co K-edge (7709 eV). Multiple X-ray absorption spectra were collected at room temperature for each sample. Samples were grinded and mixed with polyethyleneglycol (PEG) and packed in a 6-shooter sample holder to achieve adequate absorption length.

5.2 Data Processing

Data were processed using the Athena and Artemis programs of the IFEFFIT package based on FEFF 6 (B. Ravel, M. Newville, *Journal of Synchrotron Radiation* 2005, 12, 537-541; J. J. Rehr, R. C. Albers, *Reviews of Modern Physics* 2000, 72, 621-654). Prior to merging, spectra were calibrated against the reference spectra (metallic Fe or Co) and aligned to the first peak in the smoothed first derivative of the absorption spectrum, background removed, and spectra processed to obtain a normalized unit edge step.

5.3 EXAFS Fitting

Fits of the EXAFS region were performed using the Artemis program of the IFEFFIT package. Fits were performed with a k-weight of 3 in R-space. Refinement was performed by optimizing an amplitude factor S$_0^2$ and energy shift ΔE$_0$ which are common to all paths, in addition to parameters for bond length (ΔR) and Debye-Waller factor (σ$^2$). The crystal structures for Co(Me$_2$bpy)Cl$_2$ and Fe(Me$_2$bpy)Cl$_2$ were used to fit the EXAFS data for the molecular compounds as well as the MOFs, assuming a similar local coordination environment around the metal centers in the complex and MOFs. Unique parameters for ΔR and σ$^2$ were provided for all scattering paths in all fits. The amplitude factors S$_0^2$ for bpy-MOF-MCl$_2$ and bpyv-MOF-MCl$_2$ were set equal to that obtained from the fits of the corresponding molecular compounds.

TABLE 15

Summary of EXAFS fitting parameters for Co(Me₂bpy)Cl₂, bpy-MOF-CoCl₂, and bpyv-MOF-CoCl₂.

| | Sample | | |
|---|---|---|---|
| | Co(Me$_2$bpy)Cl$_2$ | bpy-MOF-CoCl$_2$ | bpyv-MOF-CoCl$_2$ |
| Fitting range | k 3.00-13.62 Å$^{-1}$ | k 3.00-11.98 Å$^{-1}$ | k 3.00-11.84 Å$^{-1}$ |
| | R 1-4.5 Å | R 1-4.5 Å | R 1-4.5 Å |
| Independent points | 23 | 19 | 19 |
| Variables | 12 | 11 | 11 |
| R-factor | 0.011 | 0.012 | 0.013 |
| S$_0^2$ | 1.092 ± 0.097 | 1.092 (fixed) | 1.092 (fixed) |
| ΔE$_0$(eV) | 3.93 ± 1.76 | −0.33 ± 2.29 | −1.11 ± 2.56 |
| R (Co—N) (Å) | 2.05 ± 0.02 | 2.06 ± 0.04 | 2.03 ± 0.04 |
| σ$^2$ (Co—N) (Å$^2$) | 0.0070 ± 0.0026 | 0.0120 ± 0.0026 | 0.0114 ± 0.0022 |
| R (Co—Cl) (Å) | 2.23 ± 0.01 | 2.29 ± 0.01 | 2.29 ± 0.02 |
| σ$^2$ (Co—Cl) (Å$^2$) | 0.0046 ± 0.0007 | 0.0073 ± 0.0008 | 0.0077 ± 0.0008 |
| R (Co—C2) (Å) | 2.94 ± 0.04 | 2.73 ± 0.03 | 2.73 ± 0.06 |
| σ$^2$ (Co-C2) (Å$^2$) | 0.0089 ± 0.0056 | 0.0044 ± 0.0019 | 0.0079 ± 0.0035 |
| R (Co—C6) (Å) | 3.17 ± 0.10 | 2.96 ± 0.03 | 2.96 ± 0.05 |
| σ$^2$ (Co—C6) (Å$^2$) | 0.0165 ± 0.0167 | 0.0056 ± 0.0034 | 0.0078 ± 0.0050 |
| R (Co—C2—C3) (Å) | 4.31 ± 0.04 | 4.34 ± 0.05 | 4.33 ± 0.05 |
| σ$^2$ (Co—C2—C3) (Å$^2$) | 0.0079 ± 0.0048 | 0.0103 ± 0.0056 | 0.0103 ± 0.0055 |

TABLE 16

Summary of EXAFS fitting parameters for activated bpyv-MOF-Co.

| | | | |
|---|---|---|---|
| Fitting range | k 3.00-11.80 Å$^{-1}$ | R (Co—C2) (Å) | 2.57 ± 0.02 |
| | R 1-4.5 Å | σ$^2$ (Co—C2) (Å$^2$) | 0.0022 ± 0.0018 |
| Independent points | 19 | R (Co—C6) (Å) | 3.03 ± 0.02 |
| Variables | 13 | σ$^2$ (Co—C6) (Å$^2$) | 0.0077 ± 0.0028 |
| R-factor | 0.002 | R (Co—C2—C3) (Å) | 4.21 ± 0.02 |
| S$_0^2$ | 1.051 ± 0.026 | σ$^2$ (Co—C2—C3) (Å$^2$) | 0.0104 ± 0.0024 |
| ΔE$_0$(eV) | 3.55 ± 1.13 | R (Co—Co) (Å) | 2.43 ± 0.01 |
| R (Co—N) (Å) | 1.94 ± 0.01 | σ$^2$ (Co—Co) (Å$^2$) | 0.0068 ± 0.0013 |
| σ$^2$ (Co—N) (Å$^2$) | 0.0092 ± 0.0006 | C.N. (Co) | 1.39 ± 0.26 |

TABLE 17

Summary of EXAFS fitting parameters for Co(Me₂bpy)₂.

| | | | |
|---|---|---|---|
| Fitting range | k 3.00-11.92 Å$^{-1}$ | R (Co—C2) (Å) | 2.85 ± 0.02 |
| | R 1.3-5 Å | σ$^2$ (Co—C2) (Å$^2$) | 0.0012 ± 0.0018 |
| Independent points | 20 | R (Co—C6) (Å) | 3.06 ± 0.04 |
| Variables | 12 | σ$^2$ (Co—C6) (Å$^2$) | 0.0018 ± 0.0025 |
| R-factor | 0.031 | R (Co—C7) (Å) | 3.27 ± 0.03 |
| S$_0^2$ | 0.817 ± 0.158 | σ$^2$ (Co—C7) (Å$^2$) | 0.0005 ± 0.0020 |
| ΔE$_0$(eV) | 5.54 ± 2.60 | R (Co—C2—C3) (Å) | 4.27 ± 0.06 |
| R (Co—N) (Å) | 1.96 ± 0.01 | σ$^2$ (Co—C2—C3) (Å$^2$) | 0.0080 ± 0.0061 |
| σ$^2$ (Co—N) (Å$^2$) | 0.0031 ± 0.0014 | | |

All quantum chemical calculations were performed using the density functional theory (DFT) functional B3LYP/6-311G+g(d, p) as implemented in the Gaussian 09 software suite. Electronic structure complexes were optimized at the unrestricted level.

6. Procedures for Catalytic Hydrogenation of Olefins

6.1. General Procedure for MOF-Co Catalyzed Hydrogenation of Olefins

In a nitrogen-filled glove box, MOF-Co (2.0 mg, 0.1 mol % Co) in 1.0 mL THF was charged into a glass vial. NaBEt$_3$H (15 μL, 1.0 M in THF) was then added to the vial and the mixture was stirred for 1 hour. The solid was then centrifuged, washed with THF twice, and transferred to a glass vial in 0.5 mL THF. The olefin substrate (2.0 mmol) was added to the vial. Then the vial was placed in a Parr reactor which was sealed under nitrogen atmosphere and charged with hydrogen to 40 bar. After stirring at room temperature for 18 h, the pressure was released and the MOF catalyst was removed from the reaction mixture via centrifugation. Mesitylene (internal standard) was added to the organic extracts and the yield of the product was determined by integrations of the product and mesitylene peaks in the $^1$H NMR spectra.

6.2. Reuse and Recycle Experiment Procedure for Bpyv-MOF-Co-Catalyzed Hydrogenation of 1-Octene Scheme 22

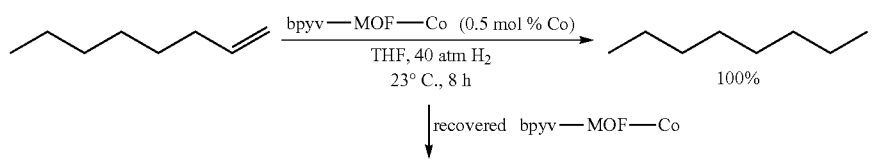

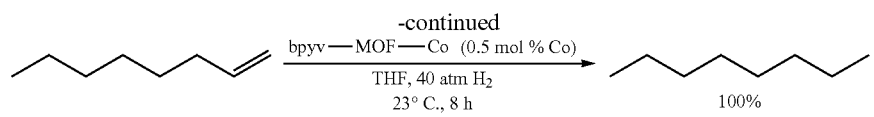

In a nitrogen-filled glove box, bpyv-MOF-CoCl$_2$ (5.0 mg, 0.5 mol % Co) in 1.0 mL THF was charged into a glass vial with a Teflon-liner cap. NaBEt$_3$H (30 µL, 1.0 M in THF) was then added to the vial and the mixture was shaken for an hour on a rotation mixer. The solid was then centrifuged, washed with THF twice, and transferred to a glass vial in 0.5 mL THF. 1-octene (160 µL, 1.0 mmol) was then added to the vial. The vial was then placed in a Parr reactor. The reactor was sealed under nitrogen atmosphere and charged with hydrogen to 40 bar. The pressure was released after 8 h, and the MOF catalyst was centrifuged out from suspension and extracted with THF 2-3 times in glove box. The organic extracts were combined and conversions were calculated based on integration of substrate and product peaks in the crude $^1$H NMR spectra.

6.3. Test of "Heterogeneity" of the MOF Catalysis

Scheme 23

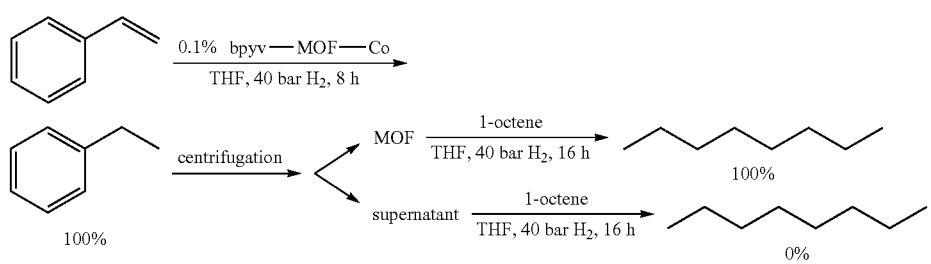

In a nitrogen-filled glove box, bpyv-MOF-Co (2.0 mg, 0.1 mol % Co) in 1.0 mL THF was charged into a glass vial. NaBEt$_3$H (15 µL, 1.0 M in THF) was then added to the vial and the mixture was stirred for 1 hour. The solid was then centrifuged, washed with THF twice, and transferred to a glass vial containing 0.5 mL THF. Styrene (230 µL, 2.0 mmol) was then added to the vial. The vial was then placed in a Parr reactor which was sealed under nitrogen atmosphere and later charged with hydrogen to 40 bar. After 8 h, the pressure was released and the MOF catalyst was centrifuged out from suspension. Conversion of styrene to ethylbenzene (100%) was determined based on integration of substrate and product peaks in the crude $^1$H NMR spectra. Ethylbenzene was afforded quantitatively (100% yield) as determined by $^1$H NMR spectroscopy.

After the solid and supernatant were separated, 1-octene (320 µL, 2.0 mmol) was added to each of the portions which were later placed in a Parr reactor, sealed under nitrogen and charged with hydrogen to 40 bar. After 16 h, the pressure was released and the supernatant was separated from the solid catalyst when necessary. Conversions of 1-octene to n-octane were determined based on integration of substrate and product peaks in the crude $^1$H NMR spectra to be 100% in presence of MOF and 0% in presence of supernatant. This test thus proved that the MOF is the exact catalyst for olefin hydrogenation.

7. Procedures for Catalytic Hydroboration of Carbonyl Compounds

In a glovebox, bpy-MOF-Co (1.0 mg, 0.05 mol % Ir) was charged into a small vial and 0.5 mL THF was added. Then, 8 µL NaBEt$_3$H (1.0 M in THF) was added to the vial and the mixture was stirred slowly for 1 h in the glovebox. The solid was centrifuged out of suspension and washed with hexane two times. Then, the solid in 5 mL hexane was transferred to a vial, and aldehyde or ketone (1.56 mmol) and pinacolborane (1.70 mmol) was added in the vial. The resultant mixture was stirred at room temperature for 1-2 days in the glovebox and the progress of the reaction was monitored by GC. After complete conversion, the solid was centrifuged out of suspension and extracted with hexane for 2-3 times. The combined organic extracts were concentrated in vacuo to yield the pure product.

8. Procedure for bpyv-MOF-Co Catalyzed Hydroboration of Ketones

In a glovebox, bpyv-MOF-Co (1.0 mg, 0.005 mol % Ir) was charged into a small vial and 0.5 mL THF was added. Then, 8 µL NaBEt$_3$H (1.0 M in THF) was added to the vial and the mixture was stirred slowly for 1 h in the glovebox. The solid was centrifuged out of suspension and washed with hexane two times. Then, the solid in 10 mL hexane was transferred to a vial, and 4-methoxyacetophenone (2.35 g, 15.6 mmol) and pinacolborane (2.68 mL, 17.2 mmol) was added in the vial. The resultant mixture was stirred at room temperature for 1-2 days in the glovebox and the progress of the reaction was monitored by GC. After complete conversion, the solid was centrifuged out of suspension and extracted with hexane for 2-3 times. The combined organic extracts were concentrated in vacuo to yield the pure borate ester product as a colorless oil (4.33 g, 15.6 mmol, 100%).

9. Procedures for Catalytic Hydroboration of Alkenes

In a glovebox, mPT-MOF-Co (1.0 mg, 0.01 mol % Ir) was charged into a small vial and 0.5 mL THF was added. Then, 6 µL NaBEt$_3$H (1.0 M in THF) was added to the vial and the mixture was stirred slowly for 1 h in the glovebox. The solid was centrifuged out of suspension and washed with THF two times. Pinacolborane (0.37 mL, 2.4 mmol) was added to the solid in the vial and then 1-octene (0.31 mL, 2.0 mmol) was added. The resultant mixture was slowly stirred at room temperature for 3 days in the glovebox until complete conversion of 1-octene as monitored by GC. The solid was centrifuged out of suspension and extracted with hexane for 2-3 times. The combined organic extracts were concentrated in vacuo to yield the pure product (0.470 g, 1.96 mmol, 98%).

10. Procedures for mPT-MOF-Co Catalyzed C—H Borylation of Neat Arenes

Scheme 24

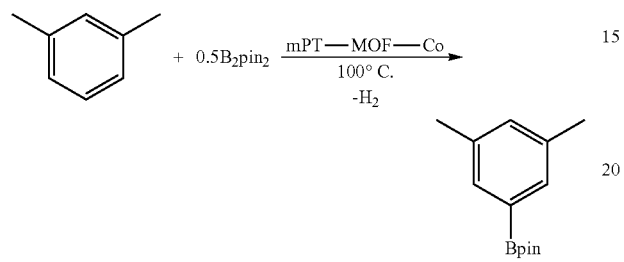

In a glovebox, mPT-MOF-Co (3.0 mg, 0.1 mol % Ir) was charged into a small vial and 0.5 mL THF was added. Then, 20 μL NaBEt$_3$H (1.0 M in THF) was added to the vial and the mixture was stirred slowly for 1 h in the glovebox. The solid was centrifuged out of suspension and washed with THF for two times and with o-xylene for one time. B$_2$pin$_2$ (54.8 mg, 0.216 mmol) in 4.0 mL o-xylene was added to the vial and the resultant mixture was transferred to a Schlenk tube. The tube was heated to reflux under nitrogen at 100° C. for 10 d. The reaction mixture was cooled to room temperature and the solid was centrifuged out of suspension. The extract was passed through a short plug of celite and then concentrated in vacua to give pure 1,2-dimethyl-4-(4,4,5,5-tetramethyl-1,3,2-dioxaborolan-2-yl)benzene as (48.5 mg, 0.209 mmol, 96.8%).

Example 10

MOFs with 1,3-Diketimine (NacNac)-Based Bridging Ligands

Scheme 25:
MOF functionalization

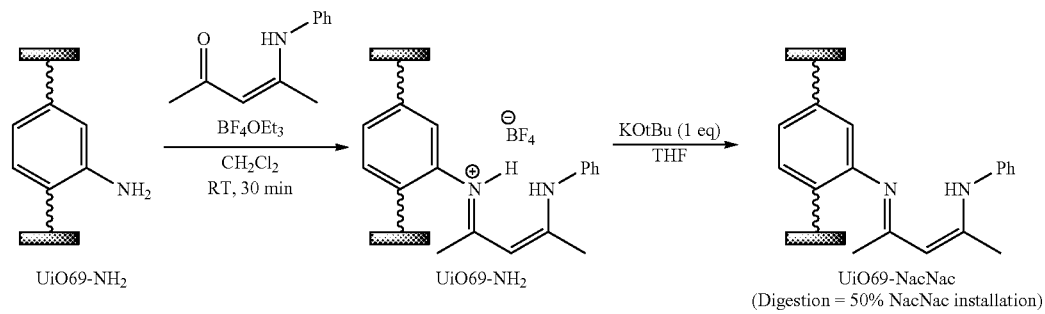

Postsynthetic Metalation (loadings rel. to NacNac in MOF)

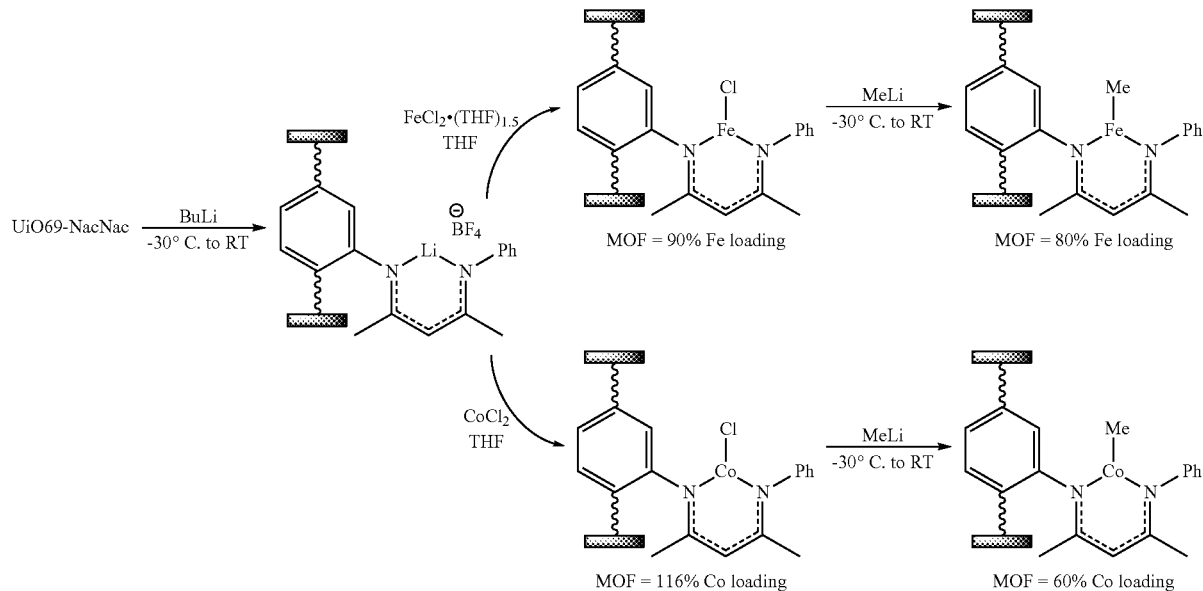

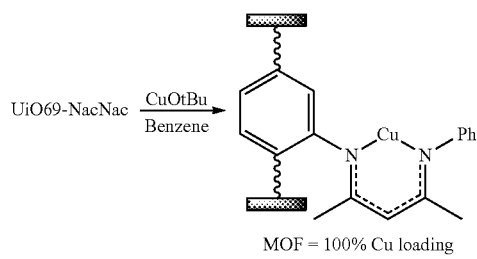

MOF = 100% Cu loading

Fe-Catalyzed Amination

Scheme 26:

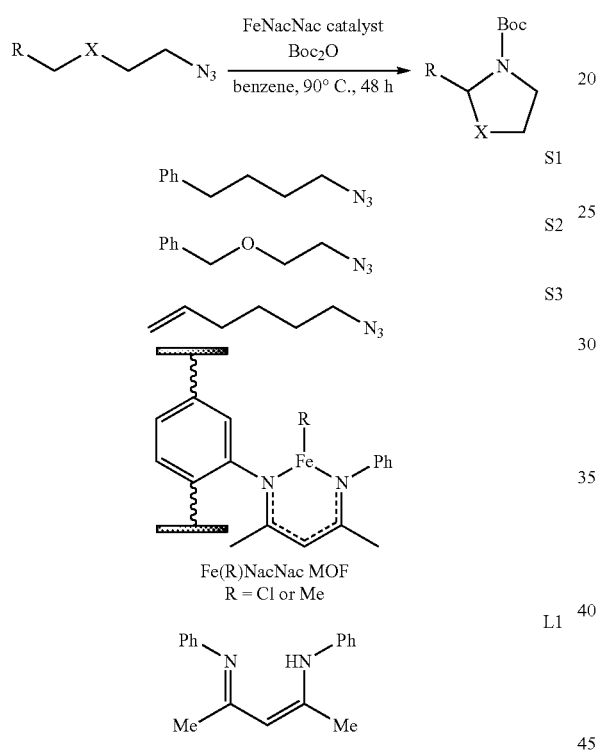

TABLE 18

| Entry | Substrate | Catalyst (loading) | Boc$_2$O (eq) | Yield (%)[a] | TON |
|---|---|---|---|---|---|
| 1 | S1 | Fe(Cl)NacNac MOF (5) | 5 | 23 | 4.6 |
| 2 | S1 | Fe(Cl)NacNac MOF (5) | 10 | 42 | 8.4 |
| 3 | S1 | Fe(Me)NacNac MOF (5) | 10 | 88 | 17.6 |
| 4 | S1 | Homogeneous L1-Fe(Me) control (5) | 10 | 31 | 6.2 |
| 5 | S2 | Fe(Me)NacNac MOF (5) | 10 | 59 | 11.8 |
| 6 | S2 | Homogeneous L1-Fe(Me) control (5) | 10 | 30 | 6.0 |
| 7[b] | S3 | Fe(Cl)NacNac MOF (5) | 10 | 32 | 6.4 |
| 8[b] | S3 | Fe(Me)NacNac MOF (5) | 10 | 65 | 13.0 |
| 9[b] | S3 | Homogeneous L1-Fe(Me) control (5) | 10 | 0 | 0 |

[a]Yields were determined via HNMR with MeNO$_2$ as internal standard.
[b]Yields were determined by HNMR with mesitylene as an internal standard Increasing equivalents of Boc$_2$O leads to higher yields for S1. This can be rationalized as boc is decomposed by the MOF (Entries 1-2). Treatment of Fe(Cl)NacNac MOF with MeLi generates the Fe(Me)NacNac MOF. This catalyst affords the highest product yield (nearly double that of the Fe(Cl)NacNac MOF) (Entry 3).

By comparison, the corresponding homogeneous catalyst prepared in situ from the NacNac ligand L1 (and used subsequently without further purification), is significantly less active giving 31% yield. (Entry 4)

To examine the substrate scope, other substrates were prepared. Under the optimized conditions found for S1, the heterocyclic oxazolidine product can be prepared from substrate S2 in 59% yield (Entry 5).

The corresponding homogeneous catalyst prepared from L1 gives approximately half the yield provided from that of the MOF catalyst.

To test a substrate with additional functionality, the alkene substituent was used (S3). The Fe(Cl)NacNac MOF was effective at producing the product in 32% yield with only 5% starting material remaining. The Fe(Me)NacNac MOF was nearly twice as active affording the product in 65% yield and <3% starting material remaining.

While the homogeneous L1-FeCl catalyst was found to be catalytically active, producing cyclized product in 47% yield with TON of 9.4, the L1-Fe(Me) catalyst was inactive. In both examples, no starting material remained, which suggests either starting material decomposition under homogeneous catalysis.

TONs are consistently higher for C—H amination utilizing the NacNac MOF versus Betley's amination catalyst. For substrate S1, MOF is more than 3 times more active, for S2, the MOF is 4.9 times more active, and for S3 nearly 2 times more active.

TABLE 19

| Entry | Substrate | Betley's optimal TON | NacNac MOF optimal TON |
|---|---|---|---|
| 1 | S1 | 5.7 | 17.6 |
| 2 | S2 | 2.4 | 11.8 |
| 3 | S3 | 7.2 | 13.0 |

Co-Catalyzed Hydrogenation

Scheme 27:

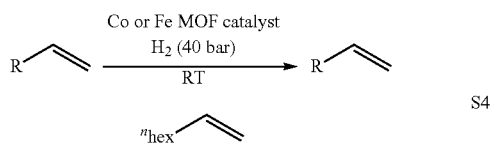

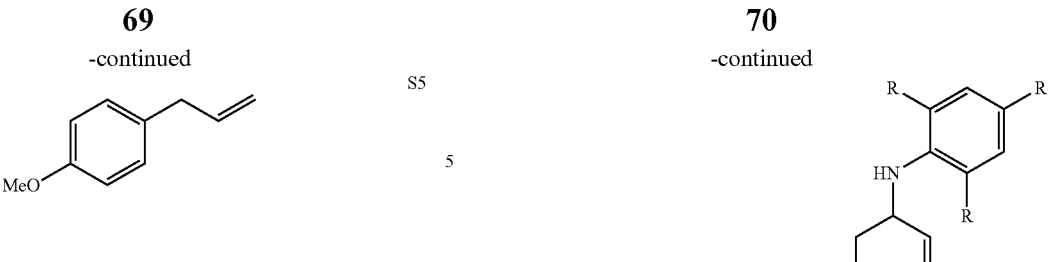

S5

TABLE 20

| Entry | Substrate | Catalyst (loading) | Rxn time (days) | Conversion (%)[a] | TON |
|---|---|---|---|---|---|
| 1 | S4 | Fe(H)NacNac MOF (0.1) | 1 | 10 | 100 |
| 2 | S4 | Co(H)NacNac MOF (0.01) | 1 | 42 | 4200 |
| 3 | S4 | Co(Me)NacNac MOF (0.005) | 1 | 100 | >20000 |
| 4 | S5 | Fe(H)NacNac MOF (0.1) | 1 | 24 | 240 |
| 5 | S5 | Co(H)NacNac MOF (0.1) | 1 | 100 | 1000 |
| 6 | S5 | Co(H)NacNac MOF (0.01) | 1 | 9 | 900 |
| 7 | S5 | Co(Me)NacNac MOF (0.005) | 1 | 30 | 6000 |
| 8 | S5 | Co(Me)NacNac MOF (0.005) | 4 | 50 | 10000 |
| 9 | S5 | Co(Me)NacNac MOF (0.005) | 7 | 62 | 12400 |

[a]Conversions were determined either via HNMR or GC-MS.

Treatment of the Fe(Cl)NacNac MOF with NaBEt$_3$H affords the Fe(H)NacNac MOF. At 0.1 mol % catalyst loadings, only 10% conversion of 1-octene (S4) to n-octane is observed (entry 1).

Co(H)NacNac MOF, prepared from Co(Cl)NacNac MOF in an analogous manner, was more active than the Fe at hydrogenating 1-octene; catalyst loading could be lowered to 0.01 mol % giving a TON of 4200 (entry 2). Co(Me)NacNac MOF, prepared from addition of MeLi to the Co(Cl)NacNac MOF, was able to achieve an even higher TON at >20,000 in one batch.

Hydrogenation of 4-methoxyallylbenzene (S5) with the NacNac MOF is generally less reactive than 1-octene. Comparing the Fe(H)NacNac MOF and the Co(H) NacNac MOF at 0.1 mol % loadings (entries 4-5), found Co to be at least 4× more active than Fe. In trying to determine the actual TON, reducing the catalyst loading to 0.01 mol % found we have reached our maximum TON for a 24 hour time period (entry 6). The Co(Me)NacNac MOF was significantly more active. At 0.005 mol % catalyst loadings over 7 days, a TON of 12,400 was obtained.

Cu-Catalyzed Amination

Scheme 28:

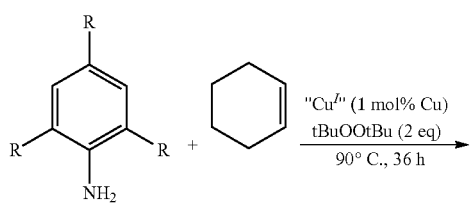

S6, R = Me
S7, R = H
S8, R = Cl

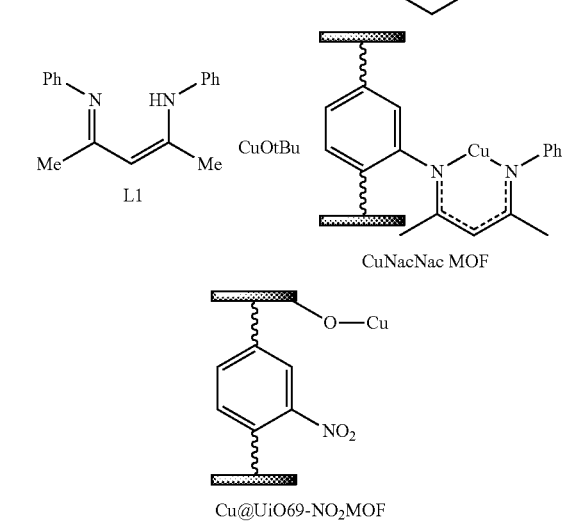

TABLE 21

| Entry | Substrate | Catalyst (loading) | time (hr) | Yield (%)[a] | TON |
|---|---|---|---|---|---|
| 1 | S6 | CuNacNac MOF (1) | 36 | 78 | 78 |
| 2 | S6 | CuNacNac MOF (0.2) | 4.5 days | 54 | 27 |
| 3[b] | S6 | CuOtBu (1) | 36 | 56 | 56 |
| 4 | S6 | Homogeneous L1-Cu (1) | 36 | 65 | 65 |
| 5 | S6 | Homogeneous L1-Cu (0.2) | 4.5 days | 90 | 450 |
| 6 | S7 | CuNacNac MOF (1) | 36 | 18 | 18 |
| 7 | S7 | Homogeneous L1-Cu (1) | 36 | 22 | 22 |
| 8 | S8 | CuNacNac MOF (1) | 36 | 10 | 10 |
| 9 | S8 | Homogeneous L1-Cu (1) | 36 | 40 | 40 |

[a]Yields were determined via H NMR with MeNO$_2$ as internal standard.
[b]43% diazene was formed CuNacNac MOF is efficient at promoting the amination reaction between 2,4,6-trimethyl aniline and cyclohexene (entry 1). Notably, the catalyst loading could be reduced to 0.2 mol % and still obtain a TON of 270 with a 4.5 day reaction time (entry 2).

Comparing the TON

TABLE 22

| Entry | Substrate | Warren's optimal TON[a] | NacNac MOF optimal TON[b] |
|---|---|---|---|
| 1 | S6 | 47 | 270 |
| 2 | S7 | 36 | 18 |
| 3 | S8 | 97 | 10 |

[a]Reaction conditions: 1 mol % Cu(2,6-DiClsubstituted NacNac), 90° C., 24 h.
[b]entry 1, CuNacNac MOF (0.2 mol % Cu), 90° C., 36 h. entries 2-3: CuNacNac MOF (1 mol % Cu), 90° C., 36 h.

Scheme: 29

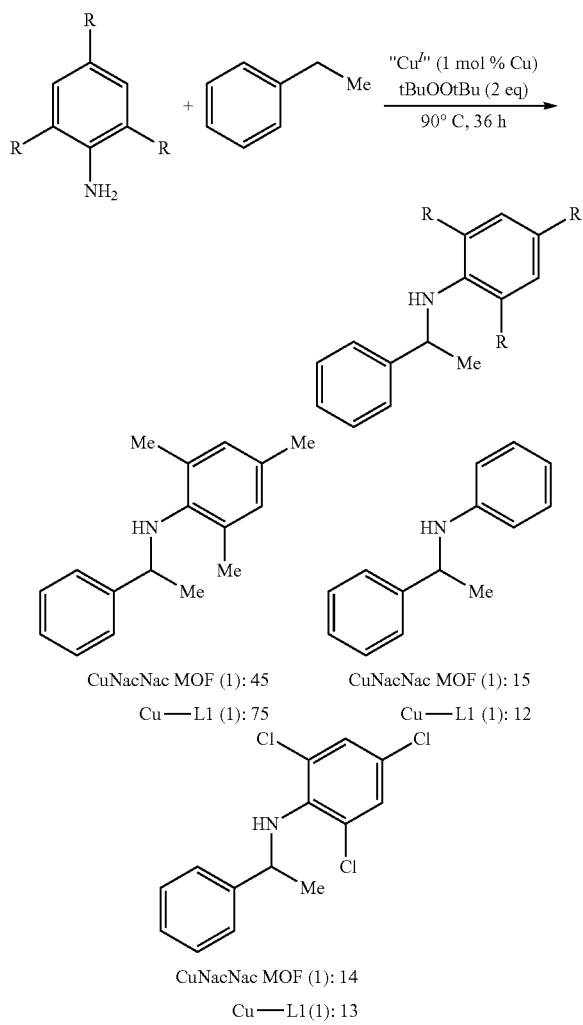

This methodology can be expanded to other substrates capable of H-atom abstraction. Ethyl benzene is active for the C—H amination with substituted anilines. The reactivity pattern for the anilines followed that observed with cyclohexene. That is, the tri-Me substituted aniline is more active than aniline which is more active than the tri-Cl substituted aniline. Still, CuNacNac MOF (1 mol % Cu) afforded 45% yield of aminated ethyl benzene when 2,4,6-trimethylbenzene was used.

Example 11

Bipyridine- and Phenanthroline-Based Metal-Organic Frameworks for Highly Efficient and Tandem Catalytic Organic Transformations Via Directed C—H Activation Disclosed in this Example is the synthesis of a series of robust and porous bipyridyl- and phenanthryl-based metal-organic frameworks (MOFs) of UiO topology (BPV-MOF, mBPV-MOF and mPT-MOF) and their postsynthetic metalation to afford highly active single-site solid catalysts. While BPV-MOF was constructed from only bipyridyl-functionalized dicarboxyate linker, both mBPV- and mPT-MOF were built with a mixture of bipyridyl- or phenanthryl-functionalized and unfunctionalized dicarboxylate linkers. The postsynthetic metalation of these MOFs with [Ir(COD)(OMe)]$_2$ provided Ir-functionalized MOFs (BPV-MOF-Ir, mBPV-MOF-Ir and mPT-MOF-Ir), which are highly active catalysts for tandem hydrosilylation of aryl ketones and aldehydes followed by ortho-silylation of benzylicsilyl ethers as well as C—H borylation of arenes using B$_2$pin$_2$. Both mBPV-MOF-Ir and mPT-MOF-Ir catalysts displayed superior activities compared to BPV-MOF-Ir due to the presence of larger open channels in the mixed-linker MOFs. Impressively, mBPV-MOF-Ir exhibited high TONs of up to 17000 for C—H borylation reactions and was recycled more than 15 times. The mPT-MOF-Ir system is also active in catalyzing tandem dehydrosilylation/dehydrogenative cyclization of N-methylbenzyl amines to azasilolanes in the absence of a hydrogen-acceptor. The MOF-Ir catalysts were significantly more active (up to 95 times) and stable than their homogeneous counterparts for all three reactions, strongly supporting the beneficial effects of active site isolation within MOFs. This Example further illustrates the ability to increase MOF open channel sizes by using the mixed linker approach and shows the enormous potential of developing highly active and robust single-site solid catalysts based on MOFs containing nitrogen-donor ligands for important organic transformations.

Thus, in this Example, disclosed is the design and synthesis of elongated bipyridyl- and phenanthryl-containing UiO MOFs with larger channels and their postsynthetic metalation with an iridium complex to afford highly active and efficient single-site solid catalysts for several important organic reactions via directed C—H activation. UiO-type MOFs built from Zr$_6$($\mu_3$-O)$_4$($\mu_3$-OH)$_4$ secondary building units (SBUs) and linear dicarboxylate linkers are highly stable under various reaction conditions, and thus provide an ideal system for exploring catalytic applications. Furthermore, the UiO MOF topology is amenable to the incorporation of a wide variety of functionalities into the dicarboxylate linkers to lead to numerous novel functional materials for many important applications. A mixed linker strategy of using both the functionalized linkers and catalytically inactive linkers was also developed in this Example to afford mixed-linker MOFs with much larger open channels and pores to allow for facile diffusion of the substrates and products through the MOF channels. These Ir-functionalized MOFs have been employed as active, robust, and reusable solid catalysts in three important organic transformations: C—H borylation of arenes, tandem hydrosilylation of aryl ketones and aldehydes followed by hydroxyl-directed ortho-silylation, and tandem dehydrocoupling of N-methylbenzyl amines with Et$_2$SiH$_2$ to (hydrido)silyl amines and subsequent intramolecular dehydrogenative cyclization. Analogous homogeneous bipyridyl- and phenanthryl-iridium complexes were also prepared in order to compare their catalytic activities with those of the MOF-based catalysts. It was demonstrated that the MOF-Ir catalysts are significantly more active than their homogeneous controls in both borylation and silylation reactions[17], revealing the crucial role of active site isolation within MOFs. Additionally, these solid MOF-catalysts can overcome many fundamental difficulties associated with homogeneous catalysts such as capital- and labor-intensive ligand design in order to avoid multimolecular catalyst decomposition, leaching of toxic metal ions and complexes into the organic products, and the limitation of solvent choices due to poor solubility of some homogenous catalysts in nonpolar solvents.

BPV-MOF, mBPV-MOF, and mPT-MOF were constructed from both bipyridyl- or phenanthryl-functionalized dicarboxylate linker and the Zr-based SBU to afford UiO frameworks as shown in Schemes 30 and 31. The bipyridyl-containing dicarboxylate linker, $H_2BPV$, was synthesized from 5,5'-dibromo-2,2'-bipyridine in two steps (Scheme 30). The Suzuki coupling between 5,5'-dibromo-2,2'-bipyridine and methyl acrylate followed by saponification provided $H_2BPV$ in 60% overall yield. The phenantholine-containing dicarboxylate linker, $H_2PT$, was prepared from phenanthroline in three steps in a 22% overall yield (Scheme 31).

Scheme 30. Synthesis of BPV—MOF and mBPV—MOF[a]

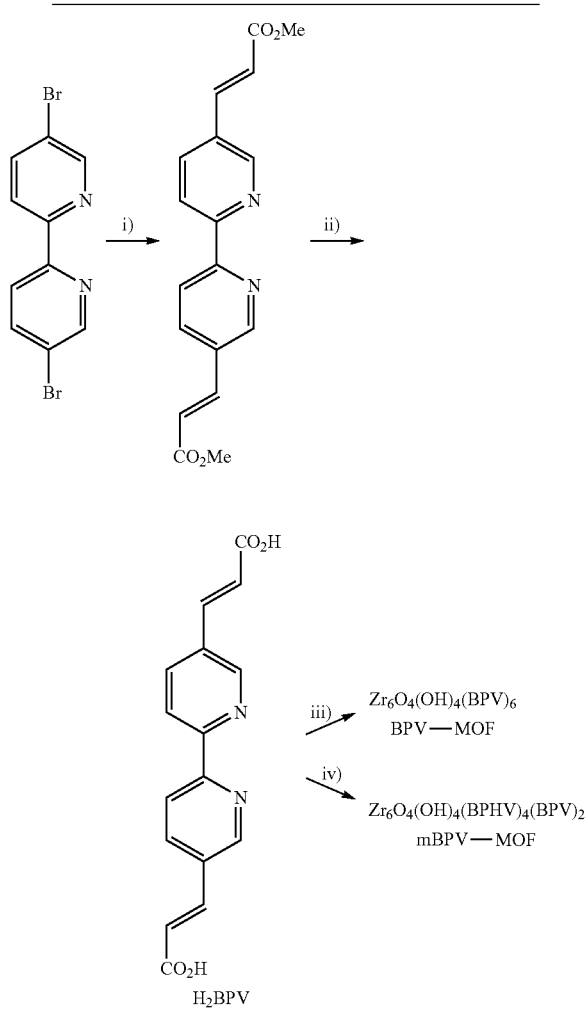

[a]Reagents: (i) methyl acrylate, Pd(OAc)$_2$, P(o-tol)$_3$, NEt$_3$, DMF, 120° C., 2 d; (ii) NaOH, EtOH, H$_2$O, reflux; (iii) ZrCl$_4$, DMF, TFA, 100° C., 5 d; (iv) H$_2$BPHV, ZrCl$_4$, DMF, TFA, 100° C., 5 d.

The solvothermal reaction between $ZrCl_4$ and $H_2BPV$ in the presence of dimethylformamide (DMF) and trifluoroacetic acid (TFA) at 100° C. afforded BPV-MOF with a UiO framework of $Zr_6O_4(OH)_4(BPV)_6$ in 40% yield. In contrast, mBPV-MOF was synthesized in 40% yield by heating $ZrCl_4$ with $H_2BPV$ and 4,4'-bis(carboxyethenyl)-1,1'-biphenyl ($H_2BPHV$) (in a 1:2 molar ratio) in the presence of DMF and TFA at 100° C. Similarly, mPT-MOF was synthesized in 45% yield by heating $ZrCl_4$ and a mixture of $H_2PT$ and 4,4'-bis(carboxyphenyl)-2-nitro-1,1'-biphenyl ($H_2TPHN$) in 1:2 molar ratio in a DMF solution in the presence of TFA at 100° C. The presence of bipyridyl- and phenanthryl-containing dicarboxylate linkers in mBPV-MOF and mPT-MOF, respectively, was established and quantified by taking $^1$H NMR spectra of the digested MOFs. NMR studies consistently revealed that the ratio of biphenyl and bipyridine in the mBPV-MOF or the ratio of tetraphenyl and phenanthroline in mPT-MOF is approximately 2:1, consistent with the molar ratio in the feed. Nitrogen sorption measurements indicate that both mBPV-MOF and mPT-MOF are highly porous with a BET surface area of 1207 m$^2$/g and 3834 m$^2$/g respectively and pore sizes of 7 Å and 7.7 Å respectively.

Figure 6A:
FIG. 6A is a schematic drawing showing synthesis of BPHV-MOF from Example 11.
Figure 6B:
FIG. 6B is a schematic drawing showing synthesis of TPHN-MOF from Example 11.

The structures of BPV-MOF and mBPV-MOF were established by comparing the powder X-ray diffraction (PXRD) patterns of the MOFs with the predicted pattern from a single crystal structure of BPHV-MOF which was synthesized from $ZrCl_4$ and 4,4'-bis(carboxyethenyl)-1,1'-biphenyl ($H_2BPHV$) linker in the presence of DMF and TFA at 80° C. See FIG. 6A. A single-crystal X-ray diffraction study revealed that BPHV-MOF adopts the UiO structure, with the $Zr_6(\mu_3$-$O)_4(\mu_3$-$OH)_4$ SBUs connected by the BPHV bridging linkers to afford the 12-connected fcu topology. However, BPHV-MOF crystallizes in a lower symmetry space group of $I\bar{4}$ due to the bending nature of the BPHV linker. The broadening of (101) peak and appearance of several other peaks suggest structural distortion in the powder samples, which has been observed in other nanoscale MOFs (He, C.; Lu, K.; Liu, D.; Lin, W. J. Am. Chem. Soc. 2014, 136, 5181). In the present case, the bent nature of the BPHV and BPV linkers provides additional mechanisms for structural distortions from the single crystal structure. Similarly, the structure of mPT-MOF was established by comparing the PXRD patterns with the simulated pattern from a single crystal structure of TPHN-MOF which was synthesized from $ZrCl_4$ and 4,4'-bis(carboxyphenyl)-2-nitro-1,1'-biphenyl ($H_2TPHN$) under similar conditions. See FIG. 6B. TPHN-MOF adopts a typical UiO structure and crystallizes in the cubic $Fm\bar{3}m$ space group.

Scheme 31. Synthesis of mPT-MOF[a]

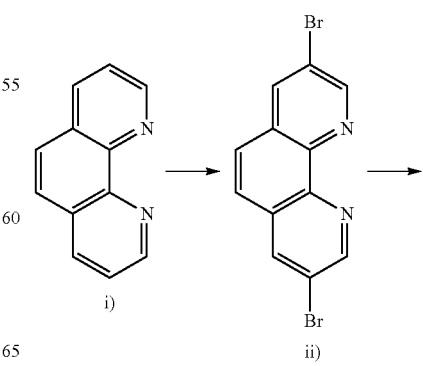

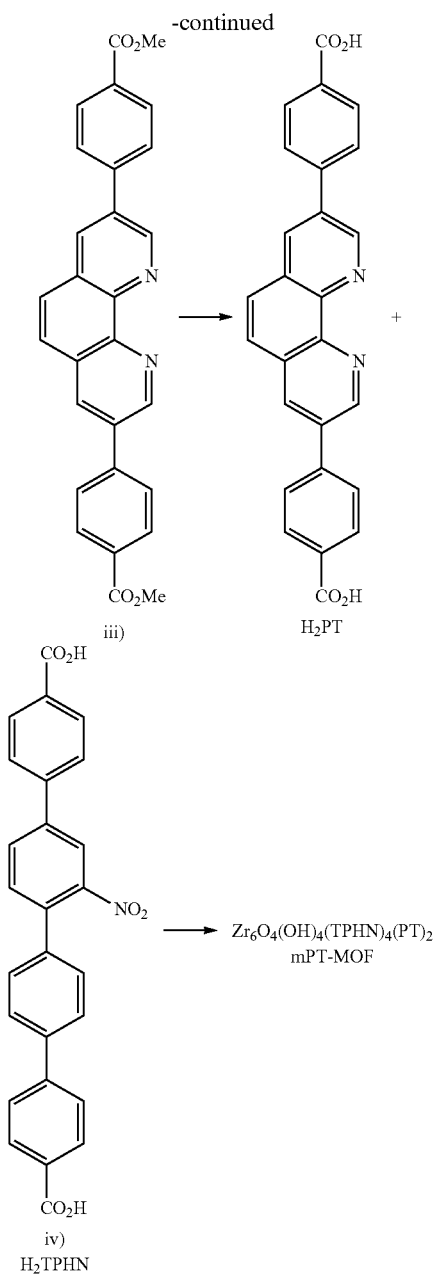

*Reagents: (i) Br₂, S₂Cl₂, pyridine, n-BuCl, reflux, 12 h; (ii) 4-acetylphenylboronic acid, Pd(PPh₃)₂, CsF, DME, 100° C., 3 d; (iii) aq NaOH EtOH; (iv) ZrCl₄, DMF, TFA, 100° C., 5 d.

Figure 6C:
FIG. 6C is a schematic drawing showing the post-synthetic metalation of BPV-MOF from Example 11.
Figure 7A:
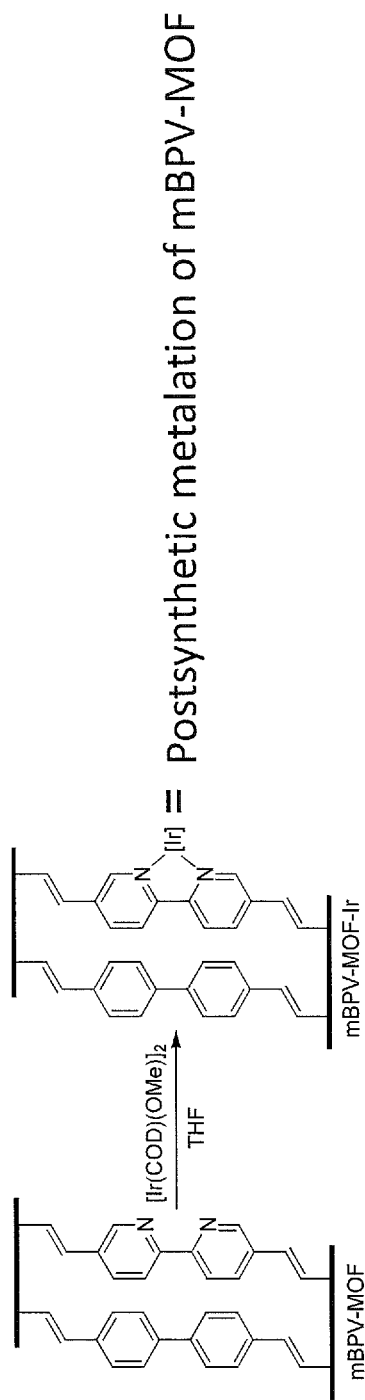
FIG. 7A is a schematic drawing showing postsynthetic metalation of mBPV-MOF from Example 11.
Figure 7B:
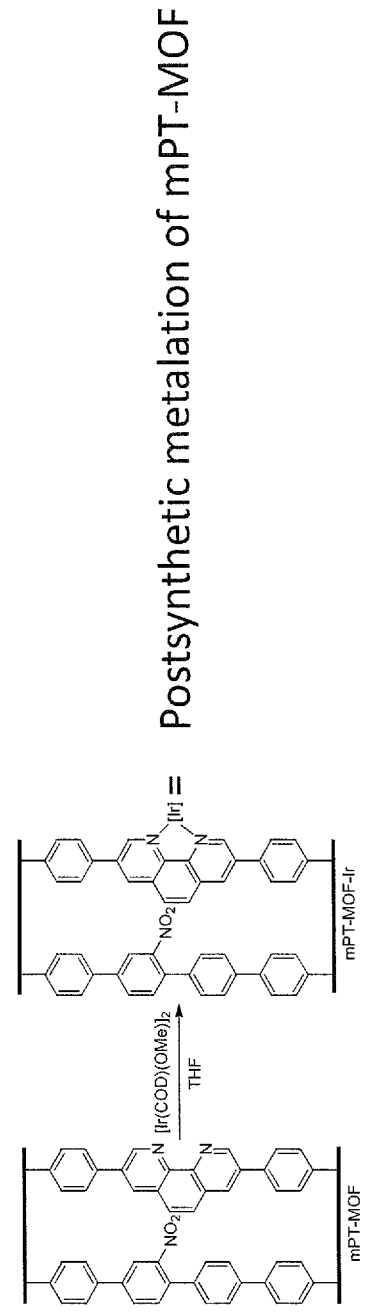
FIG. 7B is a schematic drawing showing postsynthetic metalation of mPT-MOF from Example 11.

The postsynthetic metalation of BPV-MOF was performed by treating BPV-MOF with 2.0 equiv of [Ir(COD)(OMe)]$_2$ in THF to afford BPV-MOF-Ir as a deep purple solid (FIG. 6C). Similarly, mBPV-MOF-Ir and mPT-MOF-Ir were prepared as a deep purple and deep green solid respectively by the treatment of mBPV-MOF and mPT-MOF with 1.0 equiv of [Ir(COD)(OMe)]$_2$ in THF (FIGS. 7A and 7B), respectively. Inductively coupled plasma-mass spectroscopy (ICP-MS) analyses of Ir/Zr ratio of the digested metalated MOFs revealed the Ir loadings of 65%, 16% and 20% with respect to the Zr centers for BPV-MOF-Ir, mBPV-MOF-Ir and mPT-MOF-Ir, respectively. mPT-MOF was also metalated with [IrCl(COD)]$_2$ in THF to obtain mPT-MOF-Ir(COD)-Cl as a green solid at a 12% Ir loading. Because mBPV-MOF-Ir and mPT-MOF-Ir only contain ⅓ functionalized linkers, these Ir loadings correspond to the metalation of 48% and 61% of the BPV and PT linkers in these mMOFs. The crystallinity of all the MOFs was maintained upon metalation as shown by similar PXRD patterns of MOFs and MOF-Ir materials. BPV-MOF-Ir, mBPV-MOF-Ir and mPT-MOF-Ir have BET surface area of 106, 563, and 1828 m²/g respectively, and pore sizes of 5.8, 5.9, and 6.7 Å respectively. The smaller surface areas and pore sizes of metalated MOFs compared to their pristine analogs are due to the presence of Ir and associated ligands in the MOF cavities.

Homogeneous control experiments were performed in order to identify the Ir species formed from postsynthetic metalation of the MOFs. Treatment of [Ir(COD)(OMe)]$_2$ with H$_2$BPV or Me$_2$BPV at room temperature. afforded (H$_2$BPV)Ir(COD)(OMe) and (Me$_2$BPV)Ir(COD)(OMe), respectively. The identities of both Ir complexes were established by NMR spectroscopy and mass spectrometry. These Ir complexes are air- and water-sensitive, and rapidly decomposed under MOF digestion conditions. However, because H$_2$BPV or Me$_2$BPV ligands were completely metalated to form (H$_2$BPV)Ir(COD)(OMe) or (Me$_2$BPV)Ir (COD)(OMe) at room temperature, we can infer that the identities of the Ir species in the metalated MOFs as Ir(L)(COD)(OMe) (L=BPV or PT) complexes.

BPV-MOF-Ir, mBPV-MOF-Ir and mPT-MOF-Ir are all active in catalyzing the hydrosilylation of aryl ketones to benzylicsilyl ethers and subsequent intramolecular ortho-silylation of benzylicsilyl ethers to give benzoxasiloles (Table 23) (Simmons, E. M.; Hartwig, J. F. *J. Am. Chem. Soc.* 2010, 132, 17092). Benzoxasiloles are important in organic synthesis and can be converted to phenols by Tamao-Fleming oxidation (Simmons, E. M.; Hartwig, J. F. *J. Am. Chem. Soc.* 2010, 132, 17092; Tamao, K.; Ishida, N.; Tanaka, T.; Kumada, M. *Organometallics* 1983, 2, 1694; Jones, G. R.; Landais, Y. *Tetrahedron* 1996, 52, 7599; Ihara, H.; Suginome, M. *J. Am. Chem. Soc.* 2009, 131, 7502) or to biaryl derivatives by Hiyama cross-coupling reactions (Denmark, S. E.; Sweis, R. F. *Acc. Chem. Res.* 2002, 35, 835). In homogeneous catalysis pioneered by Hartwig and coworkers, the hydrosilylation of ketones was catalyzed by [Ir(COD)(OMe)]$_2$, and the subsequent intramolecular ortho-silylation of benzylicsilyl ethers was catalyzed by phenathroline-derived Ir(I) complex in presence of norborene as the hydrogen acceptor. (Simmons, E. M.; Hartwig, J. F. *J. Am. Chem. Soc.* 2010, 132, 17092; Hartwig, J. F. *Acc. Chem. Res.* 2011, 45, 864). This homogeneous reaction requires relatively high catalyst loadings and the use of a hydrogen acceptor. In MOF-Ir catalyzed silylation reactions, the hydrosilylation of ketones proceeded at room temperature, but the dehydrogenative ortho-silylation of benzylicsilyl ethers required elevated temperatures. Screening experiments revealed that the intramolecular ortho-silylation gave the highest turnover frequency when the reaction mixture was refluxed in n-heptane under nitrogen atmosphere at 115° C. At 0.1 mol Ir loading, BPV-MOF-Ir provided benzylicsilyl ether 2a in complete conversion upon treatment of acetophenone with 1.05 equiv Et$_2$SiH$_2$ in n-heptane for 18 h at room temperature. Refluxing the resultant mixture at 115° C. for 8 d afforded corresponding benzoxasilole 3a with 72% conversion. Under identical reaction conditions, 0.1 mol mBPV-MOF-Ir and mPT-MOF-Ir gave complete conversions of 2a and afforded 3a in good isolated yields (Table 23, entries 2 and 4). The dehydrogenative ortho-silylation of benzylicsilyl ethers was accompanied by the generation of a stoichiometric amount of H$_2$, which was identified and quantified by GC analysis. Importantly, no $H_2$-acceptor was needed, which represents an improvement over the reported homogeneous C—H silylation reactions in terms of atom economy. The PXRD patterns of MOFs recovered from the silylation reactions remained the same as those of freshly prepared MOF-Ir precatalysts, indicating that the MOF frameworks are stable under the catalytic conditions. The higher catalytic activities of both mBPV-MOF-Ir and mPT-MOF-Ir compared to BPV-MOF-Ir were also observed for other substrates (Table 23; Entries 7-9, 15-18, 19-21). The enhanced activity of mMOF catalysts compared to BPV-MOF-Ir is likely due to the presence of more open channels, which facilitates diffusion of substrates and products through the channels of mMOFs. Directly refluxing a mixture of acetophenone and $Et_2SiH_2$ in n-heptane at 115° C. using 0.01 mol % of mPT-MOF-Ir resulted in the complete conversion of 1a, however, afforded benzoxasilole 3a in a lower yield (82%), presumably due to the decomposition of the Ir-hydride intermediate generated during the hydrosilylation step at higher temperatures.

TABLE 23

MOF-Ir Catalyzed Tandem Hydrosilylation of Ketones and Intramolecular ortho-Silylation of Benzylicsilyl Ethers to Prepare Benzoxasiloles[a]

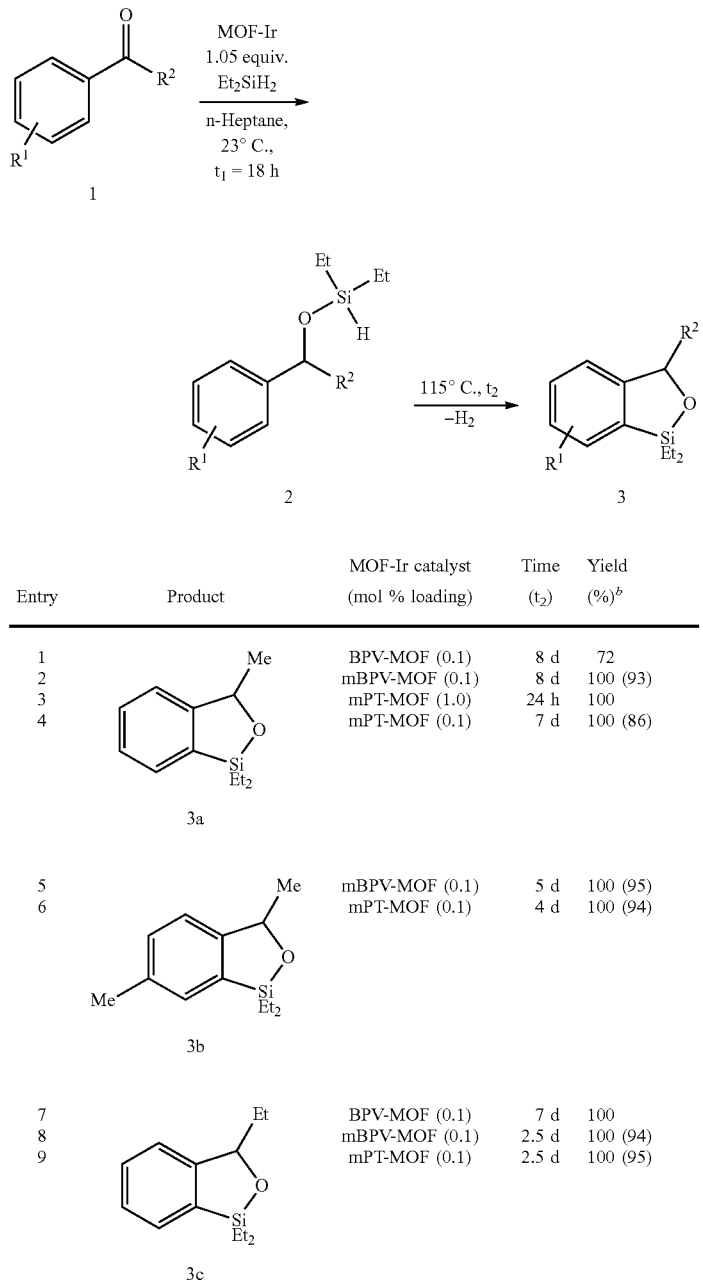

| Entry | Product | MOF-Ir catalyst (mol % loading) | Time ($t_2$) | Yield (%)[b] |
|---|---|---|---|---|
| 1 | 3a | BPV-MOF (0.1) | 8 d | 72 |
| 2 |  | mBPV-MOF (0.1) | 8 d | 100 (93) |
| 3 |  | mPT-MOF (1.0) | 24 h | 100 |
| 4 |  | mPT-MOF (0.1) | 7 d | 100 (86) |
| 5 | 3b | mBPV-MOF (0.1) | 5 d | 100 (95) |
| 6 |  | mPT-MOF (0.1) | 4 d | 100 (94) |
| 7 | 3c | BPV-MOF (0.1) | 7 d | 100 |
| 8 |  | mBPV-MOF (0.1) | 2.5 d | 100 (94) |
| 9 |  | mPT-MOF (0.1) | 2.5 d | 100 (95) |

TABLE 23-continued

MOF-Ir Catalyzed Tandem Hydrosilylation of Ketones and Intramolecular ortho-Silylation of Benzylicsilyl Ethers to Prepare Benzoxasiloles[a]

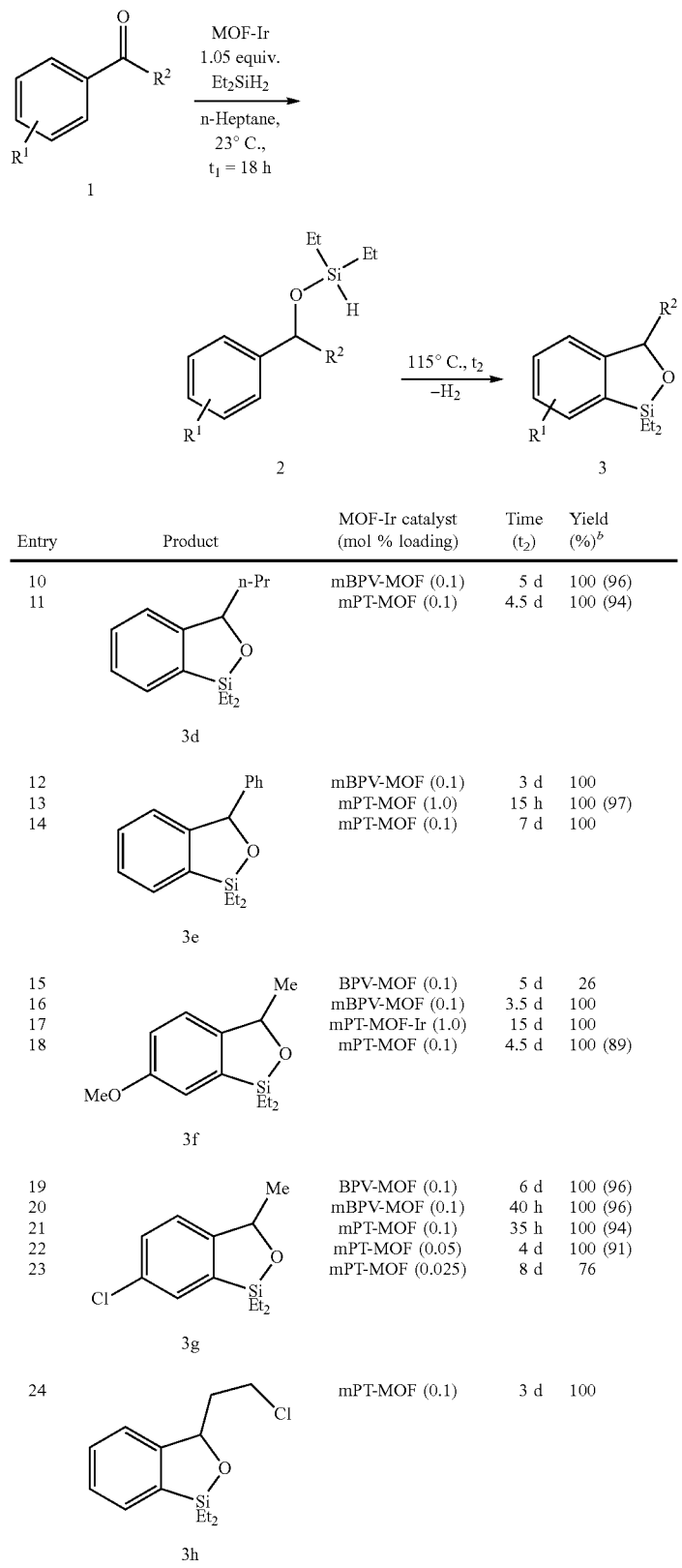

| Entry | Product | MOF-Ir catalyst (mol % loading) | Time (t₂) | Yield (%)[b] |
|---|---|---|---|---|
| 10 | 3d (n-Pr) | mBPV-MOF (0.1) | 5 d | 100 (96) |
| 11 | | mPT-MOF (0.1) | 4.5 d | 100 (94) |
| 12 | 3e (Ph) | mBPV-MOF (0.1) | 3 d | 100 |
| 13 | | mPT-MOF (1.0) | 15 h | 100 (97) |
| 14 | | mPT-MOF (0.1) | 7 d | 100 |
| 15 | 3f (Me, MeO) | BPV-MOF (0.1) | 5 d | 26 |
| 16 | | mBPV-MOF (0.1) | 3.5 d | 100 |
| 17 | | mPT-MOF-Ir (1.0) | 15 d | 100 |
| 18 | | mPT-MOF (0.1) | 4.5 d | 100 (89) |
| 19 | 3g (Me, Cl) | BPV-MOF (0.1) | 6 d | 100 (96) |
| 20 | | mBPV-MOF (0.1) | 40 h | 100 (96) |
| 21 | | mPT-MOF (0.1) | 35 h | 100 (94) |
| 22 | | mPT-MOF (0.05) | 4 d | 100 (91) |
| 23 | | mPT-MOF (0.025) | 8 d | 76 |
| 24 | 3h | mPT-MOF (0.1) | 3 d | 100 |

TABLE 23-continued

MOF-Ir Catalyzed Tandem Hydrosilylation of Ketones and Intramolecular ortho-Silylation of Benzylicsilyl Ethers to Prepare Benzoxasiloles[a]

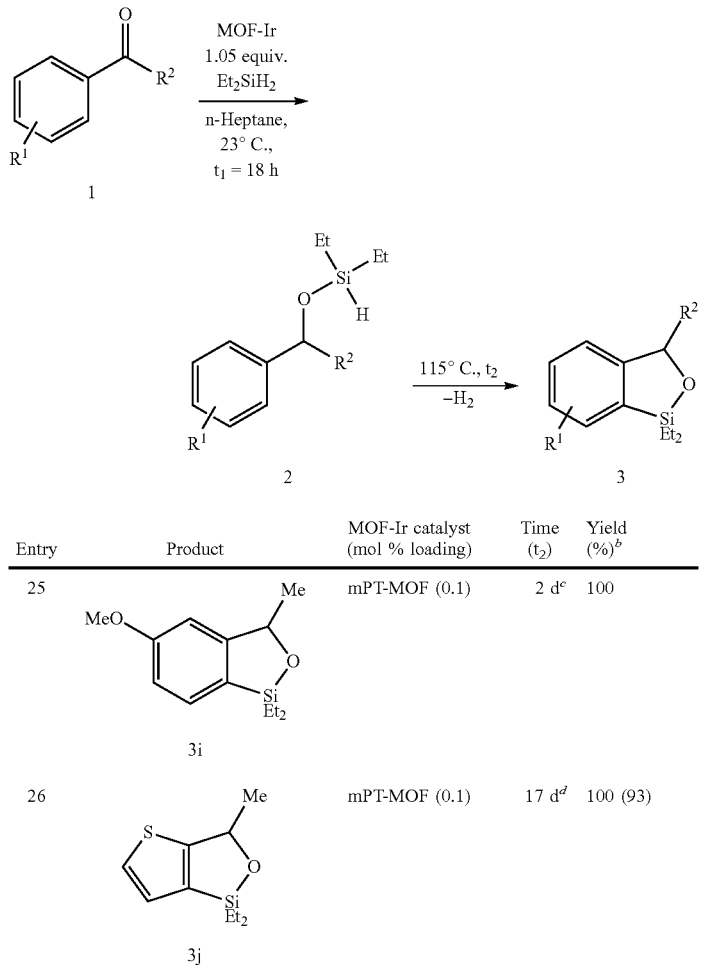

| Entry | Product | MOF-Ir catalyst (mol % loading) | Time ($t_2$) | Yield (%)[b] |
|---|---|---|---|---|
| 25 | 3i | mPT-MOF (0.1) | 2 d[c] | 100 |
| 26 | 3j | mPT-MOF (0.1) | 17 d[d] | 100 (93) |

[a]Reaction conditions: 5.0 mg of MOF-Ir (0.1 mol % Ir) or other loadings as specified, 4.0 mL of n-heptane, 115° C., reflux under $N_2$. [b]Isolated yield in the parenthesis. [c]$t_1$ = 42 h. [d]$t_1$ = 4 d.

Tandem hydrosilylation of aryl ketones and intramolecular ortho-silylation reactions catalyzed by mBPV-MOF-Ir and mPT-MOF-Ir have a broad substrate scope as shown in Table 23. At 0.1 mol % Ir loading, mixed-linker MOFs gave complete conversions of both the aryl ketones (1a-j) and the in situ generated benzylicsilyl ethers (2a-j) in absence of H-acceptor to afford benzoxasiloles (3a-j) in excellent yields (86-100%). Monoalkyl (3a-d), aryl (3e), alkoxy (3f and 3i), and halogen (3g-h) substituents were all tolerated under the reaction conditions. Benzoxasiloles could also be prepared from sec-benzyl alcohols by dehydrocoupling of alcohols to benzylicsilyl ethers at room temperature, followed by intramolecular cyclization at 115° C. For example, 3c was afforded from 1-phenyl-1-propanol (1c) in 94% and 95% yields for mBPV-MOF-Ir and mPT-MOF-Ir respectively (Table 23, entries 8 and 9). Additionally, heteroaromatic benzoxasilole (3j) was also obtained in 93% yield with 0.1 mol % of mPT-MOF-Ir (Table 23, entry 26). Notably, a turnover number (TON) of 3200 was observed for mPT-MOF-Ir with 1g as the substrate (Table 23, entry 23).

Figure 8B:
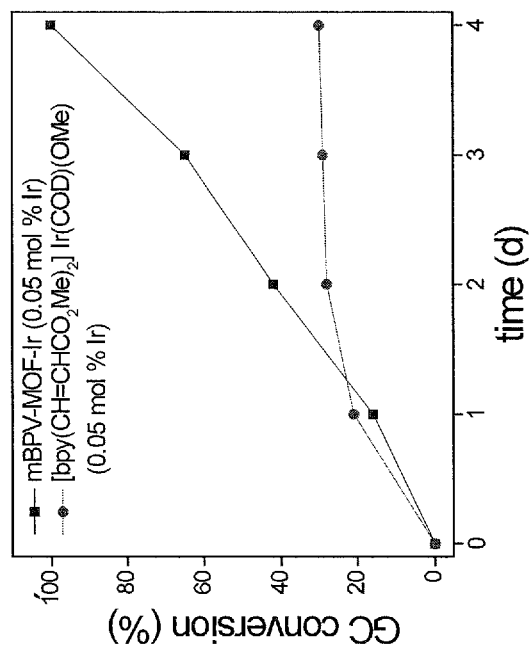
FIG. 8B shows plots from Example 11 of GC conversion (%) vs time for ortho-silylation of 2 g using mBPV-MOF-Ir (0.05 mol %) (squares) and [bpy(CH=CHCO$_2$Me)$_2$]Ir(COD)(OMe) (0.05 mol %) (circles) as catalysts in n-heptane at 115° C.
Figure 8A:
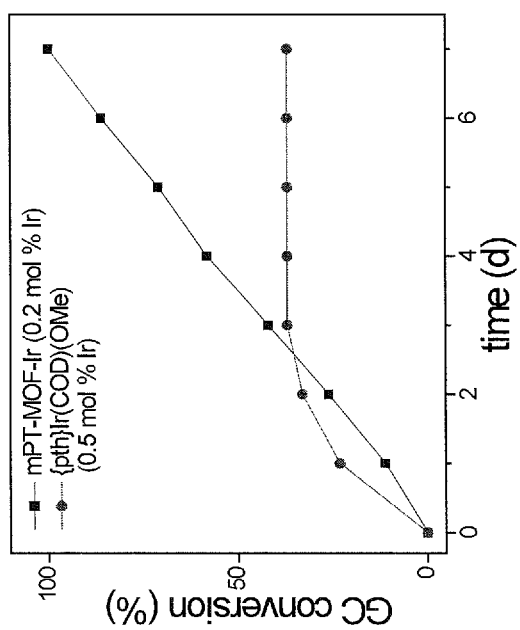
FIG. 8A show plots from Example 11 of GC conversion (%) vs time for ortho-silylation of 5b using mPT-MOF-Ir (0.2 mol %) (squares) and {pth}Ir(COD)(OMe) (0.5 mol %) (circles) as catalysts in n-heptane at 115° C.

Ir-functionalized mixed-linker MOFs are also active in catalyzing hydrosilylation of benzaldehydes (4) and in situ cyclization of the primary (hydrido)silyl ethers (5) under identical reaction conditions to those for aryl ketones (Table 24). Although longer reaction times were required in both steps, full conversions were observed and excellent yields of benzoxasiloles (6) were obtained with 0.5 mol % mBPV-MOF-Ir and mPT-MOF-Ir catalysts. Notably, both mBPV-MOF-Ir and mPT-MOF-Ir catalysts are significantly more active in intramolecular ortho-silylation of benzylicsilyl ethers than their homogeneous control analogs. Under identical conditions, 0.5 mol % of {pth}Ir(COD)(OMe) {pth=3, 8-bis(4-methoxycarbonylphenyl)phenanthroline} afforded 6b in only 37% conversion in three days, after which no further conversion was observed with further heating. In contrast, the conversion of 5b proceeded linearly with time until completion in the presence of 0.2 mol % of the mPT-MOF-Ir catalyst (FIG. 8A). This result indicates that mPT-MOF-Ir is at least 7 times more active than the homogeneous control for the intramolecular silylation reaction. Time dependent GC conversion curves indicated that mBPV-MOF-Ir was also at least 3 times more active its homogeneous control [bpy(CH=CHCO$_2$Me)$_2$]Ir(COD)(OMe) (FIG. 8B). The higher activities of MOF catalysts strongly support the beneficial effect of active site isolation in the MOF framework, which prevents any intermolecular deactivation pathways.

TABLE 24 mBPV-MOF-Ir and mPT-MOF-Ir Catalyzed Tandem Hydrosilylation of Aldehyde and Intramolecular ortho-Silylation of Benzylicsilyl Ethers to Prepare Benzoxasiloles[a]

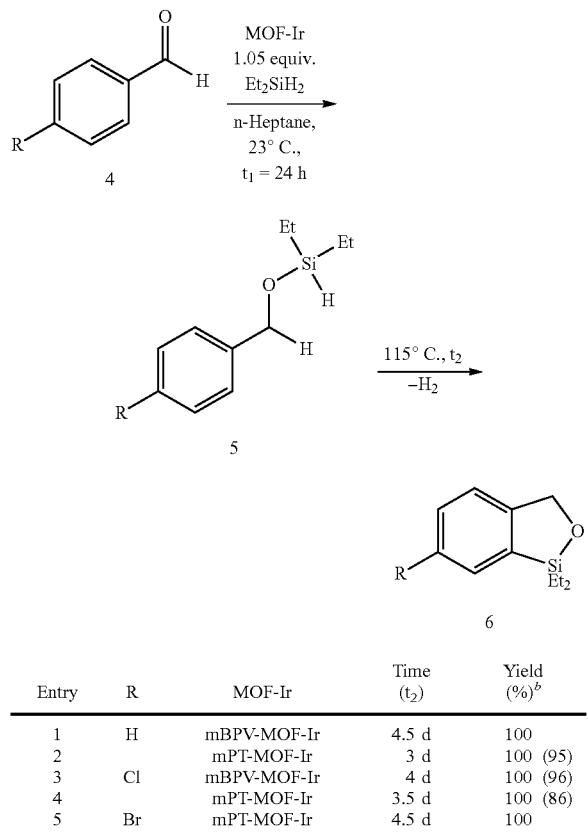

| Entry | R | MOF-Ir | Time (t$_2$) | Yield (%)[b] |
|---|---|---|---|---|
| 1 | H | mBPV-MOF-Ir | 4.5 d | 100 |
| 2 |   | mPT-MOF-Ir | 3 d | 100 (95) |
| 3 | Cl | mBPV-MOF-Ir | 4 d | 100 (96) |
| 4 |   | mPT-MOF-Ir | 3.5 d | 100 (86) |
| 5 | Br | mPT-MOF-Ir | 4.5 d | 100 |

[a]Reaction conditions: MOF-Ir (0.5 mol % Ir), 4.0 mL n-heptane, 115° C., reflux under N$_2$.
[b]Isolated yield in the parenthesis.

Figure 9:
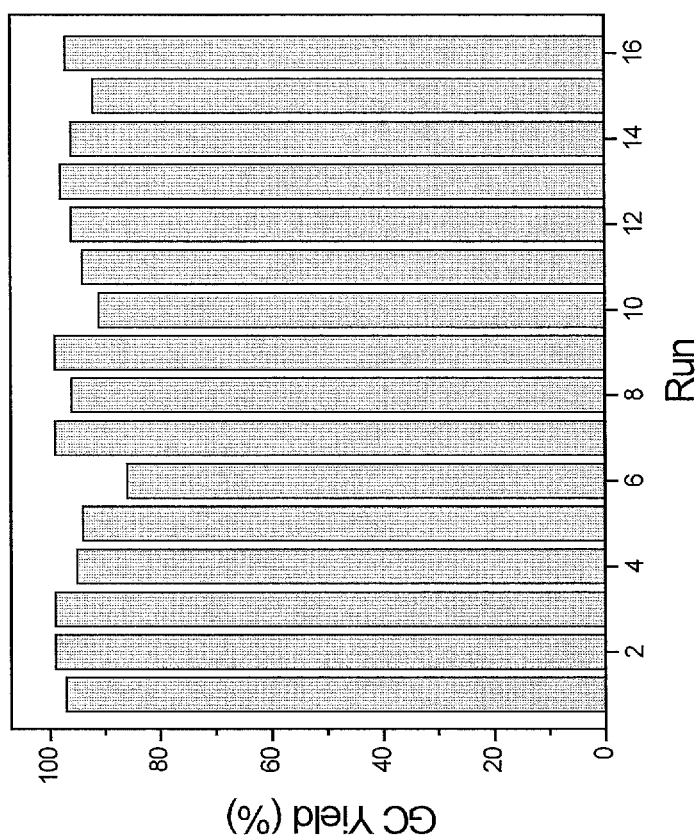
FIG. 9 is a plot of yield (%) of benzoxasilole at various runs in the recycle and reuse of mPT-MOF-Ir (0.5 mol % Ir) for ortho-silylation of 2 g in Example 11

Remarkably, at a 0.5 mol % Ir loading, mPT-MOF-Ir could be recovered and reused for the intramolecular ortho-silylation of 2g at least 15 times without loss of MOF crystallinity (FIG. 9). Excellent yields (86-99%) of the benzoxasilole, 3g, were obtained consistently in the reuse experiments. Importantly, 3g was obtained in high purity simply by removing the solid catalyst and the organic volatiles (without any other workup). The heterogeneous nature of mPT-MOF-Ir was further confirmed by several experiments. The PXRD patterns of mPT-MOF-Ir recovered from the 1$^{st}$ and 16$^{th}$ run remained essentially unchanged from that of freshly prepared mPT-MOF-Ir. Additionally, ICP-MS analyses showed that the amounts of Ir and Zr leaching into the supernatant after the 1st run were 2.1% and 0.008%, respectively, and the amounts of leached Ir and Zr after the 5$^{th}$ run were 0.08% and 0.009%, respectively. Moreover, no further conversion was detected after removal of mPT-MOF-Ir during the course of the silylation reaction. These results collectively indicate that the mPT-MOF-Ir catalyst is very stable under the catalytic conditions.

The high activity of mPT-MOF-Ir in hydroxyl-directed intramolecular silylation of arene C—H bonds inspired us to investigate the analogous silylation reactions directed by an amine group. The dehydrogenative intramolecular silylation of aromatic C—H bonds of (hydrido)silyl amines would generate azasilolanes. The silicon-heteroatom bonds in azasilolanes could be further functionalized via oxidation or halogenations. Recently, Hartwig and co-workers reported Ir-catalyzed secondary amine directed silylation of aromatic C—H bonds, in which (hydrido)silyl amines, generated in situ by [Ir(COD)(OMe)]$_2$-catalyzed dehydrocoupling of benzylamine with Et$_2$SiH$_2$, undergo dehydrogenative silylation in presence of norborene as the hydrogen acceptor by 3,4,7,8-tetramethyl-1,10-phenanthroline-derived iridium catalyst (Li, Q.; Driess, M.; Hartwig, J. F. *Angew. Chem. Int. Ed.* 2014, 53, 8471). Interestingly, mPT-MOF-Ir afforded azasilolanes directly from N-methylbenzyl amines and Et$_2$SiH$_2$ without employing any H-acceptor. Analogous to hydroxyl-directed silylation reactions, 0.5 mol % mPT-MOF-Ir provided (hydrido)silyl amines in n-heptane at room temperature in 24 h. Refluxing the resultant mixture at 115° C. afforded azasilolanes in complete conversions (Table 25). Azasilolanes 9a and 9b were obtained in 92% and 82% yields respectively (Table 25, entries 1 and 2). In contrast, 0.5 mol % of {pth}Ir(COD)(OMe) afforded 9a from 8a in only 20% conversion at 115° C. in n-heptane and no further conversion was observed upon refluxing for longer times. The similar PXRD pattern of recovered mPT-MOF-Ir to that of freshly prepared catalyst indicates that the MOF remained crystalline and stable under the reaction conditions.

TABLE 25 mPT-MOF-Ir Catalyzed Tandem Dehydrocoupling of N-Methylbenzyl Amines and Intramolecular ortho-Silylation of (Hydrido)silyl Amines to Azasilolanes[a]

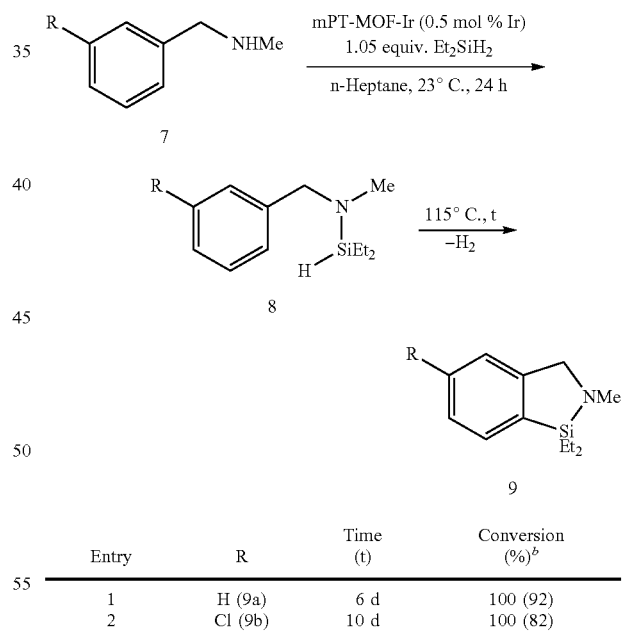

| Entry | R | Time (t) | Conversion (%)[b] |
|---|---|---|---|
| 1 | H (9a) | 6 d | 100 (92) |
| 2 | Cl (9b) | 10 d | 100 (82) |

[a]Reaction conditions: mPT-MOF-Ir (0.5 mol % Ir), 4.0 mL n-heptane, 115° C., reflux under N$_2$. [b]NMR yield in the parenthesis.

MOF-Ir catalysts are also active in dehydrogenative borylation of aromatic C—H bonds using B$_2$(pin)$_2$ (pin=pinacolate) as the borylating agent (Iverson, C. N.; Smith, M. R. *J. Am. Chem. Soc.* 1999, 121, 7696; Ishiyama, T.; Takagi, J.; Ishida, K.; Miyaura, N.; Anastasi, N. R.; Hartwig, J. F. *J. Am. Chem. Soc.* 2001, 124, 390; Cho, J.-Y.; Tse, M. K.; Holmes, D.; Maleczka, R. E.; Smith, M. R. *Science* 2002, 295, 305; Ishiyama, T.; Takagi, J.; Hartwig, J.

F.; Miyaura, N. *Angew. Chem. Int. Ed.* 2002, 41, 3056; Roosen, P. C.; Kallepalli, V. A.; Chattopadhyay, B.; Singleton, D. A.; Maleczka, R. E.; Smith, M. R. *J. Am. Chem. Soc.* 2012, 134, 11350. Mazzacano, T. J.; Mankad, N. P. *J. Am. Chem. Soc.* 2013, 135, 17258. (g) Preshlock, S. M.; Ghaffari, B.; Maligres, P. E.; Krska, S. W.; Maleczka, R. E.; Smith, M. R. *J. Am. Chem. Soc.* 2013, 135, 7572. (h) Obligacion, J. V.; Semproni, S. P.; Chink, P. J. *J. Am. Chem. Soc.* 2014, 136, 4133). Borylation of aryl C—H bonds provides aryl boronates, which are versatile reagents in organic synthesis (Miyaura, N.; Suzuki, A. *Chem. Rev.* 1995, 95, 2457; Hayashi, T.; Yamasaki, K. *Chem. Rev.* 2003, 103, 2829; Maleczka, R. E.; Shi, F.; Holmes, D.; Smith, M. R. *J. Am. Chem. Soc.* 2003, 125, 7792; Holmes, D.; Chotana, G. A.; Maleczka, R. E.; Smith, M. R. *Org. Lett.* 2006, 8, 1407; Kudo, N.; Perseghini, M.; Fu, G. C. *Angew. Chem. Int. Ed.* 2006, 45, 1282; Murphy, J. M.; Liao, X.; Hartwig, J. F. *J. Am. Chem. Soc.* 2007, 129, 15434; Tzschucke, C. C.; Murphy, J. M.; Hartwig, J. F. *Org. Lett.* 2007, 9, 761; Beck, E. M.; Hatley, R.; Gaunt, M. J. *Angew. Chem. Int. Ed.* 2008, 47, 3004; Wan, L.; Dastbaravardeh, N.; Li, G.; Yu, J.-Q. *J. Am. Chem. Soc.* 2013, 135, 18056) In homogeneous catalysis, a number of nitrogen and phosphine-based iridium(I) catalysts have been reported and generally bipyridyl-derived catalysts are more active compared to those containing phosphine ligands. Recently, efforts to develop heterogeneous borylation catalysts have been made based on iridium (0) nanoparticles (Yinghuai, Z.; Chenyan, K.; Peng, A. T.; Emi, A.; Monalisa, W.; Kui-Jin Louis, L.; Hosmane, N. S.; Maguire, J. A. *Inorg. Chem.* 2008, 47, 5756), insoluble iridium complex (Tagata, T.; Nishida, M.; Nishida, A. *Adv. Synth. Catal.* 2010, 352, 1662), or silica-supported catalyst (Kawamorita, S.; Ohmiya, H.; Hara, K.; Fukuoka, A.; Sawamura, M. *J. Am. Chem. Soc.* 2009, 131, 5058; Grüning, W. R.; Siddiqi, G.; Safonova, O. V.; Copéret, C. *Adv. Synth. Catal.* 2014, 356, 673; (c) Wu, F.; Feng, Y.; Jones, C. W. *ACS Catal.* 2014, 4, 1365). The MOF-Ir catalyzed borylation reactions were first screened for optimized conditions such as temperature, solvents, and in neat arenes (without using a solvent) to obtain the best results. The screening experiments revealed that the highest turnover frequencies were observed when the borylation reactions were performed in neat arene at 115° C. or refluxed in n-heptane at 115° C. for solid substrates. Longer reaction time was required when the reaction mixture was heated above 115° C., which is likely due to the instability of active catalytic species at higher temperatures. Under the optimized conditions, 0.1 mol % BPV-MOF-Ir gave 72% of 5-(4,4,5,5-Tetramethyl-1,3,2-dioxaborolan-2-yl)-m-xylene (11a) in 5 d from m-xylene and 100% of 2-(4,4,5,5-tetramethyl-1,3,2-dioxaborolan-2-yl)-1H-indole (11h) from indole in 16 h (Table 26, entries 1 and 15). In contrast, mBPV-MOF-Ir and mPT-MOF-Ir afforded 11a and 11h in quantitative yields at much shorter reaction times (Table 26; entries 2, 4, 16, and 18). mPT-MOF-Ir(COD)-Cl was about half as active in C—H borylation as mPT-MOF-Ir. The TPHN-MOF treated with [Ir(COD)(OMe)]$_2$ did not give any activity for benzene borylation, ruling out the involvement of the Zr$_6$($\mu_3$-O)$_4$($\mu_3$-OH)$_4$ SBUs in arene borylation reactions. The faster reaction rates due to the presence of more open channels within the mMOF-Ir catalysts led us to investigate the borylation reactions with a broad range of substrates. Mono-borylated arenes were obtained in excellent yields (94-100%) for a range of activated and unactivated arenes (Table 26). Halogen- and alkoxy-functional groups were well tolerated under the reaction conditions. The regioselectivities of borylated products are the same as those reported for homogeneous Ir-catalysts (Manna, K.; Zhang, T.; Lin, W. *J. Am. Chem. Soc.* 2014, 136, 6566; Ishiyama, T.; Takagi, J.; Hartwig, J. F.; Miyaura, N. *Angew. Chem. Int. Ed.* 2002, 41, 3056). The borylation occurred at the least sterically hindered C—H bonds of the unactivated arenes (Table 26, entries 1-14) and at the 2-position of heteroarenes such as indole and benzo[b]furan (Table 26, entries 15-20). Notably, pure products were obtained by simply removing the catalyst via centrifugation followed by removal of the volatiles. Although both mMOFs afforded borylated arenes in excellent yields, mBPV-MOF-Ir displayed superior activity over mPT-MOF-Ir. Importantly, TONs of 17000 and 9000 were obtained for borylation of m-xylene and indole, respectively, with mBPV-MOF-Ir (Table 23; entries 3 and 17). In these two cases, the leached iridium contents in 5-(4,4,5,5-tetramethyl-1,3,2-dioxaborolan-2-yl)-m-xylene (11a, 1.50 g, 6.46 mmol) and 2-(4,4,5,5-tetramethyl-1,3,2-dioxaborolan-2-yl)-1H-indole (11h, 0.765 g, 3.15 mmol) were 1.22 ppm and 0.3 ppm, respectively. Therefore, pure borylated products containing very low residual iridium in 1 ppm or lower levels could be obtained without any chromatographic purification.

Figure 10B:
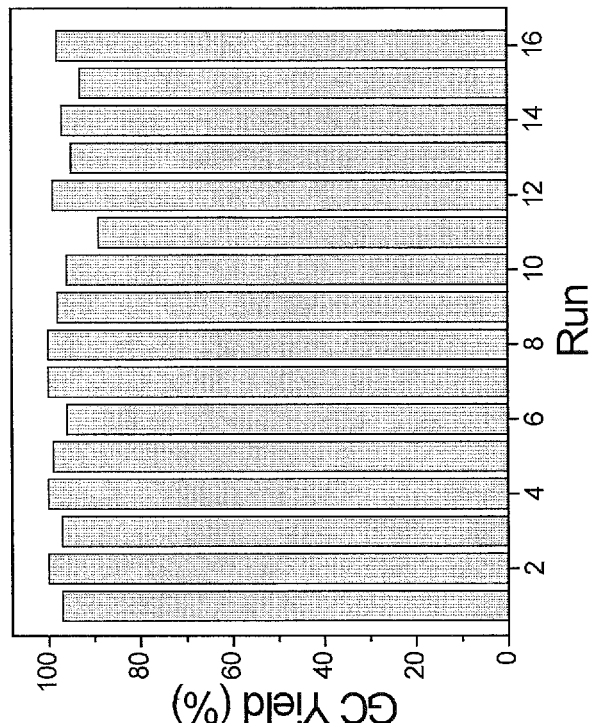
FIG. 10B shows plots from Example 11 of GC conversion (%) for various runs in the recycle and reuse of mBPV-MOF-Ir for borylation of indole.
Figure 10A:
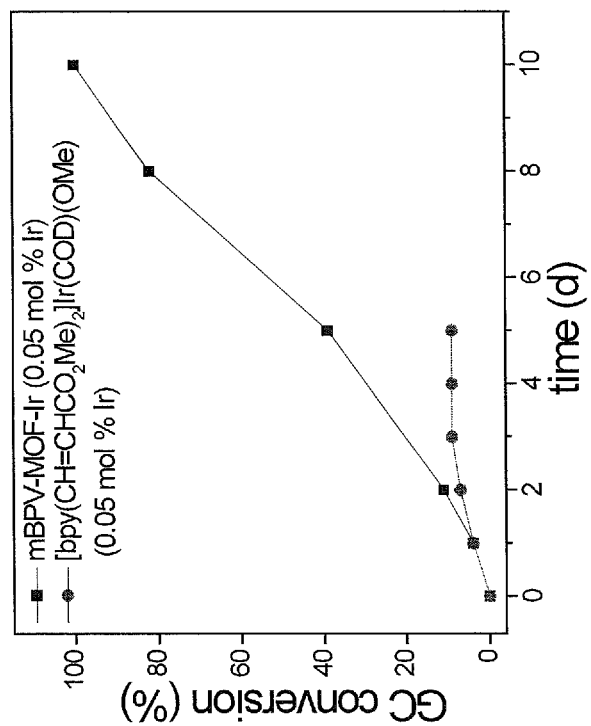
FIG. 10A shows plots from Example 11 of GC conversion (%) vs time (h) for C—H borylation of m-xylene using mBPV-MOF-Ir (0.01 mol %) (squares) and [bpy(CH=CHCO$_2$Me)$_2$]Ir(COD)(OMe) (0.05 mol %) (diamonds) as catalysts under identical conditions.
Figure 10C:
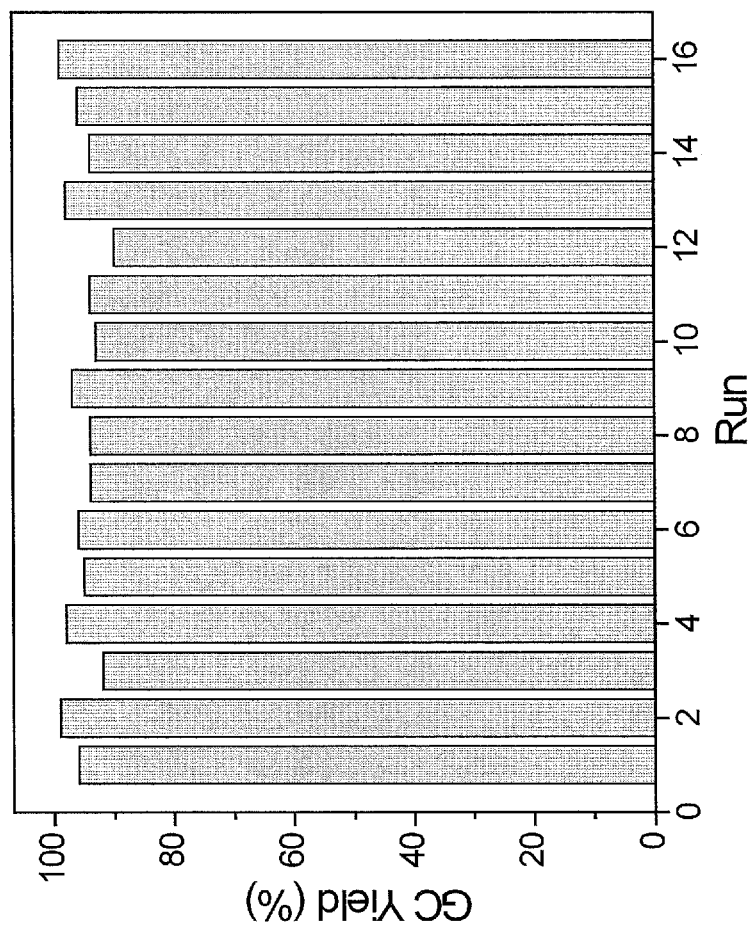
FIG. 10C show plots from Example 11 of GC conversion (%) for various runs in the recycle and reuse of mPT-MOF-Ir for borylation of m-xylene.

Interestingly, both mMOFs catalysts are significantly more active in C—H borylation of arenes than their homogeneous counterparts. Time dependent GC conversion curves indicated that mBPV-MOF-Ir was also at least 95 times more active than its homogeneous control [bpy(CH═CHCO$_2$Me)$_2$]Ir(COD)(OMe) (FIG. 10A). [bpy(CH═CHCO$_2$Me)$_2$]Ir(COD)(OMe) had a very low activity in borylation reaction. At 115° C. in neat m-xylene, 0.05 mol % [bpy(CH═CHCO$_2$Me)$_2$]Ir(COD)(OMe) afforded 8a in only 9% conversion after 2 days, and then no further conversion was observed with prolonged heating. However, under identical conditions, mBPV-MOF-Ir gave 11a with a TON of 17000.

mPT-MOF-Ir also compares favorably to its homogeneous counterpart, with at least twice as high activity as its homogeneous control. Therefore, immobilization of molecular catalysts in the MOF framework dramatically enhances the overall activity and stability of the catalysts by preventing bimolecular deactivation pathways. Remarkably, at a 0.5 mol % Ir loading, the MOF-Ir catalyst was reused more than 15 times in the borylation of indole without loss of catalytic activity (FIG. 10B) or MOF crystallinity. Excellent yields (89-100%) of 2-(4,4,5,5-tetramethyl-1,3,2-dioxaborolan-2-yl)-1H-indole (11h) were obtained consistently in the reuse experiments. Notably, 11h was obtained in high purity simply by removing the solid catalyst and the organic volatiles. The heterogeneity of mBPV-MOF-Ir was confirmed by several experiments. The PXRD patterns of mBPV-MOF-Ir recovered from the 1$^{st}$ and 16$^{th}$ run remained the same as that of freshly prepared mBPV-MOF-Ir, indicating that the MOF catalyst is very stable under the catalytic conditions. The leaching of Ir and Zr into the supernatant was very low during the course of the borylation reaction as shown by ICP-MS analysis. The amounts of Ir and Zr leaching into the supernatant after the 1st run were 0.132% and 0.029%, respectively, and after the 5$^{th}$ run were 0.016% and 0.012%, respectively. Moreover, no further conversion was detected after removal of mBPV-MOF-Ir from the reaction mixture. mPT-MOF-Ir could also be recycled 15 times for borylation of m-xylene (FIG. 10C). The PXRD of recovered mPT-MOF-Ir after run 17 indicated that the MOF remained crystalline, which suggests that the deactivation of mPT-MOF-Ir at run 17 is due to the decomposition of the active Ir-catalyst but not the MOF framework. Additionally, ICP-MS analyses showed that the amounts of Ir and Zr leaching into the supernatant were 0.042% and 0.038% respectively after the 1$^{st}$ run, 0.08% and 0.009% respectively after the 5$^{th}$ run, and 0.018% and 0.014% respectively after the 10$^{th}$ run.

TABLE 26

MOF-Ir catalyzed C—H borylation of arenes.[a]

$$2 \ Ar-H + \underset{10}{B_2pin_2} \xrightarrow[115°\ C.]{MOF-Ir} 2 \ Ar-Bpin + H_2$$
$$11$$

| Entry | Substrate | Product | MOF-Ir catalyst | Ir loading (mol %) | Time | Yield (%)[b] |
|---|---|---|---|---|---|---|
| 1[c] | 1,3-dimethylbenzene | 3,5-dimethylphenyl-Bpin | BPV-MOF-Ir | 0.1 | 5 d | 72 |
| 2[c] | | | mBPV-MOF-Ir | 0.1 | 16 h | 100 (97) |
| 3[c] | | | mBPV-MOF-Ir | 0.005 | 15 d | 85 |
| 4[c] | | | mPT-MOF-Ir | 0.1 | 32 h | 100 (96) |
| 5[c] | 1,2-dimethylbenzene | 3,4-dimethylphenyl-Bpin | mBPV-MOF-Ir | 0.1 | 16 h | 100 (97) |
| 6[c] | | | mPT-MOF-Ir | 0.1 | 35 h | 100 (99) |
| 7[c] | benzene | phenyl-Bpin | mBPV-MOF-Ir | 0.1 | 16 h | 100 |
| 8[c] | | | mPT-MOF-Ir | 0.1 | 18 h | 100 |
| 9[c] | toluene | tolyl-Bpin | mPT-MOF-Ir | 0.1 | 18 h | 100 (o:m:p = 0:62:38) |
| 10[c] | 1,2-dichlorobenzene | 3,4-dichlorophenyl-Bpin | mBPV-MOF-Ir | 0.1 | 24 h | 100 (94) |
| 11[c] | | | mPT-MOF-Ir | 0.1 | 30 h | 100 (95) |
| 12 | 1,4-dichlorobenzene | 2,5-dichlorophenyl-Bpin | mPT-MOF-Ir | 1.0 | 24 h | 100 |
| 13 | 1,2-dimethoxybenzene | 3,4-dimethoxyphenyl-Bpin | mBPV-MOF-Ir | 0.1 | 36 h | 100 (96) |
| 14 | | | mPT-MOF-Ir | 0.1 | 2 d | 100 |
| 15 | indole | 2-Bpin-indole | BPV-MOF-Ir | 0.1 | 18 h | 100 |
| 16 | | | mBPV-MOF-Ir | 0.1 | 5 h | 100 (98) |
| 17 | | | mBPV-MOF-Ir | 0.01 | 9 d | 90 |
| 18 | | | mPT-MOF-Ir | 0.1 | 11 h | 100 (94) |
| 19 | benzofuran | 2-Bpin-benzofuran | mPT-MOF-Ir | 0.5 | 18 h | 100 |

[a]Reaction conditions: MOF-Ir, 0.508 mmol B₂pin₂, 1.02 mmol of arene, 3.0 mL of n-heptane, 115° C., reflux under N₂. [b]Isolated yield in the parenthesis. [c]Neat arene was used.

1. General Experimental

All of the solvents were purchased from Fisher and used without further purification. All of the reactions and manipulations were carried out under nitrogen with the use of standard inert atmosphere and Schlenk techniques unless otherwise indicated. 5,5'-Dibromo-2,2'-bipyridine was prepared according to published procedures (Bruce, J. I.; Chambron, J.-C.; Kolle, P.; Sauvage, J.-P. *J. Chem. Soc Perkin Trans.* 1 2002, (10), 1226-1231; Schwab, P. F. H.; Fleischer, F.; Michl, J., *J. Org. Chem.* 2002, 67 (2), 443-449). [Ir(COD)(OMe)]$_2$ was purchased from Aldrich, and Et$_2$SiH$_2$ was purchased from Alfa Aesar. All of the other substrates and reagents are commercially available and used as received unless otherwise indicated. Actophenone, 4-chloroactophenone, 1-phenylbutan-1-one, 1-phenylpropan-1-ol, 1,2-dimethoxybenzene, 1-(4-methylphenyl)ethanone, benzaldehyde, o-xylene, m-xylene, and 1,2-dichlorobenzene were dried with freshly activated 4 Å molecular sieves in a glovebox prior to use. $^1$H NMR spectra were recorded on a Bruker NMR 400 DRX spectrometer at 400 MHz and referenced to the proton resonance resulting from incomplete deuteration of the deuterated chloroform (δ 7.26). Thermogravimetric analysis (TGA) was performed in air using a Shimadzu TGA-50 equipped with a platinum pan. Powder X-ray diffraction (PXRD) patterns were collected on a Bruker D8 Venture, dual microsource (Cu and Mo) diffractometer with a CMOS detector. Cu Kα radiation was used. The PXRD patterns were processed with the APEX 2 package using PILOT plug-in. Conversions of reactions were determined by gas chromatography (GC) using a Shimadzu GC-2010 gas chromatograph equipped with a flame ionization detector (FID). ICP-MS data were obtained with an Agilent 7700x ICP-MS and analyzed using ICP-MS MassHunter version B01.03. Samples were diluted in a 2% HNO$_3$ matrix and analyzed with a $^{159}$Tb internal standard against a six-point standard curve over the range from 0.1 ppb to 1000 ppb. The correlation coefficient was >0.9997 for all analytes of interest. Data collection was performed in Spectrum Mode with five replicates per sample and 100 sweeps per replicate.

2. Synthesis of 5,5'-bis(carboxyethenyl)-2,2'-bipyridine (H$_2$BPV) and 3,8-bis(4-carboxyphenyl)phenanthroline (H$_2$PT)

Synthesis of 5,5'-bis(carboxyethenyl)-2,2'-bipyridine (H$_2$BPV)

a) 5,5'-bis(methoxycarbonylethenyl)-2,2'-bipyridine 5,5'-dibromo-2,2'-bipyridine (646 mg, 2.0 mmol) was dissolved in a mixture of 10 mL of DMF and 10 mL of triethylamine and degassed. Palladium acetate (19 mg), tris(o-tolyl)phosphine (84 mg), and methyl acrylate (2.5 mL, 27.6 mmol) were then added to the solution. The solution was sealed in a pressure vessel under nitrogen and heated to 120° C. for 2 days. After cooling to r.t., the solution was concentrated to afford a yellow solid as the crude product, which was purified through Soxhlet extraction to afford the pure 5,5'-bis(methoxycarbonylethenyl)-2,2'-bipyridine as a light yellow solid (428 mg, 66%). $^1$H NMR (500 MHz, CDCl$_3$) δ 8.83 (s, 2H), 8.51 (d, 2H, $^3J_{HH}$=8.2 Hz), 8.01 (dd, 2H, $^3J_{HH}$=8.2 Hz, $^4J_{HH}$=2.0 Hz), 7.77 (d, 2H, $^3J_{HH}$=16.0 Hz), 6.61 (d, 2H, $^3J_{HH}$=16.0 Hz), 3.87 (s, 6H).

b) 5,5'-bis(carboxyethenyl)-2,2'-bipyridine 5,5'-bis(methoxycarbonylethenyl)-2,2'-bipyridine (428 mg, 1.3 mmol) was dissolved in a mixture of equal volume of 6 M NaOH (aq) and ethanol and refluxed overnight. After cooling down, the solution was acidified with 2 M HCl, centrifuged, solid washed with water and dried under vacuum to afford 5,5'-bis(carboxyethenyl)-2,2'-bipyridine as a white solid (350 mg, 91%). $^1$H NMR (500 MHz, DMSO-d$_6$) δ 12.64 (br s, 2H), 9.00 (s, 2H), 8.44 (d, 2H, $^3J_{HH}$=8.5 Hz), 8.33 (dd, 2H, $^3J_{HH}$=8.5 Hz, $^4J_{HH}$=2.0 Hz), 7.71 (d, 2H, $^3J_{HH}$=16.0 Hz), 6.78 (d, 2H, $^3J_{HH}$=16.0 Hz). $^{13}$C NMR (125.8 MHz, DMSO-d$_6$) δ 167.71, 150.32, 140.62, 136.28, 122.21, 121.15. ESI-MS: m/z [M+H]$^+$=297.1 (calcd. 297.09).

Synthesis of 3,8-bis(4-carboxyphenyl)phenanthroline (H$_2$PT)

a) 3,8-dibromophenanthroline (Karnahl, M.; Krieck, S.; Görls, H.; Tschierlei, S.; Schmitt, M.; Popp, J.; Chartrand, D.; Hanan, G. S.; Groarke, R.; Vos, J. G.; Rau, S., *Eur. J. Inorg. Chem.* 2009, 2009 (33), 4962-4971; Saitoh, Y.; Koizumi, T.-a.; Osakada, K.; Yamamoto, T., *Can. J. Chem.* 1997, 75 (10), 1336-1339)

Phenanthroline monohydrate (497 mg, 2.76 mmol) was dissolved in 20 mL of n-butyl chloride and degassed. Pyridine (0.72 mL, 9.0 mmol, 3.3 equiv.), S$_2$Cl$_2$ (0.75 mL, 9.4 mmol, 3.4 equiv.) and bromine (0.3 mL, 5.8 mmol, 2.1 equiv.) were then added sequentially to the solution. The resulting mixture was then heated to reflux for 12 h under nitrogen and cooled to room temperature. The supernatant was decanted, and the solid was suspended in a mixture of equal volume of 2 M NaOH (aq) and CHCl$_3$. The aqueous layer was separated and extracted with CHCl$_3$ once more. The organic layers were then combined, dried over Na$_2$SO$_4$ and concentrated to give the crude product. The crude product was purified via column chromatography (neutral alumina, CHCl$_3$:hexane=2:3 V/V) to give a white-to-light-yellow solid as the pure 3,8-dibromophenanthroline (332 mg, 37%). $^1$H NMR (500 MHz, CDCl$_3$) δ 9.21 (d, 2H, $^4J_{HH}$=2.2 Hz), 8.44 (d, 2H, $^4J_{HH}$=2.2 Hz), 7.79 (s, 2H).

b) 3,8-bis(4-methoxycarbonylphenyl)phenanthroline 3,8-dibromophenanthroline (580 mg, 1.7 mmol) and 4-methoxycarbonylphenylboronic acid (805 mg, 4.5 mmol) were suspended in 30 mL of 1,2-dimethoxyethane and degassed. Tetrakis(triphenylphosphine) palladium(0) (177 mg) and cesium fluoride (1.103 g) were then added. The resulting mixture was sealed in a pressure vessel under nitrogen and heated to 110° C. for 4 days. After cooling to r.t., the solid was filtered and subject to Soxhlet extraction with chloroform for 3 days. The extraction was concentrated, solid collected and washed with chloroform and tetrahydrofuran to afford 3,8-bis(4-methoxycarbonylphenyl)phenanthroline as a white solid (587 mg, 77%). $^1$H NMR (500 MHz, CDCl$_3$) δ 9.50 (s, 2H), 8.50 (s, 2H), 8.25 (d, 4H, $^3J_{HH}$=8.0 Hz), 7.96 (s, 2H), 7.90 (d, 4H, 8.0 Hz), 4.00 (s, 6H).

c) 3,8-bis(4-carboxyphenyl)phenanthroline 3,8-bis(4-methoxycarbonylphenyl)phenanthroline (580 mg, 1.3 mmol) was dissolved in a mixture of equal volume of 6 M NaOH (aq) and ethanol and refluxed overnight. After cooling to r.t., the solution was acidified with 2 M HCl and centrifuged. The solid was washed with water and dried under vacuum to afford 3,8-bis(4-carboxyphenyl)phenanthroline as a white solid (420 mg, 77%). $^1$H NMR (500 MHz, DMSO-d$_6$) δ 13.19 (br s, 2H), 9.54 (s, 2H), 9.01 (s, 2H), 8.19 (s, 2H), 8.16 (s, 8H). $^{13}$C NMR (125.8 MHz, DMSO-d$_6$) δ 167.51, 131.09, 130.68, 128.09, 128.01. ESI-MS: m/z [M+H]$^+$=421.1 (calcd. 421.12).

3. Synthesis and Characterization of BPV-MOF, mBPV-MOF and mPT-MOF

Synthesis of BPV-MOF.

ZrCl$_4$ (10 mg) and H$_2$BPV (10 mg) were dissolved in 5 mL of DMF and 0.08 mL of trifluoroacetic acid was added. The solution was then heated to 100° C. for 5 days to afford a white to pale yellow solid as the MOF product (yield 10 mg, 40%). After preparing a TGA curve of freshly prepared BPV-MOF in THF, a solvent weight loss of 55% was observed in the room temperature to 200° C. range. After performing a nitrogen sorption isotherm of BPV-MOF (77 K), it was observed that BPV-MOF has the BET surface area of 373 m$^2$/g. The low surface area of BPV-MOF is likely due to the partial collapse of the MOF framework upon removal of the solvents.

Synthesis of mBPV-MOF.

ZrCl$_4$ (15 mg), H$_2$BPV (5 mg), and 4,4'-bis(carboxyethenyl)-1,1'-biphenyl (10 mg) were dissolved in 4.5 mL of DMF and 0.08 mL of trifluoroacetic acid was added. The solution was then heated to 100° C. for 5 days to afford a white to pale yellow solid as the MOF product (yield 13 mg, 40%).

Analysis of Digested mBPV-MOF by NMR.

To determine the ratio of the two ligands, 10 mg of mBPV-MOF was first washed with THF and dried under vacuum. The resulting solid was then digested in a 1:1 mixture of saturated K$_3$PO$_4$/D$_2$O solution and DMSO-d$_6$ and shaken for 5 minutes. The organic layer was then analyzed by $^1$H NMR and the ligand ratio was determined by comparing the peaks corresponding to each ligand. After preparing a TGA curve of freshly prepared mBPV-MOF, a solvent weight loss of 64% was observed in the room temperature to 200° C. range. After performing a nitrogen sorption isotherm of mBPV-MOF (77 K), it was observed that mBPV-MOF has the BET surface area of 1207 m$^2$/g.

Synthesis of mPT-MOF.

ZrCl$_4$ (10 mg), H$_2$PT (6 mg) and 4,4'-bis(carboxyphenyl)-2-nitro-1,1'-biphenyl (14 mg) were dissolved in 5 mL of DMF and 0.05 mL of trifluoroacetic acid was added. The solution was then heated to 100° C. for 5 days to afford a pale yellow solid as the MOF product (yield 17 mg, 45%).

Analysis of Digested mPT-MOF by NMR.

To determine the ratio of the two ligands, 10 mg of mPT-MOF was first washed with THF and dried under vacuum. The resulting solid was then digested in a 1:1 mixture of saturated K$_3$PO$_4$/D$_2$O solution and DMSO-d$_6$ and shaken for 5 minutes. The organic layer was then analyzed by $^1$H NMR and the ligand ratio was determined by comparing the peaks corresponding to each ligand. After preparing a TGA curve of freshly prepared mPT-MOF, a solvent weight loss of 60% was observed in the room temperature to 200° C. range. After performing nitrogen sorption isotherms of mPT-MOF (77 K), mPT-MOF has a BET surface area of 3834 m$^2$/g.

4. Synthesis and Characterization of BPV-MOF-Ir, mBPV-MOF-Ir, and mPT-MOF-Ir Synthesis of BPV-MOF-Ir.

In a glovebox, BPV-MOF (30.0 mg) in THF was weighed onto a filter paper and then charged into a vial. [Ir(COD)(OMe)]$_2$ (10 mg, 15.1 μmol) dissolved in 2.0 mL of THF was added to the vial and the mixture was kept in the glovebox for 18 h. The resultant deep purple solid was centrifuged out of suspension and washed with THF 4-5 times. The resulting BPV-MOF-Ir was stored in heptane in the glovebox. BPV-MOF-Ir has 30% solvent weight based on TGA analysis and 65% Ir-loading with respect to Zr centers (i.e. total bridging ligands) based on ICP-MS analysis. After preparing TGA curves of freshly prepared BPV-MOF and BPV-MOF-Ir in the 25-600° C. range and 200-600° C. range, an increased residual mass at 600° C. due to the presence of Ir in BPV-MOF-Ir was observed. After performing nitrogen sorption isotherms of BPV-MOF and BPV-MOF-Ir, it was observed that BPV-MOF-Ir has a BET surface area of 106 m$^2$/g.

Synthesis of mBPV-MOF-Ir.

In a glovebox, mBPV-MOF (50.0 mg) in THF was weighed onto a filter paper and then charged into a vial. [Ir(COD)(OMe)]$_2$ (6.0 mg, 9.05 μmol) dissolved in 2.0 mL of THF was added to the vial and the mixture was kept in the glovebox for 18 h. The resultant deep purple solid was centrifuged out of suspension and washed with THF 4-5 times. The resulting mBPV-MOF-Ir was stored in heptane in the glovebox. mBPV-MOF-Ir has 55% solvent weight based on TGA analysis and 16% Ir-loading with respect to Zr centers (i.e. total bridging ligands) based on ICP-MS analysis. After preparing TGA curves of freshly prepared mBPV-MOF and mBPV-MOF-Ir in the 25-600° C. range and 200-600° C. range, an increased residual mass at 600° C. due to the presence of Ir in mBPV-MOF-Ir was observed. After performing nitrogen sorption isotherms of mBPV-MOF (77 K) and mBPV-MOF-Ir (77 K), it was observed that mBPV-MOF-Ir has a BET surface area of 563 m$^2$/g. The low surface areas of both mBPV-MOF and mBPV-MOF-Ir are due to the partial collapse of frameworks upon removal of the solvents. Pore size distributions of mBPV-MOF and mBPV-MOF-Ir were also determined.

Synthesis of mPT-MOF-Ir.

In a glovebox, mPT-MOF (30.0 mg) in THF was weighed onto a filter paper and then charged into a vial. [Ir(COD)(OMe)]$_2$ (4.0 mg, 6.03 μmol) dissolved in 1.0 mL of THF was added to the vial and the mixture was kept in the glovebox for 15 h. The resultant deep green solid was centrifuged out of suspension and washed with THF 4-5 times. The resulting mPT-MOF-Ir was stored in heptane in the glovebox. mPT-MOF-Ir has 38% solvent weight based on TGA analysis and 20% Ir-loading with respect to Zr centers (i.e. total bridging ligands) based on ICP-MS analysis. After preparing TGA curves of freshly prepared mPT-MOF and mPT-MOF-Ir in the 200-600° C. range, an increased residual mass at 600° C. due to the presence of Ir in mPT-MOF-Ir was observed. After performing nitrogen sorption isotherms of mPT-MOF-Ir (77 K), it was observed that mPT-MOF-Ir has a BET surface area of 1827.9 m$^2$/g. Pore size distributions of mPT-MOF and mPT-MOF-Ir were also determined.

Synthesis of mPT-MOF-Ir(COD)-Cl.

In a glovebox, mPT-MOF (13.0 mg) in THF was charged into a vial. [IrCl(COD)]$_2$ (2.5 mg, 3.72 μmol) dissolved in 1.0 mL of THF was added to the vial and the mixture was kept in the glovebox for 24 h. The resultant green solid was centrifuged out of suspension and washed with THF 4-5 times. mPT-MOF-Ir has 12% Ir-loading with respect to Zr centers (i.e. total bridging ligands) based on ICP-MS analysis.

Synthesis of (Me$_2$BPV)Ir(COD)(OMe).

In a glovebox, a vial was charged with Me$_2$BPV (27 mg, 0.083 mmol), [Ir(COD)(OMe)]$_2$ (27.5 mg, 0.041 mmol), and 10 mL THF. The resultant mixture was stirred at room temperature for 18 h. Removal of all the volatiles in vacuo afforded (Me2BPV)Ir(COD)(OMe) as a purple solid (52.0 mg, 0.079 mmol, 95.2%). $^1$H NMR (400 MHz, DMSO-d$_6$) δ 8.03 (s, 2H), 7.79 (d, 2H d, $^3J_{HH}$=8.0 Hz), 7.67 (d, 2H, $^3J_{HH}$=8.0 Hz), 7.51 (d, 2H, $^3J_{HH}$=16.0 Hz), 6.89 (d, 2H, $^3J_{HH}$=16.0 Hz), 4.12 (m, 4H), 3.72 (s, 3H), 3.16 (s, 6H), 2.18 (m, 4H), 1.74 (m, 4H). ESI-MS m/z 639.2 [(Me$_2$BPV)IrO(COD)]$^+$ (calcd 639.16).

Synthesis of (H$_2$BPV)Ir(COD)(OMe).

In a glovebox, a vial was charged with H$_2$BPV (7.0 mg, 0.024 mmol), [Ir(COD)(OMe)]$_2$ (7.8 mg, 0.012 mmol) and 5 mL DMSO. The resultant mixture was stirred at room temperature for 3 h. Removal of the volatiles in vacuo afforded (H$_2$BPV)Ir(COD)(OMe) as a deep green solid. $^1$H NMR (400 MHz, DMSO-d$_6$) δ 12.73 (br s, 2H), 8.75 (m, 4H), 8.61 (s, 2H), 7.86-7.82 (d, 2H, $^3J_{HH}$=16.0 Hz), 6.93-6.89 (d, 2H, $^3J_{HH}$=16.0 Hz), 3.98-3.36 (m, 7H), 2.31-2.18 (m, 4H), 1.75-1.56 (m, 4H). ESI-MS m/z 611.2 [(HBPV)Ir(COD)(OH)]$^+$ (calcd 611.13), 625.2 [(HBPV)Ir(COD)(OMe)]$^+$ (calcd 625.14).

5. Crystallographic Data of BPHV-MOF and TPHN-MOF

Single crystal X-ray diffraction data of BPHV-MOF and TPHN-MOF were collected with a Bruker APEX II CCD-based detector at ChemMatCARS (Sector 15), Advanced Photon Source (APS), Argonne National Laboratory. The frames were integrated with the Bruker SAINT© built-in APEX II software package using a narrow-frame integration algorithm, which also corrects for the Lorentz and polarization effects. Absorption corrections were applied using SADABS. Structures were solved by direct methods and refined to convergence by least squares method on F$^2$ using the SHELXTL-2013 software suite (Sheldrick, G., A short history of SHELX. *Acta Crystallogr. Sect. A* 2008, 64 (1), 112-122).

Due to the relatively weak diffraction and low resolution, which is not uncommon for this kind of framework with very large solvent accessible void space, restraints (SIMU and DELU) on displacement parameters, and DFIX for bond lengths are applied. All benzene rings are constrained to ideal geometry. Non-hydrogen atoms are refined isotropically. SQUEEZE subroutine of the PLATON software suite was applied to remove the scattering from the highly disordered guest molecules. The resulting new HKL4 files were used to further refine the structure.

TABLE 27

Crystallographic Data of BPHV-MOF and TPHN-MOF

| | Name | |
|---|---|---|
| | BPHV-MOF | TPHN-MOF |
| Formula | Zr$_6$(O)$_4$(OH)$_4$(C$_{18}$H$_{12}$O$_4$)$_6$ | Zr$_6$(O)$_4$(OH)$_4$(C$_{26}$H$_{16}$O$_4$)$_6$ |
| Fw | 2433.0 | 2932.88 |
| Temperature | 100 | 100 |
| Wavelength (Å) | 0.41328 | 0.41328 |
| Crystal system | Tetragonal | cubic |
| Space group | I$\bar{4}$ | Fm$\bar{3}$m |
| a, Å | 23.239 (4) | 38.678 (3) |
| b, Å | 23.239 (4) | 38.678 (3) |
| c, Å | 32.854 (13) | 38.678 (3) |
| α ° | 90 | 90 |
| β ° | 90 | 90 |
| γ ° | 90 | 90 |
| V, Å$^3$ | 17743 (9) | 57862 (8) |
| Z | 2 | 4 |
| Density (calcd. g/cm$^3$) | 0.455 | 0.337 |
| Absorption coeff. (mm$^{-1}$) | 0.265 | 0.154 |
| F(000) | 2440 | 5728 |
| θ range data collection | 0.624-10.874 | 0.87-10.15 |
| Limiting indices | −21 <= h <= 21, −17 <= k <= 20, −29 <= l <= 29 | −32 <= h <= 32, −32 <= k <= 32, −32 <= l <= 32 |
| Reflection collected | 21903 | 67300 |
| Independent reflections | 7004 | 998 |
| R(int) | 0.0653 | 0.1469 |
| Data/restraints/parameters | 7004/43/135 | 998/34/41 |
| Goodness-of-fit on F$^2$ | 1.153 | 2.243 |
| Final R indices [I > 2σ(I)] | R1 = 0.0739, wR2 = 0.1802 | R1 = 0.1126, wR2 = 0.2766 |
| R indices (all data) | R1 = 0.0975, wR2 = 0.1904 | R1 = 0.1178, wR2 = 0.2798 |

6. Catalytic Reactions with BPV-MOF-Ir, mBPV-MOF-Ir, and mPT-MOF-Ir

General procedure for MOF-Ir Catalyzed Tandem Hydrosilylation/Ortho-Silylation of Arenes.

In a glovebox, MOF-Ir (5.0 mg, 0.1 mol % Ir), aryl ketone (1.02 mmol) and Et$_2$SiH$_2$ (138.1 μL, 1.07 mmol) in 4.0 mL solvent were charged into a Schlenk tube containing a magnetic stir bar. The tube was kept in the glovebox for 18-48 h until GC analysis indicated complete conversion of the starting materials to benzylicsilyl ethers. The tube was then heated to reflux under nitrogen with slow stirring and the progress of the reaction was monitored by GC. After complete conversion, the reaction mixture was cooled to room temperature. The solid was centrifuged out of suspension and extracted with solvent for 2-3 times. The combined organic extracts were passed through a short plug of celite and concentrated in vacuo to yield the pure product.

TABLE 28

Optimization of reaction conditions for catalytic ortho-silylation of arene[a]

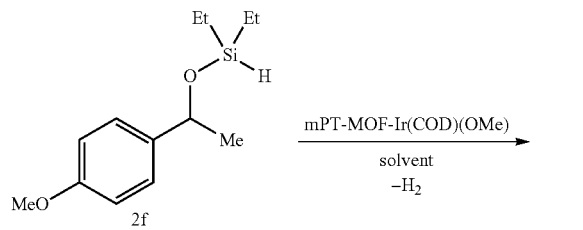 [SMILES: CC[SiH](CC)OC(C)c1ccc(OC)cc1]

| Entry | Ir loading (mol %) | Solvent | Temperature (° C.) | Time | Conversion (%)[b] |
|---|---|---|---|---|---|
| 1 | 1.0 | n-heptane | 115 | 15 h | 100 |
| 2 | 1.0 | n-octane | 122 | 19 h | 85 |
| 3 | 1.0 | n-octane | 130 | 10 h | 94 |
| 3 | 1.0 | m-xylene | 120 | 22 h | 60 |
| 4 | 0.1 | n-heptane | 115 | 4.5 d | 95 |

[a]Reaction conditions: 5 mg mixPT-MOF-Ir, 3.0 ml solvent. [b]% Conversion was determined by GC analysis.

A Typical Procedure for mPT-MOF-Ir Catalyzed Tandem Hydrosilylation/Ortho-Silylation of Arenes.

In a glovebox, mPT-MOF-Ir (5.0 mg, 0.1 mol % Ir), p-methoxyacetophenone (1f, 0.152 g, 1.01 mmol) and Et$_2$SiH$_2$ (138.2 μL, 1.06 mmol) in 4.0 mL n-heptane were charged into a Schlenk tube. The tube was left in the glovebox for 18 h. Then, the tube was heated to reflux at 115° C. under nitrogen for 4.5 d. The reaction mixture was cooled to room temperature and the solid was centrifuged out of suspension in the glovebox. The solid was extracted with n-heptane 2-3 times and could be reused. The combined organic extracts were passed through a short plug of celite and then concentrated in vacuo to yield pure benzoxasilole (3f, 0.213 g, 0.899 mmol, 89.0%) as a colorless oil.

Test of "Heterogeneity" of mPT-MOF-Ir

Scheme 32. The ortho-silylation of diethyl(hydrido)silyl ether (2g) stopped after removing mPT—MOF—Ir from the reaction mixture, demonstrating the "heterogeneous" nature of MOF catalysis.

a)
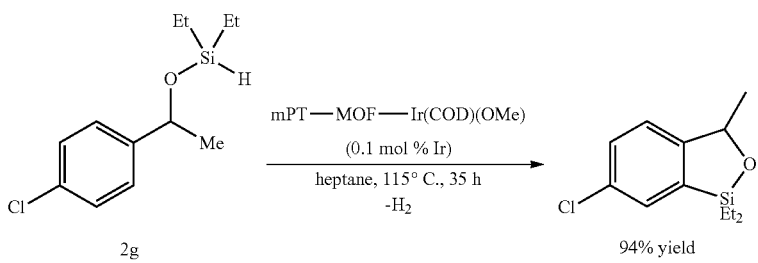

b)
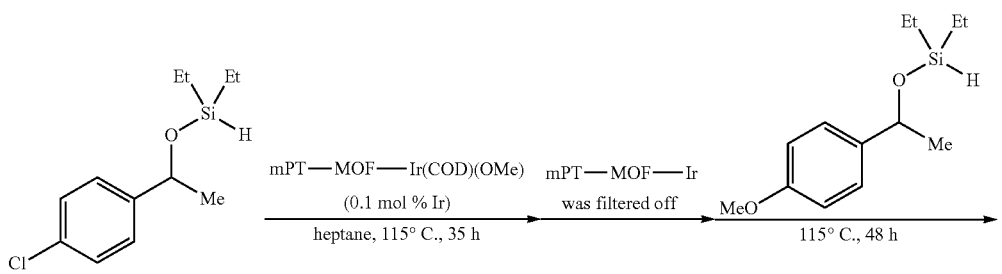

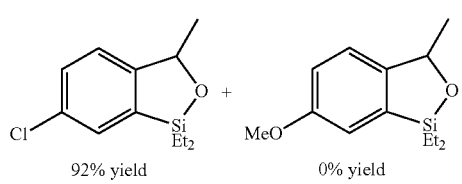

A mixture diethyl(hydrido)silyl ether (2g, 91.3 mg, 359.5 μmol) and mPT-MOF-Ir (5.0 mg, 0.1 mol % Ir) in 4.0 mL n-heptane were charged into a Schlenk tube. The mixture was refluxed under nitrogen at 115° C. for 35 h. The solid catalyst was separated via centrifugation. The extract was passed through a short plug of celite and then concentrated in vacuo to give benzoxasilole (3g) in 94% yield.

A mixture of diethyl(hydrido)silyl ether (2g, 91.3 mg, 359.5 μmol) and mPT-MOF-Ir (5.0 mg, 0.1 mol % Ir) in 4.0 mL n-heptane were refluxed into a Schlenk tube at 115° C. for 20 h under nitrogen. The solid catalyst was separated via centrifugation and the supernatant was filtered through a celite. Then, diethyl(hydrido)silyl ether (2f, 91.3 mg, 359.5 μmol) was added to the supernatant and the resultant solution was refluxed at 115° C. for an additional 48 h. The analysis of the solution by GC revealed that the yields of 3g and 3f were 92% and 0% respectively. These two experiments confirm the heterogeneity of mPT-MOF-Ir in the C—H silylation of arenes.

Quantification of Hydrogen Production in Dehydrogenative Ortho-Silylation of Arenes.

A J. Young NMR tube (total volume 2.75 mL) was charged with mPT-MOF-Ir catalyst (2 mg), diethyl(hydrido)silyl ether (2g, 20.0 mg, 0.087 mmol) and n-heptane solvent to a total volume of 0.75 mL. The tube was sealed under nitrogen atmosphere and heated to 115° C. for 44 h. After cooling to room temperature, the headspace gas was analyzed by gas chromatography to give a hydrogen content of 31.8% (v/v). Thus, the total amount of hydrogen in the headspace was calculated to be 2.00 mL×31.8/68.2×101 kPa÷8.134 J·mol$^{-1}$·K$^{-1}$÷295 K=0.038 mmol which corresponded to a conversion of 44%. Meanwhile, $^1$H NMR spectrum of the crude product gave a conversion of 45%. Thus, production of stoichiometric amount of hydrogen was confirmed.

Recyclability Test for mPT-MOF-Ir Catalyzed Ortho-Silylation of Arenes.

In a glovebox, mPT-MOF-Ir (5.0 mg, 0.5 mol % Ir) and diethyl(hydrido)silyl ether (2g, 46.5 mg, 203.2 μmol) in 4 mL n-heptane were charged into a Schlenk tube. The mixture was heated to reflux at 115° C. under nitrogen with slow stirring for 12 h. The reaction mixture was cooled to room temperature and the solid was centrifuged out of suspension in the glovebox. All the volatiles of the supernatant were removed in vacuo to give crude benzoxasilole (3g) as a colorless oil (isolated yield of crude product: 46.3 mg, 192.4 μmol, 94.7%; GC yield: 96%), which was sufficiently pure as determined by $^1$H NMR spectroscopy.

The recovered solid catalyst was added to a 4.0 mL solution of diethyl(hydrido)silyl ether (2g, 46.5 mg, 203.2 μmol) in 4 mL n-heptane and transferred to the storage tube. After heating at 115° C. for 12 h, the solid catalyst was separated via centrifugation in the glovebox. The volatiles of the supernatant were removed in vacuo to give 3g (GC yield: 99%).

Time Evaluation Studies for Ortho-Silylation of Arenes Using mPT-MOF-Ir and {pth}Ir(COD)(OMe) {pth=3,8-bis(4-methoxycarbonylphenyl)phenanthroline} as Catalysts Under Identical Conditions.

Diethyl(hydrido)silyl ether (5b, 116.2 mg, 507.9 μmol), mPT-MOF-Ir (5.0 mg, 0.2 mol % Ir) and n-heptane (4.0 mL) were charged into a Schlenk tube in a glovebox. Another Schlenk tube was charged with 5b (116.2 mg, 507.9 μmol), {pth}Ir(COD)(OMe) (2.0 mg, 2.54 μmol, 0.5 mol % Ir) and n-heptane (3.0 mL). The two storage tubes were heated at 115° C. simultaneously and the conversion (%) of the product was monitored by GC using mesitylene as an internal standard in 1 d interval of heating.

A Typical Procedure for mPT-MOF-Ir Catalyzed Tandem Dehydrocoupling of N-Methylbenzyl Amines and Intramolecular Ortho-Silylation of (Hydrido)Silyl Amines to Azasilolanes Scheme 33. Recycle and reuse of mPT—MOF—Ir for ortho-silylation of arenes.

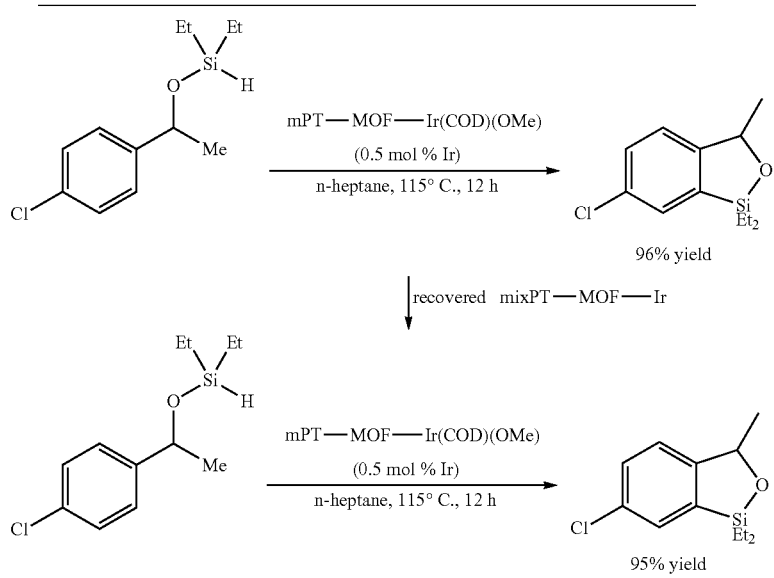

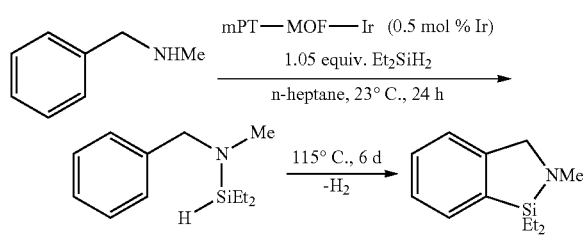

In a glovebox, mPT-MOF-Ir (5.0 mg, 0.5 mol % Ir), N-methyl benzyl amine (7a, 24.6 mg, 0.202 mmol) and Et$_2$SiH$_2$ (27.6 mL, 0.213 mmol) in 4.0 mL n-heptane were charged into a Schlenk tube. The tube was left in the glovebox for 24 h to afford (hydrido)silyl amine (8a) in complete conversion. Then, the tube was heated to reflux at 115° C. under nitrogen for 6 d. The reaction mixture was cooled to room temperature. The solid was centrifuged out of suspension and was extracted with n-heptane 3 times in the glovebox. The combined organic extracts were concentrated in vacuo yielding azasilolane (9a, 92%).

A Typical Procedure for mBPV-MOF-Ir Catalyzed C—H Borylation of Neat Arenes.

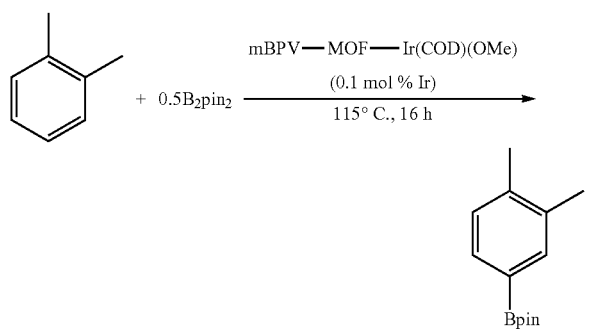

In a glovebox, mBPV-MOF-Ir in THF (3.0 mg, 0.1 mol % Ir) was quickly weighed onto a filter paper, charged into a vial. B$_2$pin$_2$ (54.8 mg, 0.216 mmol) in 4.0 mL o-xylene was added to the vial and the resultant mixture was transferred to a Schlenk tube. The tube was heated to reflux under nitrogen at 115° C. for 16 h. The reaction mixture was cooled to room temperature and the solid was centrifuged out of suspension. The extract was passed through a short plug of celite and then concentrated in vacuo to give pure 1,2-dimethyl-4-(4,4,5,5-tetramethyl-1,3,2-dioxaborolan-2-yl)benzene as (48.5 mg, 0.209 mmol, 96.8%).

TABLE 29

Optimization of reaction conditions for catalytic C—H borylation of m-xylene[a]

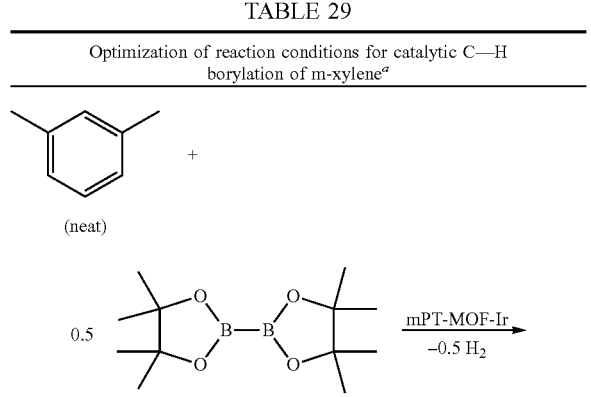

TABLE 29-continued

| Entry | Ir loading (mol %) | Temperature (° C.) | Time | Conversion (%)[b] |
|---|---|---|---|---|
| 1 | 0.1 | 115 | 32 h | 100 |
| 2 | 0.1 | 120 | 32 h | 100 |
| 3 | 0.01 | 115 | 7 d | 45 |

[a]Reaction conditions: 5 mg mPT-MOF-Ir, 4.0 ml solvent. [b]Conversion was determined by GC analysis.

TABLE 30

Optimization of reaction conditions for catalytic C—H borylation of arenes.[a]

| Entry | Ir loading (mol %) | Solvent | Temperature (° C.) | Time | Conversion (%)[b] |
|---|---|---|---|---|---|
| 1 | 0.1 | n-heptane | 115 | 15 h | 100 |
| 2 | 0.1 | n-octane | 120 | 22 h | 90 |
| 3 | 0.01 | n-heptane | 115 | 9 d | 80 |
| 4 | 0.1 | THF | 80 | 24 h | 96 |

[a]Reaction conditions: 5.0 mg of mPT-MOF-Ir, 2.0 ml solvent. [b]Conversion was determined by GC analysis.

Procedure for mPT-MOF-Ir(COD)-Cl Catalyzed C—H Borylation of Neat Arenes.

In a glovebox, mPT-MOF-Ir(COD)-Cl (3.0 mg, 0.1 mol % Ir) in benzene was charged into a Schlenk flask. B$_2$pin$_2$ (20 mg, 78.7 μmol) in 3.0 mL benzene was added to the flask and the resultant mixture was heated to reflux under nitrogen at 90° C. for 38 h until complete conversion as monitored by GC analysis to afford (4,4,5,5-Tetramethyl-1,3,2-dioxaborolan-2-yl)benzene. In contrast, under identical reaction conditions, 0.1 mol % of mPT-MOF-Ir afforded (4,4,5,5-Tetramethyl-1,3,2-dioxaborolan-2-yl)benzene quantitavely within 18 h. Therefore, mPT-MOF-Ir is more active in C—H borylation recation compared to mPT-MOF-Ir(COD)-Cl.

Recyclability Test for mPT-MOF-Ir in Borylation of Arenes.

Scheme 34. Recycle and reuse of mPT—MOF—Ir for C—H borylation of m-xylene.

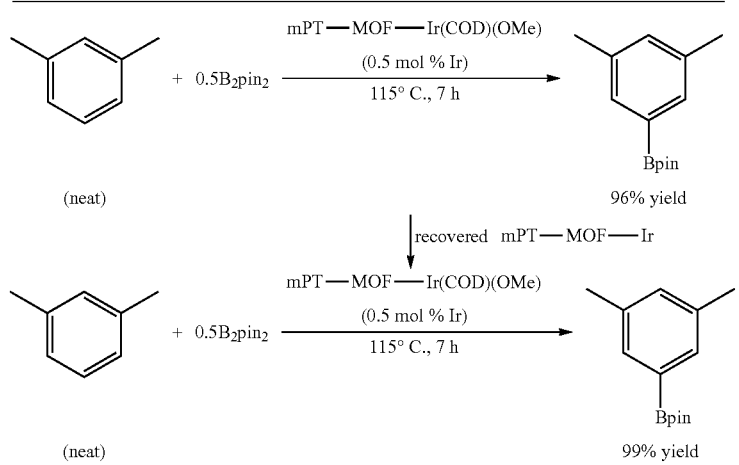

In a glovebox, m-xylene (4.0 mL), B$_2$pin$_2$ (25.8 mg, 101.6 μmol) and mPT-MOF-Ir (5.0 mg, 0.5 mol % Ir) were charged into a Schlenk tube. The mixture was heated to reflux under nitrogen at 115° C. in an oil bath until complete consumption of B$_2$pin$_2$ was observed as determined by GC analysis (generally 7-10 h). During heating, the solution was slowly stirred. After completion of the reaction, the mixture was cooled to room temperature and the solid catalyst was separated via centrifugation in the glovebox. All the volatiles of the supernatant were removed in vacuo to give crude 5-(4,4,5,5-tetramethyl-1,3,2-dioxaborolan-2-yl)-m-xylene as a colorless solid (isolated yield of crude product: 33.56 mg, 190.7 μmol, 93.9%; GC yield: 96%), which was sufficiently pure as indicated by $^1$H NMR spectroscopy.

The recovered solid catalyst was added to a 4.0 mL solution of B$_2$pin$_2$ (25.8 mg, 101.6 μmol) in m-xylene and transferred to the Schlenk tube. After refluxing at 115° C. for 7 h, the solid catalyst was separated via centrifugation in the glovebox. The volatiles of the supernatant was removed in vacuo to give 5-(4,4,5,5-Tetramethyl-1,3,2-dioxaborolan-2-yl)-m-xylene (GC yield: 99%).

Recyclability Test for mixBPV-MOF-Ir in Borylation of Arenes.

In a glovebox, B$_2$pin$_2$ (18.3 mg, 71.9 μmol), indole (17.1 mg, 143.5 μmol), n-heptane (4.0 mL), and mPT-MOF-Ir (5.0 mg, 0.5 mol % Ir) were charged into a Schlenk tube. The mixture was refluxed under nitrogen at 115° C. in an oil bath for 3-4 h. During heating, the solution was slowly stirred. After completion of the reaction, the mixture was cooled to room temperature and the solid catalyst was separated via centrifugation in the glovebox. All the volatiles of the supernatant were removed in vacuo to give crude 2-(4,4,5,5-tetramethyl-1,3,2-dioxaborolan-2-yl)-1H-indole as a colorless solid (isolated yield of crude product: 33.6 mg, 138.0 μmol, 96.2%; GC yield: 97%), which was sufficiently pure as determined by $^1$H NMR spectroscopy.

4.0 mL solution of B$_2$pin$_2$ (18.3 mg, 71.9 μmol) and indole (17.1 mg, 143.5 μmol) in m-xylene was added to the recovered solid catalyst and then the mixture was transferred to the Schlenk tube. After heating at 115° C. for 4 h, the solid catalyst was separated via centrifugation in the glovebox. The volatiles of the supernatant was removed in vacuo to give 2-(4,4,5,5-tetramethyl-1,3,2-dioxaborolan-2-yl)-1H-indole (GC yield: 100%).

Scheme 35. Recycle and reuse of mBPV—MOF—Ir for C—H borylation of indole.

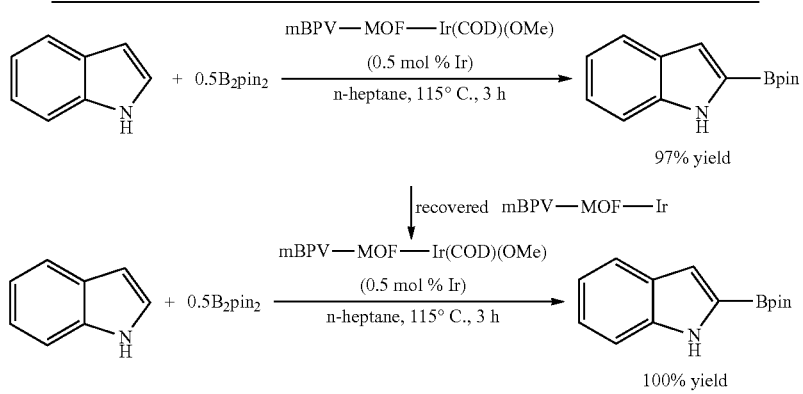

Test of "Heterogeneity" of mBPV-MOF-Ir

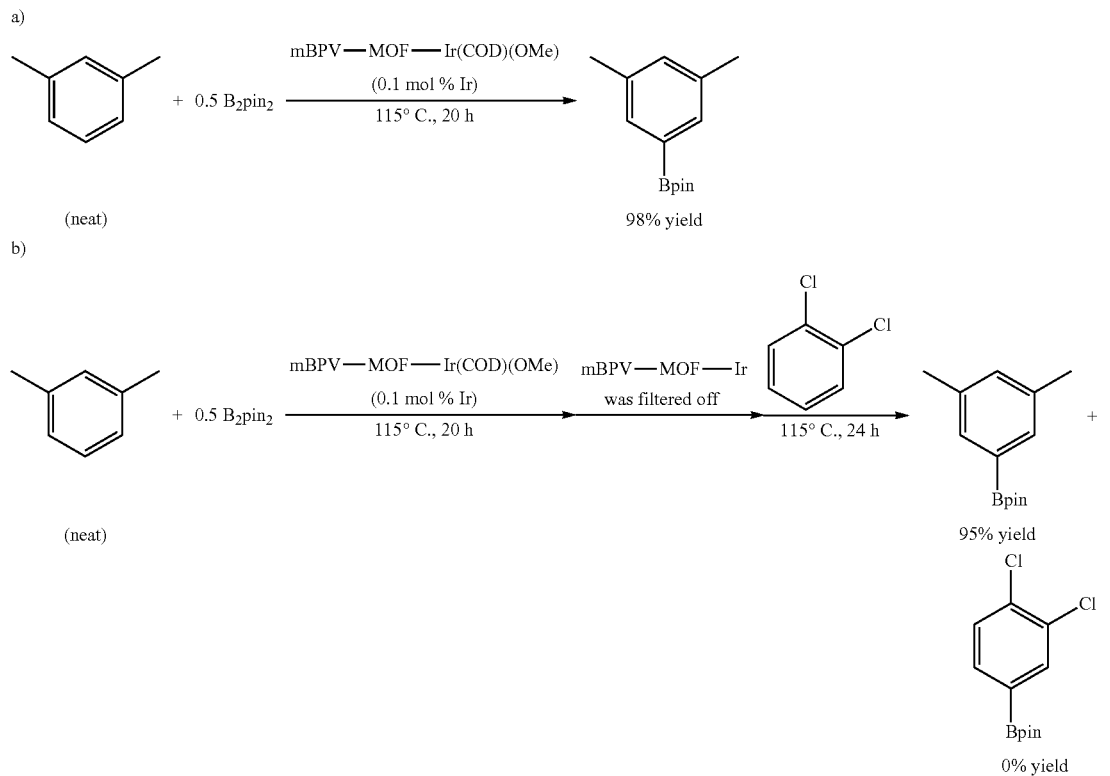

Scheme 36. The C—H borylation of 1,2-dichlorobenzene stopped after removing mBPV—MOF—Ir from the reaction mixture, demonstrating the "heterogeneous" nature of MOF catalysis.

A mixture of m-xylene (4.0 mL), B$_2$pin$_2$ (91.3 mg, 359.5 μmol) and mBPV-MOF-Ir (5.0 mg, 0.1 mol % Ir) were charged into a Schlenk tube. The tube was heated to reflux under nitrogen at 115° C. for 20 h. The solid catalyst was separated via centrifugation. The extract was passed through a short plug of celite and then concentrated in vacuo to give 5-(4,4,5,5-tetramethyl-1,3,2-dioxaborolan-2-yl)-m-xylene in 98% yield.

A mixture of m-xylene (2.0 mL), B$_2$pin$_2$ (91.3 mg, 359.5 μmol) and mBPV-MOF-Ir (5.0 mg, 0.1 mol % Ir) were heated into a Schlenk tube at 115° C. for 20 h. The solid catalyst was separated via centrifugation and the supernatant was filtered through a celite. Then, 2.0 mL 1,2-dichlorobenzene was added to the supernatant and the resultant solution was stirred at 115° C. for an additional 24 h. The analysis of the solution by GC revealed that the yields of 5-(4,4,5,5-tetramethyl-1,3,2-dioxaborolan-2-yl)-m-xylene and 1,2-dichloro-4-(4,4,5,5-tetramethyl-1,3,2-dioxaborolan-2-yl)benzene were 95% and 0% respectively.

These two experiments confirm the heterogeneity of mBPV-MOF in the C—H borylation of arenes.

Time Evaluation Studies for C—H Borylation of Arenes Using mPT-MOF-Ir and {pth}Ir(COD)(OMe) as Catalysts Under Identical Conditions.

B$_2$pin$_2$ (644.8 mg, 2.54 mmol), mPT-MOF-Ir (5.0 mg, 0.02 mol % Ir) in 4 mL m-xylene were charged into a Schlenk tube in a glovebox. Another Schlenk tube was charged with B$_2$pin$_2$ (644.8 mg, 2.54 mmol), {pth}Ir(COD)(OMe) (0.80 mg, 1.02 μmol, 0.02 mol % Ir) in 4 mL m-xylene. The two storage tubes were heated at 115° C. simultaneously and the conversion (%) of the product was monitored by GC using mesitylene as an internal standard in 1 d interval of heating.

Tests to Rule Out the Involvement of Zr-SBUs in Borylation Reactions.

In a glovebox, a vial was charged with TPHN-MOF (built from unfunctionalized 4,4'-bis(carboxyphenyl)-2-nitro-1,1'-biphenyl ligand) (12 mg), [Ir(COD)(OMe)]$_2$ (6 mg) and 2 mL THF. The resultant mixture was stirred slowly for 18 h. During stirring, the light yellow color of TPHN-MOF did not change. The resultant light yellow solid was centrifuged out of suspension and washed with THF 4-5 times. the resulting TPHN-MOF (5.0 mg) in benzene was charged into a Schlenk flask. B$_2$pin$_2$ (20 mg, 78.7 μmol) in 3.0 mL benzene was added to the flask and the resultant mixture was heated to reflux under nitrogen at 95° C. for 18 h. No C—H borylation of benzene was observed, which rule out the role of any Zr-SBU-Ir species in catalytic borylation reactions.

7. GC Analysis

The conversions of reactions and yields of the products were determined by gas chromatography (GC) using a Shimadzu GC-2010 gas chromatograph equipped with a flame ionization detector (FID) and Supelco β-dex 120 column. GC conditions: Inj: 220° C.; Det: 250° C.; Column temp: 80° C. followed by a ramp of 2° C./min to 200° C. and held for 10 minutes; Column flow: 1.11 mL/min.

TABLE 30
Retention Time of GC Traces.
| Compounds | Retention time (min) |
|---|---|
| 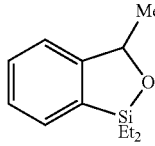 | 35.6 |
| 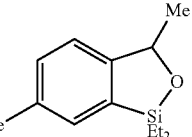 | 44.3 |
| 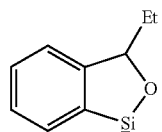 | 33.0 |
| 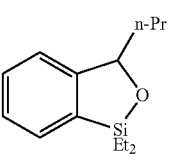 | 39.7 |
| 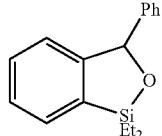 | 39.9 |
| 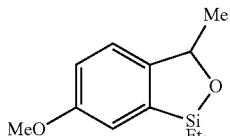 | 44.3 |
| 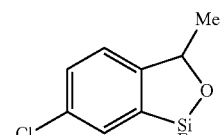 | 40.1 |
| 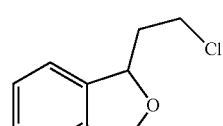 | 42.8 |
| 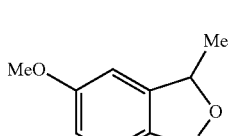 | 39.6 |
TABLE 30-continued
Retention Time of GC Traces.
| Compounds | Retention time (min) |
|---|---|
| 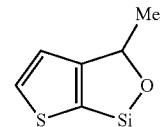 | 27.3, 27.5 |
| 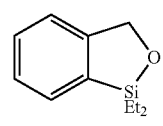 | 28.2 |
| 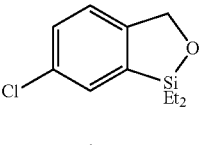 | 40.0 |
| 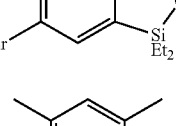 | 43.2 |
| 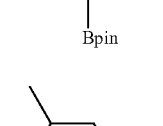 | 42.0 |
| 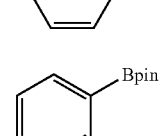 | 43.1 |
| 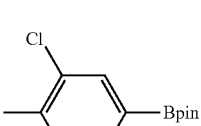 | 32.5 |
| 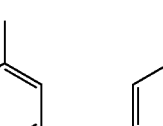 | 47.4 |
| 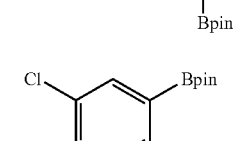 | 40.0, 40.3 |
|  | 46.0 |

TABLE 30-continued

Retention Time of GC Traces.

| Compounds | Retention time (min) |
|---|---|
| 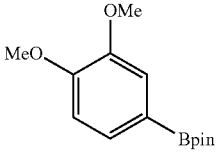 | 47.1 |
| 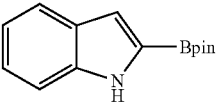 | 41.0 |
| 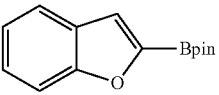 | 52.9 |

Summary of Example 11

Three porous Zr-MOFs (BPV-MOF, mBPV-MOF and mPT-MOF) of UiO-topology with elongated bipyridyl- and phenanthryl-containing bicarboxylate linkers were constructed. The straightforward postsynthetic metalation of these UiO-MOFs with [Ir(COD)(OMe)]$_2$ afforded highly active and robust single-site solid catalysts for three important organic transformations via directed C—H activation: tandem hydrosilylation/ortho-silylation of aryl ketones and aldehydes, tandem dehydrocoupling/ortho-silylation reactions of N-methylbenzyl amines, and borylations of aromatic C—H bonds. In all three reactions, mixed-linker MOF catalysts (mMOF-Ir) are much more active than BPV-MOF containing only functionalized linkers. While it is not desired to be bound by any particular theory of operation, we believe that mMOF catalysts have much larger open channels due to the doping of bulky functionalized linkers and their resulting Ir complexes into less sterically demanding unfunctionalized linkers, which facilitates the transport of the substrates and products through the MOF channels. It was also observed that mMOF catalysts show much enhanced activities and stability when compared to their homogenous analogues, likely due to active site isolation in MOF structures which prevents any intermolecular deactivation pathways. In addition, these solid catalysts can be readily recycled and reused for more than 15 times. Example 11 thus provides another representative embodiment of a simple and efficient doping strategy to enlarge the open channels of catalytically active MOFs and highlights the enormous potential of developing MOF catalysts based on nitrogen-donor ligands for practical synthesis of fine chemicals.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for preparing a crystalline and porous metal-organic framework (MOF), wherein said crystalline and porous MOF comprises periodic repeats of a metal-based secondary building unit (SBU) and a nitrogen donor-based bridging ligand, said method comprising:
providing a nitrogen donor-based bridging ligand, wherein said nitrogen donor-based bridging ligand is a derivative of a 5,5'-bis(vinyl)-2,2'-bipyridine;
contacting the nitrogen donor-based bridging ligand with a first metal source to obtain the crystalline and porous MOF; and
contacting the crystalline and porous MOF with a second metal source to metalate the bridging ligand, wherein the second metal source comprises a metal selected from the group consisting of Fe, Co, Ni, Rh, Ru, Ir, Os, Pd, V, Cr, and Mn.

2. The method of claim 1, wherein the 5,5'-bis(vinyl)-2,2'-bipyridine is substituted by two or more substituents selected from a carboxylate, pyridine, and/or phosphonate moiety.

3. The method of claim 2, wherein the nitrogen donor-based bridging ligand is a 5,5'-bis(vinyl)-2,2'-bipyridine substituted with two carboxylate groups.

4. The method of claim 1, wherein the nitrogen donor-based bridging ligand is 5,5'-bis(carboxyvinyl)-2,2'-bipyridine.

5. The method of claim 1, wherein the SBU is selected from the group comprising Hf-oxo clusters, Zr-oxo clusters, Zn-oxo clusters, Ti-oxo clusters, Cu-carboxylate paddle-wheels, and other SBUs used to construct MOFs.

6. The method of claim 1, wherein the first metal source is a metal alkoxide or a metal halide.

7. The method of claim 1, wherein the first metal source is ZrCl$_4$.

8. The method of claim 1, wherein the second metal source is FeCl$_3$, CoCl$_2$, NiCl$_2$.

9. The method of claim 1, wherein the MOF further comprises a bridging ligand that is not a nitrogen donor-based bridging ligand.

10. The method of claim 1, wherein the nitrogen donor-based bridging ligand and the first metal source are contacted in a solvent or mixture of solvents selected based on solvent molecule size, such that the sizes and/or shapes of internal pores, cavities, and/or open channels in the crystalline and porous MOF can be tailored to enhance catalytic activity and selectivity.

11. A heterogeneous catalyst comprising a crystalline and porous MOF, wherein said crystalline and porous MOF comprises periodic repeats of a metal-based secondary building unit (SBU), wherein said metal-based SBU comprises a first metal, and a nitrogen donor-based bridging ligand, wherein said nitrogen donor-based bridging ligand is a derivative of a 5,5'-bis(vinyl)-2,2'-bipyridine; and wherein said nitrogen donor-based bridging ligand is further complexed to a second metal, wherein the second metal is selected from the group consisting of Fe, Co, Ni, Rh, Ru, Ir, Os, Pd, V, Cr, and Mn.

12. A heterogeneous catalyst prepared according to the method of claim 1.

13. A method for preparing a compound comprising contacting a substrate capable of forming a product by catalytic transformation with a heterogeneous catalyst of claim 11.

14. The method of claim 13, wherein the catalytic transformation is selected from the group comprising hydrogenation; dehydrogenation; isomerization, optionally the isomerization of an allylamine, an allyl alcohol, or an α,β-unsaturated ketone; allylic substitution; a coupling reaction, optionally wherein the coupling reaction is a Buchwald-Hartwig amination, an intramolecular Heck reaction, or an intermolecular Heck reaction; conjugate addition, optionally wherein the conjugate addition is a Michael addition or an azo-Michael addition; an aldol reaction; a Mannich-type reaction; nucleophilic addition, optionally wherein the nucleophilic addition is to a carbonyl or imine group and/or wherein the nucleophilic addition is a cyanation, a propargylation, an allylation, a dienylation, an arylation, an alkenylation, or an alkylation; hydroformylation; hydroacylation; hydroboration; hydroamination; intra- or intermolecular hydrosilylation; an α-substitution reaction, optionally wherein the α-substitution reaction is a protonation, a fluorination, an amination, an arylation, or an orthoester alkylation; an ene reaction; a Diels-Alder reaction; a Pauson-Khand reaction; an enyne intramolecular cyclization; a [2+2+2] cycloaddition; a [3+2] cycloaddition; and a ring-opening reaction.

15. The heterogeneous catalyst of claim 11, wherein the MOF further comprises a bridging ligand that is not a nitrogen donor-based bridging ligand.

* * * * *